US009873887B2

(12) United States Patent
Fillatti et al.

(10) Patent No.: US 9,873,887 B2
(45) Date of Patent: *Jan. 23, 2018

(54) SOYBEAN SEED AND OIL COMPOSITIONS AND METHODS OF MAKING SAME

(71) Applicant: Monsanto Technology LLC, St. Louis, MO (US)

(72) Inventors: Joanne J. Fillatti, Davis, CA (US); Greg E. Keithly, Chesterfield, MO (US); Toni Voelker, Davis, CA (US); Tim Ulmasov, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,520

(22) Filed: Jan. 7, 2016

(65) Prior Publication Data

US 2016/0130600 A1    May 12, 2016

Related U.S. Application Data

(60) Continuation of application No. 14/085,933, filed on Nov. 21, 2013, now Pat. No. 9,410,161, which is a division of application No. 13/669,024, filed on Nov. 5, 2012, now Pat. No. 8,609,953, which is a division of application No. 13/080,087, filed on Apr. 5, 2011, now abandoned, which is a continuation of application No. 12/713,388, filed on Feb. 26, 2010, now Pat. No. 7,943,818, which is a division of application No. 11/684,413, filed on Mar. 9, 2007, now Pat. No. 7,790,953.

(60) Provisional application No. 60/781,519, filed on Mar. 10, 2006.

(51) Int. Cl.
    C12N 15/82    (2006.01)
    A01H 5/10     (2006.01)
    A23D 9/00     (2006.01)
    C11B 1/10     (2006.01)
    C11C 1/00     (2006.01)

(52) U.S. Cl.
    CPC .......... C12N 15/8247 (2013.01); A01H 5/10 (2013.01); A23D 9/00 (2013.01); C11B 1/10 (2013.01); C11C 1/002 (2013.01); C12N 15/8218 (2013.01)

(58) Field of Classification Search
    None
    See application file for complete search history.

(56) References Cited

U.S. PATENT DOCUMENTS

| | | |
|---|---|---|
| 4,089,880 A | 5/1978 | Sullivan |
| 4,915,972 A | 4/1990 | Gupta et al. |
| 4,948,811 A | 8/1990 | Spinner et al. |
| 5,130,449 A | 7/1992 | Lagarde et al. |
| 5,208,058 A | 5/1993 | Kotani et al. |
| 5,260,077 A | 11/1993 | Carrick et al. |
| 5,278,325 A | 1/1994 | Strop et al. |
| 5,286,886 A | 2/1994 | Van de Sande et al. |
| 5,315,020 A | 5/1994 | Cheng et al. |
| 5,387,758 A | 2/1995 | Wong et al. |
| 5,401,866 A | 3/1995 | Cheng et al. |
| 5,434,283 A | 7/1995 | Wong et al. |
| 5,516,924 A | 5/1996 | van de Sande et al. |
| 5,520,708 A | 5/1996 | Johnson et al. |
| 5,530,183 A | 6/1996 | Fehr et al. |
| 5,534,425 A | 7/1996 | Fehr et al. |
| 5,545,821 A | 8/1996 | Wong et al. |
| 5,625,130 A | 4/1997 | Grant et al. |
| 5,658,767 A | 8/1997 | Kyle |
| 5,696,278 A | 12/1997 | Segers |
| 5,710,365 A | 1/1998 | Kerr et al. |
| 5,710,369 A | 1/1998 | Fehr et al. |
| 5,714,668 A | 2/1998 | Fehr et al. |
| 5,714,669 A | 2/1998 | Fehr et al. |
| 5,714,670 A | 2/1998 | Fehr et al. |

(Continued)

FOREIGN PATENT DOCUMENTS

| | | |
|---|---|---|
| CA | 2479587 A1 | 10/2003 |
| DE | 2922146 A1 | 7/1980 |

(Continued)

OTHER PUBLICATIONS

Cargill, Clear Valley 65, High Oleic Canola Oil, Zero Trans Fat Oil with Exceptional Stability in High Heat Applications. Product brochure, www.clearvalleyoils.com.
Mickel et al., Effect of inert gases on the autoxidation of cis and trans polyunsaturated fatty acid methyl ester Rivista Italiana Della Sostanze Grasse, 53:312-314 (1976).
Sayanova et al., Identification of primula fatty acid desaturases with n-3 FEBS Letters, 542:100-104, 2003.
Invitation/Partial Search Report issued in analogous application No. PCT/US2005/039809 dated Apr. 7, 2006.

(Continued)

*Primary Examiner* — Eileen B O Hara
(74) *Attorney, Agent, or Firm* — Thompson Coburn LLP; Charles P. Romano; Chunping Li

(57) ABSTRACT

Methods for obtaining soybean plants that produce seed with low linolenic acid levels and moderately increased oleic levels are disclosed. Also disclosed are methods for producing seed with low linolenic acid levels, moderately increased oleic levels and low saturated fatty acid levels. These methods entail the combination of transgenes that provide moderate oleic acid levels with soybean germplasm that contains mutations in soybean genes that confer low linolenic acid phenotypes. These methods also entail the combination of transgenes that provide both moderate oleic acid levels and low saturated fat levels with soybean germplasm that contains mutations in soybean genes that confer low linolenic acid phenotypes. Soybean plants and seeds produced by these methods are also disclosed.

13 Claims, 6 Drawing Sheets

(56) References Cited

U.S. PATENT DOCUMENTS

| | | | |
|---|---|---|---|
| 5,723,761 A | 3/1998 | Voelker et al. |
| 5,750,844 A | 5/1998 | Fehr et al. |
| 5,763,745 A | 6/1998 | Fehr et al. |
| 5,767,338 A | 6/1998 | Fan |
| 5,795,969 A | 8/1998 | Fehr et al. |
| 5,840,946 A | 11/1998 | Wong et al. |
| 5,850,026 A | 12/1998 | DeBonte et al. |
| 5,850,030 A | 12/1998 | Fehr et al. |
| 5,859,350 A | 1/1999 | DeBonte et al. |
| 5,863,589 A | 1/1999 | Covington, Jr. et al. |
| 5,866,762 A | 2/1999 | DeBonte et al. |
| 5,955,329 A | 9/1999 | Yuan et al. |
| 5,955,650 A | 9/1999 | Hitz |
| 5,965,755 A | 10/1999 | Semyk et al. |
| 5,969,169 A | 10/1999 | Fan |
| 5,981,781 A | 11/1999 | Knowlton |
| 5,986,118 A | 11/1999 | Fehr et al. |
| 6,022,577 A | 2/2000 | Chrysam et al. |
| 6,063,424 A | 5/2000 | Wells et al. |
| 6,133,509 A | 10/2000 | Fehr et al. |
| 6,147,237 A | 11/2000 | Zwanenburg et al. |
| 6,169,190 B1 | 1/2001 | Lanuza et al. |
| 6,172,248 B1 | 1/2001 | Copeland et al. |
| 6,184,442 B1 | 2/2001 | Nickell |
| 6,201,145 B1 | 3/2001 | Fan |
| 6,229,033 B1 | 5/2001 | Knowlton |
| 6,303,849 B1 | 10/2001 | Potts et al. |
| 6,313,328 B1 | 11/2001 | Ulrich et al. |
| 6,331,664 B1 | 12/2001 | Rubin-Wilson et al. |
| 6,340,485 B1 | 1/2002 | Coupland et al. |
| 6,365,802 B2 | 4/2002 | Kridl |
| 6,369,302 B1 | 4/2002 | Matson |
| 6,372,965 B1 | 4/2002 | Lightner et al. |
| 6,376,754 B1 | 4/2002 | Schillinger et al. |
| 6,380,462 B1 | 4/2002 | Kridl |
| 6,384,301 B1 | 5/2002 | Martinell et al. |
| 6,388,110 B1 | 5/2002 | Ulrich et al. |
| 6,388,113 B1 | 5/2002 | Martinez Force et al. |
| 6,426,448 B1 | 7/2002 | Booth, Jr. et al. |
| 6,559,325 B2 | 5/2003 | Fan |
| 6,562,397 B2 | 5/2003 | DeBonte et al. |
| 6,583,303 B1 | 6/2003 | DeBonte et al. |
| 6,593,514 B1 | 7/2003 | Cahoon et al. |
| 6,610,867 B2 | 8/2003 | Jakel et al. |
| 6,667,064 B2 | 12/2003 | Surette |
| 6,791,016 B1 | 9/2004 | Steiger et al. |
| 6,797,172 B2 | 9/2004 | Koseoglu et al. |
| 6,844,021 B2 | 1/2005 | Koike et al. |
| 6,906,211 B2 | 6/2005 | Tysinger et al. |
| 6,924,381 B2 | 8/2005 | Dawson |
| 7,067,722 B2 | 6/2006 | Fillatti |
| 7,166,771 B2 | 1/2007 | Eenennaam et al. |
| 7,442,850 B2 | 10/2008 | Wu et al. |
| 7,531,718 B2 * | 5/2009 | Fillatti ............... C07K 14/415 |
| | | | 800/281 |
| 7,579,492 B2 | 8/2009 | Tysinger |
| 7,741,500 B2 | 6/2010 | Arhancet et al. |
| 7,750,206 B2 * | 7/2010 | Li ..................... C12N 9/1051 |
| | | | 435/320.1 |
| 7,790,953 B2 * | 9/2010 | Fillatti .................. A01H 5/10 |
| | | | 800/278 |
| 7,902,388 B2 | 3/2011 | Heise et al. |
| 7,943,818 B2 * | 5/2011 | Fillatti .................. A01H 5/10 |
| | | | 800/278 |
| 7,973,212 B2 | 7/2011 | Sebastian |
| 8,013,217 B2 | 9/2011 | Wu et al. |
| 8,057,835 B2 | 11/2011 | Makadia et al. |
| 8,378,170 B2 | 2/2013 | Wu et al. |
| 8,609,953 B2 * | 12/2013 | Fillatti .................. A01H 5/10 |
| | | | 435/415 |
| 9,062,319 B2 * | 6/2015 | Fillatti .................. A01H 5/10 |
| 9,410,161 B2 * | 8/2016 | Fillatti .................. A01H 5/10 |
| 2002/0058340 A1 | 5/2002 | Clemente et al. |
| 2003/0024011 A1 | 1/2003 | Dehesh et al. |
| 2003/0172399 A1 | 9/2003 | Fillatti |
| 2003/0180434 A1 | 9/2003 | Fan |
| 2004/0006792 A1 | 1/2004 | Fillatti et al. |
| 2004/0047971 A1 | 3/2004 | Alander |
| 2004/0049813 A1 | 3/2004 | Russell et al. |
| 2004/0107460 A1 | 6/2004 | Fillatti et al. |
| 2006/0080750 A1 | 4/2006 | Fillatti et al. |
| 2006/0107348 A1 | 5/2006 | Wu et al. |
| 2006/0110521 A1 | 5/2006 | Heise et al. |
| 2006/0111578 A1 | 5/2006 | Arhancet et al. |
| 2006/0206963 A1 | 9/2006 | Voelker et al. |
| 2007/0212780 A1 | 9/2007 | Fillatti |
| 2008/0092251 A1 | 4/2008 | Lightner et al. |
| 2008/0222756 A1 | 9/2008 | Fillatti et al. |
| 2009/0193547 A1 | 7/2009 | Wu et al. |
| 2009/0214744 A1 | 8/2009 | Kridl |
| 2010/0218269 A1 | 8/2010 | Fillatti et al. |
| 2011/0067149 A1 | 3/2011 | Wagner |
| 2011/0239335 A1 | 9/2011 | Fillatti et al. |
| 2012/0028255 A1 | 2/2012 | Wu et al. |
| 2012/0058235 A1 | 3/2012 | Makadia et al. |

FOREIGN PATENT DOCUMENTS

| | | |
|---|---|---|
| EP | 0226245 A1 | 6/1987 |
| EP | 0077528 A1 | 4/1989 |
| EP | 0323753 A1 | 7/1989 |
| EP | 0326198 A2 | 8/1989 |
| EP | 0347056 A1 | 12/1989 |
| EP | 0348004 A2 | 12/1989 |
| EP | 0476093 A1 | 3/1992 |
| EP | 0526954 A2 | 2/1993 |
| EP | 0606359 A1 | 7/1994 |
| EP | 0639333 A1 | 2/1995 |
| EP | 0672096 A1 | 9/1995 |
| EP | 0813357 A1 | 12/1997 |
| EP | 0833882 A1 | 4/1998 |
| EP | 0936266 A1 | 8/1999 |
| EP | 1161877 A1 | 12/2001 |
| EP | 1794309 A1 | 6/2007 |
| GB | 715352 A | 9/1954 |
| GB | 2241503 A | 9/1991 |
| JP | S63-44843 | 2/1988 |
| JP | 10-191885 A | 7/1998 |
| WO | 93/19626 A1 | 10/1993 |
| WO | 9411516 A1 | 5/1994 |
| WO | 96/36684 A1 | 11/1996 |
| WO | 9740698 A1 | 11/1997 |
| WO | 99/58689 A1 | 11/1999 |
| WO | 99/64614 A2 | 12/1999 |
| WO | 00/44862 A1 | 8/2000 |
| WO | 01/14538 A2 | 3/2001 |
| WO | 02/092073 A1 | 11/2002 |
| WO | 03/049832 A1 | 6/2003 |
| WO | 03/080802 A2 | 10/2003 |
| WO | 2004/000871 A2 | 12/2003 |
| WO | 2004/001000 A2 | 12/2003 |
| WO | 2004/001001 A2 | 12/2003 |
| WO | 04/009827 A2 | 1/2004 |
| WO | 04/071467 A2 | 8/2004 |
| WO | 2006039449 A1 | 4/2006 |
| WO | 07/106728 A2 | 9/2007 |

OTHER PUBLICATIONS

Wilson et al., "Effect of Controlled Atmosphere Storage on Aflatoxin Production in High Moisture Peanuts (Groundnuts)," J. Stored Prod. Res., 12:97-100, 1976.
PCT International Search Report for analogous application No. PCT/US2005/039809 dated Jun. 13, 2006.
List et al., "Potential Margarine Oils from Genetically Modified Soybeans," JAOCS, 73(6):729-732, 1996.
Mounts et al., "Performance Evaluation of Hexane-Extracted Oils from Genetically Modified Soybeans," JAOCS, 71 (2):157-161, 1994.
Yan et al., "Extraction and Refining of Black Currant Seed Oil," China Oils and Fats, 29(2):1-5, 2004.

(56) References Cited

OTHER PUBLICATIONS

List et al., "Oxidation and Quality of Soybean Oil: A Preliminary Study of the Anisidine Test," JAOCS, 51:17-21, 1974.
Chu et al., "Factors Affecting the Content of Tocopherol in Soybean Oil," JAOCS, 70(12):1263-1268, 1993.
Neff et al., "Oxidative Stability of Natural and Randomized High-Palmitic- and High-Stearic-Acid Oils from Genetically Modified Soybean Varieties," JAOCS, 76(7):825-831, 1999.
Bhatia et al., "Oilseed cutivars developed from induced mutations and mutations altering fatty acid composition", Mutation Breeding Review, Dec. 1999, pp. 1-36, No. 11, Retrieved from Internet—http://mvgs.iaea.org/pdf/MBREV19991211.pdf.
Warner et al., "Effect of Fatty Acid Composition of Oils on Flavor and Stability of Fried Foods", JAOCS, 1997, p. 347-356, vol. 74(4).
Non-Final Office Action in Inter Partes Reexamination; filed Aug. 14, 2012; U.S. Appl. No. 95/002,028.
Comments by Third-Party Requester to Response to Non-Final Office Action in Inter Partes Reexamination; filed Nov. 14, 2012; U.S. Appl. No. 95/002028.
Non-Final Office Action in Inter Partes Reexamination; filed Dec. 7, 2012; U.S. Appl. No. 95/000,690.
2nd Declaration of Anthony John Kinney dated Sep. 11, 2012.
Invitation/Partial Search Report issued in analogous application No. PCT/US2005/039807 dated Apr. 7, 2006.
Rafalski, "Applications of Single Nucleotide Polymorphisms in Crop Genetics", Curr. Opin. in Plant Biol., (5): 94-100, 2002.
Rahman et al., "Inheritance of Reduced Linolenic Acid Content in Soybean Seed Oil", Theor. Appl. Genet., (94), 299-302, 1997.
Stojsin et al.,"Inheritance of Low Linolenic Acid Level in the Soybean Line RG10", Crop Sci., (38), 1441-1444, 1998.
Petition to Strike Under 37 CFR 1.182; filed Mar. 20, 2013; U.S. Appl. No. 95/002,309.
Comments by Third-Party Requester to Response to Non-Final Office Action in Inter Partes Reexamination; filed Mar. 11, 2013; U.S. Appl. No. 95/000,690.
Declaration of Anthony John Kinney dated Mar. 6, 2013; Inter Partes Reexamination; U.S. Appl. No. 95/000,690.
Zhang et al., "Effects of Expander Process on the Phospholipids in Soybean Oil", Journal of American Oil Chemist's Society, Oct. 1994, pp. 1145-1148, vol. 71, No. 10.
Notice of Defective Paper; filed Apr. 12, 2013; U.S. Appl. No. 95/002,309.
Corrected Comments by Third-Party Requester to Response to Non-Final Office Action in Inter Partes Reexamination; filed Apr. 23, 2013; U.S. Appl. No. 95/002,309.
Petition to Strike Under 37 CFR 1.182; filed Apr. 17, 2013; U.S. Appl. No. 95/000,690.
First Office Action (India) for PCT/US2007/063643 (WO2007/106728); filed Mar. 28, 2013.
Oilseed heptane extraction procedure from the Cyberlipid "Special Procedures" website. (No date is associated with this website).
Action Closing Prosecution; dated May 30, 2013; U.S. Appl. No. 95/002,028.
Response to Action Closing Prosecution; filed Jun. 28, 2013; U.S. Appl. No. 95/002,028.
About-Definition and More from the Free Merriam-Webster Dictionary. http://www.merriam-webster.com/dictionary/about, accessed Apr. 22, 2013.
Non-Final Office Action; dated May 24, 2013; U.S. Appl. No. 95/002,309.
Petition to Review Under 37 CFR1.181; filed May 14, 2013; U.S. Appl. No. 95/002,309.
Non-Final Office Action (Canada) for CA Patent No. 2,645,148 (WO2007/106728); dated May 7, 2013.
Office Action (Australia) for AU Application No. 2007226680 (WO2007/106728); dated Mar. 19, 2012.
Response to Office Action (Australia) for AU Application No. 2007226680 (WO2007/106728); filed May 2, 2013.
Response to Non-Final Office Action; dated Jul. 23, 2013; U.S. Appl. No. 95/002,309.
Response to Inter Partes Reexamination Non-Final Office Action Under 37 C.F.R 1.945 for U.S. Pat. No. 8,057,835, filed on Oct. 15, 2012.
2nd Declaration of Toni Voelker, Feb. 7, 2013, filed with response to Inter Partes Reexamination of U.S. Pat. No. 7,943,818; U.S. Appl. No. 95/000,690.
Response to Inter Partes Reexamination Non-Final Office Action Under 37 C.F.R 1.945 for U.S. Pat. No. 7,943,818, filed on Dec. 7, 2012.
Non-Final Office Action dated Oct. 11, 2012; U.S. Appl. No. 13/295,501.
Response to Non-Final Office Action dated Jan. 10, 2013; U.S. Appl. No. 13/295,501.
Non-Final Office Action dated Feb. 14, 2013; U.S. Appl. No. 13/295,501.
Non-Final Office Action dated Jan. 11, 2012; U.S. Appl. No. 13/080,087.
Response to Non-Final Office Action dated Apr. 10, 2012; U.S. Appl. No. 13/080,087.
Non-Final Office Action dated Jul. 5, 2012; U.S. Appl. No. 13/080,087.
Response to Non-Final Office Action dated Nov. 5, 2012; U.S. Appl. No. 13/080,087.
Final Office Action dated Feb. 22, 2013; U.S. Appl. No. 13/080,087.
Non-Final Office Action dated Aug. 30, 2012; U.S. Appl. No. 12/882,579.
Response to Non-Final Office Action dated Nov. 30, 2012; U.S. Appl. No. 12/882,579.
Comments by Third-Party Requester to Response to Non-Final Office Action in inter partes Reexamination; filed Jul. 29, 2013; U.S. Appl. No. 95/002,028.
Comments by Third-Party Requester to Response to Non-Final Office Action in Inter Partes Reexamination; filed Feb. 1, 2013; U.S. Appl. No. 95/002,309.
Extended European Search Report issued in analogous application No. EP 12193422.8 dated Jan. 21, 2013.
Notice of Defective Paper; filed Jul. 31, 2013; U.S. Appl. No. 95/002,309.
Response to the Notice of Defective Paper filed Aug. 16, 2013; U.S. Appl. No. 95/002,309.
Response dated Aug. 21, 2013 from USPTO to Petition to Review Under 37 CFR1.181; filed May 14, 2013; U.S. Appl. No. 95/002,309.
Office Action dated Apr. 29, 2010 for U.S. Appl. No. 12/320,692.
Final Office Action dated Nov. 9, 2010 for U.S. Appl. No. 12/320,692.
Office Action dated May 10, 2012 for U.S. Appl. No. 12/320,692.
Final Office Action dated Jan. 7, 2013 for U.S. Appl. No. 12/320,692.
Office Action dated May 16, 2013 for U.S. Appl. No. 12/320,692.
Kurki et al., "Oilseed Processing for Small-Scale Producers", ATTRA, 2008, pp. 1-16.
Cyberlipid Center/Analysis/Lipid Extraction/Oilseed processing as accessed on Sep. 9, 2013 at the website, <http://www.cyberlipid.org/extract/extr0001.htm>.
Comments by Third Party Requester to PTO and Patent Owner's Response in Inter Partes Reexamination under 37 C.F.R. Section 1.947, filed Sep. 13, 2013, U.S. Appl. No. 95/002,309.
Restriction Action dated Jul. 6, 2012; U.S. Appl. No. 12/882,579.
Final Office Action dated Mar. 29, 2013; U.S. Appl. No. 12/882,579.
Third Party Requester's Corrected Comments; filed Oct. 11, 2013; U.S. Appl. No. 95/000,690.
Corrected Response to Non-Final Action; filed Aug. 16, 2013; U.S. Appl. No. 95/002,309.
Third Party Requester's Comments; filed Sep. 13, 2013; U.S. Appl. No. 95/002,309.
Non-final Action Closing Prosecution; dated Nov. 1, 2013; U.S. Appl. No. 95/002,309.
Response to Non-Final Action Closing Prosecution; filed Nov. 30, 2013; U.S. Appl. No. 95/002,309.
Declaration of Toni Voelker dated Nov. 25, 2013; U.S. Appl. No. 95/002,309.

(56) References Cited

OTHER PUBLICATIONS

Third Party Requester's Comments; filed Dec. 27, 2013; U.S. Appl. No. 95/002,309.
Third Party Requester's Petition; filed Oct. 11, 2013; U.S. Appl. No. 95/000,690.
Brace et al., "Agronomic and Seed Traits of Soybean Lines with High Oleate Concentration", Crop Science, Mar.-Apr. 2011, pp. 534-541, vol. 51.
Right of Appeal Notice; dated Mar. 5, 2014; U.S. Appl. No. 95/002,028.
Action Closing Prosecution; dated Mar. 5, 2014; U.S. Appl. No. 95/000,690.
Anai et al., "Identification of Corresponding Genes for Three Low-?-Linolenic Acid Mutants and Elucidation of their Contribution to Fatty Acid Biosynthesis in Soybean Seed", Plant Science, 2005, pp. 1615-1623. vol. 168.
Bilyeu et al., Plant Genetics Meeting on Mechanisms of Genetic Variation, Oct. 22-26, 2003, Abstract, p. 50, XP009060561.
Bilyeu et al., 10th Biennial Conference of the Cellular and Molecular Biology of the Soybean, 2004.
Bilyeu et al., "Molecular Genetic Resources for Development of 1& Linolenic Acid Soybeans", Crop Science, 2006, p. 1913-1918, vol. 46.
Bilyeu et al., "Novel FAD3 Mutant Allele Combinations Produce Soybeans Containing 1% Linolenic Acid in the Seed Oil", Crop Science, 2011, p. 259-264, vol. 51.
Brummer et al., "Mapping the Fan Locus Controlling Linolenic Acid Content in Soybean Oil", Journal of Heredity, 1995, p. 245-247, vol. 86.
Fehr et al., "Inheritance of Reduced Linolenic Acid Content in Soybean Genotypes A16 and A17", Crop Science, 1992, p. 903-906, vol. 32.
Fehr et al., "Breeding for Modified Fatty Acid Composition in Soybean", Crop Science, 2007, p. S72-S87, vol. 47.
GenBank Accession No. AY204710, May 17, 2005.
GenBank Accession No. AY204711, May 17, 2005.
GenBank Accession No. AY204712, May 17, 2005.
Jourden et al., "Specific Molecular Marker of the Genes Controlling Linolenic Acid Content in Rapeseed", Theoretical Applied Genetics, 1996, p. 512-518, vol. 93.
Knutzon et al., "Modification of Brassica Seed Oil by Antisense Expression of a Stearoyl-Acyl Carrier Protein Desaturase Gene", Proceedings of the National Academy of Sciences, 1992, p. 2624-2628. vol. 89.
Liu et al., "Oxidative Stability of Soybean Oils with Altered Fatty Acid Compositions", Journal of the American Oil Chemists Society, 1992, p. 528-532, vol. 69.
McBride, Back-to-Basics Breeding, USDA, Mar. 27, 2000.
O'Brien, Fats and oils: Formulating and processing for applications: 2003. p. 14-15, CRC Press.
Primomo et al., "Inheritance and Interaction of Low Palmitic and Low Linolenic Soybean", Crop Science, 2002, p. 31-36, vol. 42.
Primomo et al., "Genotype x Environment Interactions, Stability, and Agronomic Performance of Soybean with Altered Fatty Acid Profiles", Crop Science, 2002, p. 37-44, vol. 42.
Rahman et al., "Gentic Relationships of Soybean Mutants for Different Linolenic Acid Contents", Crop Science, 1998, p. 702-706, vol. 38.
Rajcan et al., "Detection of Molecular Markers Associated with Linolenic and Erucic Acid Levels in Spring Rapeseed (*Brassica napur* L.)", Euphytica, 1999, p. 173-181, vol. 105.
Reinprecht et al., "Molecular Basis of the Low Linolenic Acid Trait in Soybean EMS Mutant Line RG10", Plant Breading, 2009, p. 253-258, vol. 128.
Rennie et al., "New Allele at the Fan Locus in the Soybean Line A5", Crop Science, 1991, p. 297-301, vol. 31.
Walker et al., "Reduced-Linolenate Content Associations with Agronomic and Seed Traits of Soybean", Crop Science, 1998, p. 352-355, vol. 38.

Wilcox et al., "Relationships Between the Fan Allele and Agronomic Traits in Soybean", Crop Science, 1993, p. 87-89, vol. 33.
Wilcox et al., "Gene Symbol Assigned for Linolenic Acid Mutant in the Soybean" Journal of Heredity, 1987, p. 410, vol. 78.
Wilson, Essential Fatty Acids and Eicosanoids, 2003, p. 53-55, Yongsheng Huang, Shing Shyong XP049169197.
Yadav et al., "Cloning of Higher Plant ?-3 Fatty Acid Desaturases" Plant Physiology, 1993, p. 467-476, vol. 103.
Asgrow Announces New 2002 Soybean Varieties, Seed Today, 2001.
Asgrow Introduces 15 New Bean Varieties, High Plain Journal; 2003.
Dubois et al., "Fatty Acid Profiles of 80 Vegetable Oils with Regard to Their Nutritional Potential", European Journal of Science and Technology, 2007, pp. 710-732, vol. 109.
Buhr, "Ribozyme Termination of RNA Transcripts Down-Regulate Seed Fatty Acid Genes in Transgenic Soybean", Plant Journal, 2002, pp. 155-163, vol. 30, No. 2.
Burton et al., "Registration of 'Soyola' Soybean", Crop Science, Mar.-Apr. 2004, pp. 687-688.
Byrum et al., "Alteration of the Omega-3 Fatty Acid Desaturase Gene is Associated With Reduced Linolenic Acid in the A5 Soybean Genotype", Theoretical and Applied Genetics, 1997, pp. 356-359, vol. 94, Springer-Verlag.
Extended European Search Report for EP Application 07758217.9 dated Apr. 8, 2010.
Fehr et al., "Breeding for Fatty Acid Composition of Soybean Oil", VII World Soybean Research Conference, IV International Soybean Processing and Utilization Conference, III Congresso Mundial de Soja (Brazilian Soybean Congress, Proceedings, Feb. 29-Mar. 5, 2004, pp. 815-821.
Hawkins et al., "Characterization of Acyl-ACP Thioesterases of Mangosteen (Garcinia mangostana) Seed and High Levels of Stearate Production in Transgenic Canola", The Plant Journal, 1988, pp. 743-752, vol. 13, Issue 6.
International Search Report and Written Opinion for PCT/US2007/063643 dated Oct. 10, 2008.
Jaworski, "Industrial Oils From Transgenic Plants", Current Opinion in Plant Biology, 2003, pp. 178-184, vol. 6.
Kinney et al., "Designer Oils: The High Oleic Acid Soybean", Genetic Modification in the Food Industry, date unknown, pp. 193-213.
Ross et al., "Agronomic and Seed Traits of 1% Linolenate Soybean Genotypes", Crop Science, Mar.-Apr. 2000, pp. 383-386, vol. 40.
Singh, "Metabolic Engineering of New Fatty Acids in Plants", Current Opinion in Plant Biology, 2005, pp. 197-203, vol. 8.
Stoutjesdijk et al., "hpRNA-Mediated Targeting of the Arabidopsis FAD2 Gene Gives Highly Efficient and Stable Silencing", Plant Physiology, Aug. 1, 2002, pp. 1723-1731, vol. 129, American Society of Plant Physiologists, Rockville, MD, US.
Thomas et al., "Size Constraints for Targeting Post-Transcriptional Gene Silencing and for RNA-Directed Methylation in Nicotiana benthamiana Using a Potato Virus X Vector", The Plant Journal, Feb. 1, 2001, pp. 417-425, vol. 25, No. 4, Blackwell Scientific Publications, Oxford, GB.
Wilcox et al., "Inheritance of Low Linolenic Acid Content of the Seed of a Mutant of Glycine Max", Theoretical and Applied Genetics, 1985, pp. 74-78, vol. 71.
Rahman et al., "Combing Ability in Loci for High Oleic and Low Linolenic Acids in Soybean", Crop Science, 2001, vol. 41, pp. 26-29.
Gryson et al., "Detection of DNA During the Refining of Soybean Oil", Journal of the American Oil Chemists' Society, 2002, pp. 171-174, vol. 79, No. 2.
Wen et al., "Qualitative Detection for Genetically Modified Organisms in Edible Oils by PCR", Chinese Oils, 2002, 7 pages, vol. 27, Issue 2 (English translation and Chinese publication included).
Request for Continued Examination filed in U.S. Appl. No. 11/953,108 dated Sep. 5, 2011, application assigned to E.I. du Pont de Nemours and Company, 14 pages.
Declaration of Dr. Anthony John Kinney, Jun. 15, 2012 in support of the Booth patent, filed in connection with Reexamination Requests for U.S. Pat. Nos. 7,790,953, and 7,943,818.

(56) References Cited

OTHER PUBLICATIONS

Toni Voelker, et al., "Variations in the Biosynthesis of Seed-Through Storage Lipids", Annu. Rev. Plant Physiol. Plant Mol. Biol. 2001, 52:335-61.
Ackman, "Flame Ionization Detection Applied to Thin-Layer Chromatography on Coated Quartz Rods", Methods in Enzymology, 1981, p. 205-252, vol. 72.
Bilyeu et al., "Three Microsomal Omega-3 Fatty-acid Desaturase Genes Contribute to Soybean Linolenic Acid Levels", Crop Science, 2003, p. 1833-1838, vol. 43.
Christie, Gas Chromatography and Lipids, 1989 (Reprinted 1990), The Oily Press.
Hermansson et al., "Automated Quantitative Analysis of Complex Lipidomes by Liquid Chromatography/Mass Spectrometry", Anal. Chem., 2005, p. 2166-2175, vol. 77.
Lee et al., "Targeted Lipidomics Using Electron Capture Atmospheric Pressure Chemical Ionization Mass Spectrometry", Rapid Communications in Mass Spectrometry, 2003, p. 2168-2176, vol. 17.
Declaration of Dr. Anthony John Kinney, Sep. 11, 2012 in support of prior art references, filed in connection with reexamination request for U.S. Pat. No. 7,943,818.
Request for Inter Partes Reexamination of U.S. Pat. No. 7,943,818 filed by E.I. du Pont de Nemours and Company.
Request for Inter Partes Reexamination of U.S. Pat. No. 7,790,953 filed by E.I. du Pont de Nemours and Company.
Response to Inter Partes Reexamination Non-Final Office Action Under 37 C.F.R 1.945 for U.S. Pat. No. 7,790,953, filed on Oct. 15, 2012.
Declaration of Jay M. Harrison, Oct. 15, 2012, filed with response to Inter Partes Reexamination of U.S. Pat. No. 7,790,953.
Declaration of Toni Voelker, Oct. 15, 2012, filed with response to Inter Partes Reexamination of U.S. Pat. No. 7,790,953.
Rennie et al., "Fatty Acid Composition of Oil from Soybean Seeds Grown at Extreme Temperatures", Journal of the American Oil Chemist's Society, Nov. 1989, pp. 1622-1624, vol. 66, No. 11.
Chu, "A Comparative Study of Analytical Methods for Evaluation of Soybean Oil Quality", Journal of the American Oil Chemist's Society, Jun. 1991, pp. 379-384, vol. 68, No. 6.
Decision on Reexamination Request and Non-Final Office Action in Inter Partes Reexamination; dated Nov. 1, 2012; U.S. Appl. No. 95/002,309.
Request for Inter Partes Reexamination; U.S. Pat. No. 8,057,835; filed Sep. 14, 2012; U.S. Appl. No. 95/002,309.
Liu et al., "Soybean Phospholipids", Recent Trends for Enhancing the Diversity and Quality of Soybean Products (Chapter 22), Oct. 2011, pp. 483-500, Published by InTech.
Webster's Ninth New Collegiate Dictionary, p. 1129, 1986.
Declaration of Dr. Anthony John Kinney, Sep. 12, 2012 in support of prior art references, filed in connection with reexamination request for U.S. Pat. No. 8,057,835.
Warner et al., Frying Quality and Stability of Low- and Ultra-Low-Linolenic Acid Soybeans Oils, JAOCS, 80 (3)3)275-280, 2003.
Asoyia, Innovative Soybean Oil Offers Health, Cooking, and Taste Benefits, News Release, www.asoyia.com, Oct. 14, 2004, p. 1-3.
Health Canada, Novel Food Information, Low Linolenic Soybean (OT96-15) Apr. 2001, p. 1-3.
Iowa State University, About 1% Linolenic Soybean Oil, product brochure, www.notrans.iastate.edu/about.html.
Dow Agrosciences, Natreon Canola Oil, product brochure, www.dowagro.com/natreon/canola/index.htm.
Dow Agrosciences, Natreon Canola Oil, Natreon History, product brochure, www.dowagro.com/natreon/canola/history.htm.
Dow Agrosciences, Natreon Canola Oil, Natreon vs. Other Oils, product brochure, www.dowagro.com/natreon/canola/oils.htm.
Cargill, Odyssey, 95 High Stability Canola Oil, Zero Trans Fat High Stability Oil., product brochure, www.clearvalleyoils.com.
Su et al., Oxidative and Flavor Stabilities of Soybean Oils and Low- and Ultra-Low-Linolenic Acid Composition, JAOCS, 80(2):171-176, 2003.
Asoyia, Ultra Low Lin Soybean Oil, product brochure, www.asoyia.com, Oct. 21, 2004, p. 1-2.
Cargill, Clear Valley, High Oleic Sunflower Oil, Zero Trans Fat Oil. High Oxidative Stability. All Natural, product brochure, www.clearvalleyoils.com.
Cargill, Clear Valley 75, High Oleic Canola Oil, Zero Trans Fat Oil. High Stability. Fresh Flavor. Long Product Shelf Life. Product brochure, www.clearvalleyoils.com.

\* cited by examiner

SOYBEAN SEED AND OIL COMPOSITIONS AND METHODS OF MAKING SAME

CROSS-REFERENCE TO RELATED APPLICATIONS

This application is a continuation of U.S. patent application Ser. No. 14/085,933, filed Nov. 21, 2013 and incorporated herein by reference in its entirety, which is a divisional of U.S. patent application Ser. No. 13/669,024, filed Nov. 5, 2012 and herein incorporated by reference in its entirety, which is a divisional of U.S. patent application Ser. No. 13/080,087, filed Apr. 5, 2011 and incorporated herein by reference in its entirety, which is a continuation of U.S. patent application Ser. No. 12/713,388, now U.S. Pat. No. 7,943,818, filed Feb. 26, 2010 and incorporated herein by reference in its entirety, which is a division of U.S. patent application Ser. No. 11/684,413, now U.S. Pat. No. 7,790,953, filed Mar. 9, 2007, which claims the benefit of U.S. Provisional Patent Application No. 60/781,519, filed Mar. 10, 2006, both of which are herein incorporated by reference in their entireties.

STATEMENT REGARDING FEDERALLY SPONSORED RESEARCH OR DEVELOPMENT

Not Applicable.

APPENDIX

Not Applicable.

INCORPORATION OF SEQUENCE LISTING

A text file of the Sequence Listing contained in the file named "54449_Seq_listing_ST25.txt" which is 74,628 bytes (measured in MS-Windows®) in size and which was created on Jan. 7, 2016, is electronically filed herewith and is incorporated by reference in its entirety. This Sequence Listing consists of SEQ ID NO:1-65.

BACKGROUND OF THE INVENTION

1. Field of the Invention

This invention relates generally to methods of making soybean plants that produce soybean seed with altered oil compositions and, more particularly, to methods where soybean seed with a mid oleic, low linolenic phenotype or soybean seed with a mid oleic, low saturate, low linolenic phenotype are produced.

2. Related Art

Plant oils are used in a variety of applications. Novel vegetable oil compositions and improved approaches to obtain oil compositions, from biosynthetic or natural plant sources, are needed. Depending upon the intended oil use, various different fatty acid compositions are desired. Plants, especially species which synthesize large amounts of oils in seeds, are an important source of oils both for edible and industrial uses. Seed oils are composed almost entirely of triacylglycerols in which fatty acids are esterified to the three hydroxyl groups of glycerol.

Soybean oil typically contains about 16-20% saturated fatty acids: 13-16% palmitate and 3-4% stearate. See generally Gunstone et al., The Lipid Handbook, Chapman & Hall, London (1994). Soybean oils have been modified by various breeding methods to create benefits for specific markets. However, a soybean oil that is broadly beneficial to major soybean oil users such as consumers of salad oil, cooking oil and frying oil, and industrial markets such as biodiesel and biolube markets, is not available. Prior soybean oils were either too expensive or lacked an important food quality property such as oxidative stability, good fried food flavor or saturated fat content, or an important biodiesel property such as appropriate nitric oxide emissions or cold tolerance or cold flow.

Higher plants synthesize fatty acids via a common metabolic pathway—the fatty acid synthetase (FAS) pathway, which is located in the plastids. β-ketoacyl-ACP synthases are important rate-limiting enzymes in the FAS of plant cells and exist in several versions. β-ketoacyl-ACP synthase I catalyzes chain elongation to palmitoyl-ACP (C16:0), whereas β-ketoacyl-ACP synthase II catalyzes chain elongation to stearoyl-ACP (C18:0). β-ketoacyl-ACP synthase IV is a variant of β-ketoacyl-ACP synthase II, and can also catalyze chain elongation to 18:0-ACP. In soybean, the major products of FAS are 16:0-ACP and 18:0-ACP. The desaturation of 18:0-ACP to form 18:1-ACP is catalyzed by a plastid-localized soluble delta-9 desaturase (also referred to as "stearoyl-ACP desaturase"). See Voelker et al., 52 Annu. Rev. Plant Physiol. Plant Mol. Biol. 335-61 (2001).

The products of the plastidial FAS and delta-9 desaturase, 16:0-ACP, 18:0-ACP, and 18:1-ACP, are hydrolyzed by specific thioesterases (FAT). Plant thioesterases can be classified into two gene families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). Such thioesterases have an important role in determining chain length during de novo fatty acid biosynthesis in plants, and thus these enzymes are useful in the provision of various modifications of fatty acyl compositions, particularly with respect to the relative proportions of various fatty acyl groups that are present in seed storage oils.

The products of the FATA and FATB reactions, the free fatty acids, leave the plastids and are converted to their respective acyl-CoA esters. Acyl-CoAs are substrates for the lipid-biosynthesis pathway (Kennedy Pathway), which is located in the endoplasmic reticulum (ER). This pathway is responsible for membrane lipid formation as well as the biosynthesis of triacylglycerols, which constitute the seed oil. In the ER there are additional membrane-bound desaturases, which can further desaturate 18:1 to polyunsaturated fatty acids. A delta-12 desaturase (FAD2) catalyzes the insertion of a double bond into 18:1 (oleic acid), forming linoleic acid (18:2). A delta-15 desaturase (FAD3) catalyzes the insertion of a double bond into 18:2, forming linolenic acid (18:3).

Inhibition of the endogenous FAD2 gene through use of transgenes that inhibit the expression of FAD2 has been shown to confer a desirable mid-oleic acid (18:1) phenotype (i.e. soybean seed comprising about 50% and 75% oleic acid by weight). Transgenes and transgenic plants that provide for inhibition of the endogenous FAD2 gene expression and a mid-oleic phenotype are disclosed in U.S. Pat. No. 7,067,722. In contrast, wild type soybean plants that lack FAD2 inhibiting transgenes typically produce seed with oleic acid compositions of less than 20%.

Soybean oil typically contains about 8% of linolenic acid (18:3) that results in reduced stability and flavor. The levels of linolenic acid (18:3) in soybean oil can be reduced by hydrogenation to improve both stability and flavor (Dutton et al., 1951; Lui and White, 1992). Unfortunately, hydrogenation results in the production of trans fatty acids, which increases the risk for coronary heart disease when consumed (Hu et al., 1997).

Conventional breeding has also been used to generate soybean lines with the linolenic levels ranging from 1%-6% (Ross et al. Crop Science, 40:383; 2000; Wilson et al. J. Oleo Sci., 50:5, 87, 2001; Wilson Lipid technology September 1999). Varieties of low linolenic acid soybean have been produced through mutation, screening and breeding (Fehr et al., 1992; Rahman and Takagi, 1997; Ross et al., 2000; Byrum et al., 1997; Stoisin et al., 1998). Certain soybean varieties with a linolenic acid content of about 1% or lower have been obtained (U.S. Pat. Nos. 5,534,425 and 5,714,670). More recently, methods for obtaining soybean plants with both low levels of linolenic acid levels as well as the yield and growth characteristics of agronomically elite soybean varieties have been disclosed (U.S. Patent Application 2006/0107348).

Oleic acid has one double bond, but is still relatively stable at high temperatures, and oils with high levels of oleic acid are suitable for cooking and other processes where heating is required. Recently, increased consumption of high oleic oils has been recommended, because oleic acid appears to lower blood levels of low density lipoproteins ("LDLs") without affecting levels of high density lipoproteins ("HDLs"). However, some limitation of oleic acid levels is desirable, because when oleic acid is degraded at high temperatures, it creates negative flavor compounds and diminishes the positive flavors created by the oxidation of linoleic acid. Neff et al., JAOCS, 77:1303-1313 (2000); Warner et al., J. Agric. Food Chem. 49:899-905 (2001). It is thus preferable to use oils with oleic acid levels that are 65-85% or less by weight, in order to limit off-flavors in food applications such as frying oil and fried food. Other preferred oils have oleic acid levels that are greater than 55% by weight in order to improve oxidative stability.

For many oil applications, saturated fatty acid levels of less than 8% by weight or even less than about 2-3% by weight are desirable. Saturated fatty acids have high melting points which are undesirable in many applications. When used as a feedstock or fuel, saturated fatty acids cause clouding at low temperatures, and confer poor cold flow properties such as pour points and cold filter plugging points to the fuel. Oil products containing low saturated fatty acid levels may be preferred by consumers and the food industry because they are perceived as healthier and/or may be labeled as "saturated fat free" in accordance with FDA guidelines. In addition, low saturate oils reduce or eliminate the need to winterize the oil for food applications such as salad oils. In biodiesel and lubricant applications oils with low saturated fatty acid levels confer improved cold flow properties and do not cloud at low temperatures.

Soybean lines that produce seed with mid-oleic, low-linolenic acid content would be very desirable. Unfortunately, attempts to combine the mid oleic and low linolenic traits via genetic engineering approaches have been problematic. Transgenic lines where both the delta-12 desaturase (FAD2) and the delta-15 desaturase (FAD3) genes have been suppressed have seed with low linolenic levels, but the oleic acid levels are typically above the range defined for mid oleic. However, the methods disclosed here enable production of low linolenic soybean seeds that also have oleic acid levels in the mid oleic range of 55-80%. Furthermore, these methods do not entail hydrogenation processes and thus avoid the production of undesirable trans-fats.

Soybean lines that produce seed with mid-oleic, low saturate, low-linolenic acid content would be also very desirable. Methods disclosed here enable production of low linolenic soybean seeds that also have oleic acid levels in the mid oleic range of 55-80% and saturated fatty acid levels of less than 8%.

SUMMARY OF THE INVENTION

It is in view of the above problems that the present invention was developed. The invention first relates to a method of producing a soybean plant comprising a linolenic acid content of less than about 6% of total seed fatty acids by weight and an oleic acid content of about 55% to about 80% of total seed fatty acids by weight. This method of the invention is practiced by a first step of making one or more soybean plants that comprise a transgene that decreases the expression of an endogenous soybean FAD2-1 gene and at least one loss-of-function mutation in an endogenous soybean FAD3 gene, a second step of obtaining at least one seed from said soybean plant obtained from the first step, a third step of determining a percentage of the total seed fatty acid content by weight of linolenic acid and oleic acid for the seed from the second step, and then identifying a soybean plant that yields seed having a seed fatty acid composition comprising a linolenic acid content of less than about 6% of total seed fatty acids by weight and an oleic acid content of about 55% to about 80% of total seed fatty acids by weight.

In other embodiments of this method, the soybean plants that are made in the first step comprise at least two loss of function mutations in at least two endogenous soybean FAD3 genes. These loss of function mutations can be located in the endogenous soybean FAD3-1B and FAD3-1C genes. In this embodiment of the method, the soybean plants identified in the third step of the method comprise a linolenic acid content of less than about 3% of total seed fatty acids by weight and an oleic acid content of about 55% to about 80% of total seed fatty acids by weight.

In certain embodiments of this method, the transgene can further comprise a transgene that confers herbicide tolerance. The herbicide tolerance transgene may confer tolerance to glyphosate. In specific embodiments of the invention, the transgene comprises sequences located between the T-DNA border sequences of pMON68504, pCGN5469, pCGN5471, or pCGN5485 that are integrated into a chromosome of said plant.

In the third step of the method, the percentage of the total seed fatty acid content by weight of linolenic acid and oleic acid is determined by a lipid analysis technique. This lipid analysis technique comprises one or more techniques selected from the group consisting of gas chromatography/flame ionization detection, gas chromatography/mass spectroscopy, thin layer chromatography/flame ionization detection, liquid chromatography/mass spectrometry, liquid chromatography/electrospray ionization-mass spectrometry and liquid chromatography/electrospray ionization-tandem mass spectroscopy.

The soybean plant comprising a transgene that decreases the expression of an endogenous soybean FAD2-1 gene and at least one loss-of-function mutation in an endogenous soybean FAD3 gene can be made by crossing a first soybean parent line comprising the transgene with a second soybean parent line comprising at least one loss-of-function mutation in an endogenous soybean FAD3 gene to obtain an F1 soybean plant that is heterozygous for the transgene and heterozygous for at least one loss of function mutation in a FAD3 gene and then selfing F1 progeny plants from the cross to obtain an F2 soybean plant that is homozygous for said transgene and homozygous for at least one loss of function mutation in a FAD3 gene. In certain embodiments of this method, the second soybean parent line comprises at least two loss of function mutations in at least two endogenous soybean FAD3 genes. The two endogenous soybean FAD3 genes can be FAD3-1B and FAD3-1C. In this method, the F1 soybean plant that is heterozygous for the transgene and for at least one loss of function mutation in a FAD3 gene is obtained in step (i) by subjecting a plurality of F1 plants to at least one DNA analysis technique permitting identification of an F1 plant that is heterozygous for said transgene and for at least one loss of function mutation in a FAD3 gene. Similarly, the F2 soybean plant that is homozygous for the transgene and homozygous for at least one loss of function mutation in a FAD3 gene is obtained in step (ii) by subjecting a plurality of F2 plants to at least one DNA analysis technique permitting identification of an F2 plant that is homozygous for said transgene and homozygous for at least one loss of function mutation in a FAD3 gene. The DNA analysis technique comprises one or more techniques selected from the group consisting of PCR analysis, quantitative PCR analysis, SNP analysis, AFLP analysis, RFLP analysis and RAPD analysis. In certain embodiments of this invention, the DNA analysis technique comprises detection of at least one single nucleotide polymorphism at a position in the FAD3-1C gene sequence corresponding to nucleotide 687, 1129, 1203, 2316, 3292, 3360 or 3743 of SEQ ID NO:62, detection of a deletion in the FAD3-1C gene of SEQ ID NO:62, or detection of at least one single nucleotide polymorphism in a soybean FAD3-1C promoter sequence corresponding to a guanine at nucleotide 334, a cytosine at nucleotide 364, a thymine at nucleotide 385, an adenine at nucleotide 387, a cytosine at nucleotide 393, a guanine at nucleotide 729 and a cytosine at nucleotide 747 of SEQ ID NO:63. In other embodiments of this invention, the DNA analysis technique comprises detection of a single nucleotide polymorphism in a soybean FAD3-1B gene comprising a substitution of a thymine residue for a cytosine residue at a position in the FAD3-1b gene sequence corresponding to nucleotide 2021 of SEQ ID NO:61. In this method, the transgene can further comprise a transgene that confers herbicide tolerance and the F1 soybean plant that is heterozygous for said transgene is obtained in step (i) by subjecting a plurality of F1 plants to herbicide selection for said transgene. Similarly, when the transgene further comprises a transgene that confers herbicide tolerance, a plurality of F2 plants enriched for F2 soybean plants that are homozygous for said transgene are obtained in step (ii) by subjecting said plurality of F2 plants to herbicide selection for said transgene. This method can also further comprise the step iii) of selfing the F2 progeny plant that are homozygous for the transgene and homozygous for at least one loss of function mutation in a FAD3 gene from step (ii) to obtain an F3 soybean plant.

An alternative method of making soybean plants that comprise a transgene that decreases the expression of an endogenous soybean FAD2-1 gene and at least one loss-of-function mutation in an endogenous soybean FAD3 gene involves direct transformation of soybean plants or cells comprising the mutation with the transgene. Thus this soybean plant is made in the first step of the invention by transforming a soybean plant or plant cell comprising at least one loss-of-function mutation in an endogenous soybean FAD3 gene with a transgene that decreases the expression of endogenous soybean FAD2-1 gene to obtain an R0 soybean plant with least one loss of function mutation in a FAD3 gene that is heterozygous for said transgene, selfing the R0 progeny plant from the previous step to obtain an R1 soybean plant that is homozygous for the transgene and homozygous for at least one loss of function mutation in a FAD3 gene, thereby obtaining a soybean plant comprising a transgene that decreases the expression of an endogenous soybean FAD2-1 gene and at least one loss-of-function mutation in an endogenous soybean FAD3 gene. In certain embodiments of this method, the transgene further comprises sequences that confer a herbicide tolerance trait. In other embodiments of the invention, the transgene further comprises sequences that confer glyphosate tolerance.

This invention also encompasses soybean plants produced by the aforementioned methods of the invention as well as plant parts of soybean plants produced by the methods of the invention. The soybean plant part produced can be pollen, an ovule, a meristem, a leaf, a stem, a root, or a cell. Progeny soybean plants from the soybean plants produced by these methods are also contemplated by this invention. The invention also encompasses seed of the soybean plant produced by the methods of the invention, where this seed has a fatty acid composition comprising a linolenic acid content of less than about 6% of total seed fatty acids by weight and an oleic acid content of about 55% to about 80% of total seed fatty acids by weight. The invention further encompasses seed of the soybean plant produced by methods wherein soybean plants comprising at least two loss of function mutations in at least two endogenous soybean FAD3 genes are used, said seed having a fatty acid composition comprising a linolenic acid content of less than about 3% of total seed fatty acids by weight and an oleic acid content of about 55% to about 80% of total seed fatty acids by weight.

This invention also provides a method of obtaining a soybean plant with an altered seed oil fatty acid composition comprising the steps of: a) crossing a first soybean parent line having a seed oil fatty acid composition comprising a linolenic acid content of less than about 3% of total fatty acids by weight with a second soybean parent line having a seed oil fatty acid composition wherein the content of at least one fatty acid other than linoleic acid is altered by at least 50% when compared to the corresponding fatty acid content of a commodity soybean oil, said second soybean parent line comprising a transgene that alters the content of at least one fatty acid other than linoleic acid; and b) obtaining a progeny plant exhibiting a seed oil fatty acid composition comprising a linolenic acid content of less than 3% of total fatty acids by weight and a content of at least one fatty acid other than linoleic acid that is altered by at least 50% when compared to the corresponding fatty acid content of a commodity soybean oil, thereby obtaining a soybean plant with an altered seed oil fatty acid composition. In this method, the fatty acid other than linolenic acid is selected from the group consisting of lauric acid, myristic acid, palmitic acid, stearic acid, stearidonic acid, oleic acid, linoleic acid, γ-linoleic acid, eicosapentaenoic acid and docosahexaenoic acid.

The invention also relates to a method of producing a soybean plant comprising a linolenic acid content of less than about 6% of total seed fatty acids by weight, a saturated fatty acid content of less than about 8% by weight and an oleic acid content of about 55% to about 80% of total seed fatty acids by weight. This method of the invention is practiced by a first step of making one or more soybean plants that comprise at least one transgene that decreases the expression of both an endogenous soybean FAD2-1 and an endogenous FATB gene, and at least one loss-of-function mutation in an endogenous soybean FAD3 gene, a second step of obtaining at least one seed from said soybean plant obtained from the first step, a third step of determining a percentage of the total seed fatty acid content by weight of linolenic acid, saturated fatty acids and oleic acid for the seed from the second step, and then identifying a soybean plant that yields seed having a seed fatty acid composition comprising a linolenic acid content of less than about 6% of total seed fatty acids by weight, a saturated fatty acid content of less than about 8% by weight and an oleic acid content of about 55% to about 80% of total seed fatty acids by weight.

In other embodiments of this method, the soybean plants that are made in the first step comprise at least two loss of function mutations in at least two endogenous soybean FAD3 genes. These loss of function mutations can be located in the endogenous soybean FAD3-1B and FAD3-1C genes. In this embodiment of the method, the soybean plants identified in the third step of the method can comprise a linolenic acid content of less than about 3% of total seed fatty acids by weight, a saturated fatty acid content of less than about 8% by weight and an oleic acid content of about 55% to about 80% of total seed fatty acids by weight.

In certain embodiments of this method, the transgene can further comprise a transgene that confers herbicide tolerance. The transgene can confer tolerance to glyphosate. The transgene that confers resistance to glyphosate can encode a CP4 EPSPS gene.

In the third step of the method, the percentage of the total seed fatty acid content by weight of linolenic acid, saturated fatty acids and oleic acid is determined by a lipid analysis technique. This lipid analysis technique comprises one or more techniques selected from the group consisting of gas chromatography/flame ionization detection, gas chromatography/mass spectroscopy, thin layer chromatography/flame ionization detection, liquid chromatography/mass spectrometry, liquid chromatography/electrospray ionization-mass spectrometry and liquid chromatography/electrospray ionization-tandem mass spectroscopy.

The soybean plant comprising at least one transgene that decreases the expression of both an endogenous soybean FAD2-1 and an endogenous FATB gene and at least one loss-of-function mutation in an endogenous soybean FAD3 gene can be made by crossing a first soybean parent line comprising the transgene with a second soybean parent line comprising at least one loss-of-function mutation in an endogenous soybean FAD3 gene to obtain an F1 soybean plant that is heterozygous for the transgene(s) and heterozygous for at least one loss of function mutation in a FAD3 gene and then selfing F1 progeny plants from the cross to obtain an F2 soybean plant that is homozygous for said transgene and homozygous for at least one loss of function mutation in a FAD3 gene. In certain embodiments of this method, the second soybean parent line comprises at least two loss of function mutations in at least two endogenous soybean FAD3 genes. The two endogenous soybean FAD3 genes can be FAD3-1B and FAD3-1C. In this method, the F1 soybean plant that is heterozygous for the transgene and for at least one loss of function mutation in a FAD3 gene is obtained in step (i) by subjecting a plurality of F1 plants to at least one DNA analysis technique permitting identification of an F1 plant that is heterozygous for said transgene and for at least one loss of function mutation in a FAD3 gene. Similarly, the F2 soybean plant that is homozygous for the transgene and homozygous for at least one loss of function mutation in a FAD3 gene is obtained in step (ii) by subjecting a plurality of F2 plants to at least one DNA analysis technique permitting identification of an F2 plant that is homozygous for said transgene and homozygous for at least one loss of function mutation in a FAD3 gene. The DNA analysis technique comprises one or more techniques selected from the group consisting of PCR analysis, quantitative PCR analysis, SNP analysis, AFLP analysis, RFLP analysis and RAPD analysis. In certain embodiments of this invention, the DNA analysis technique comprises detection of at least one single nucleotide polymorphism at a position in the FAD3-1C gene sequence corresponding to nucleotide 687, 1129, 1203, 2316, 3292, 3360 or 3743 of SEQ ID NO:62, detection of a deletion in the FAD3-1C gene of SEQ ID NO:62, or detection of at least one single nucleotide polymorphism in a soybean FAD3-1C promoter sequence corresponding to a guanine at nucleotide 334, a cytosine at nucleotide 364, a thymine at nucleotide 385, an adenine at nucleotide 387, a cytosine at nucleotide 393, a guanine at nucleotide 729 and a cytosine at nucleotide 747 of SEQ ID NO:63. In other embodiments of this invention, the DNA analysis technique comprises detection of single nucleotide polymorphism in a soybean FAD3-1B gene comprising a substitution of a thymine residue for a cytosine residue at a position in the Fad3-1b gene sequence corresponding to nucleotide 2021 of SEQ ID NO:61. In this method, the transgene can further comprise a transgene that confers herbicide tolerance and the F1 soybean plant that is heterozygous for said transgene is obtained in step (i) by subjecting a plurality of F1 plants to herbicide selection for said transgene. Similarly, when the transgene further comprises a transgene that confers herbicide tolerance, a plurality of F2 plants enriched for F2 soybean plants that are homozygous for said transgene are obtained in step (ii) by subjecting said plurality of F2 plants to herbicide selection for said transgene. This method can also further comprise the step iii) of selfing the F2 progeny plant that are homozygous for the transgene and homozygous for at least one loss of function mutation in a FAD3 gene from step (ii) to obtain an F3 soybean plant.

An alternative method of making soybean plants that comprise at least one transgene that decreases the expression of both an endogenous soybean FAD2-1 and an endogenous soybean FATB gene and an endogenous FATB gene and at least one loss-of-function mutation in an endogenous soybean FAD3 gene involves direct transformation of soybean plants or cells comprising the mutation with the transgene(s). Thus this soybean plant is made in the first step of the invention by transforming a soybean plant or plant cell comprising at least one loss-of-function mutation in an endogenous soybean FAD3 gene with one or more transgene(s) that decrease the expression of both an endogenous soybean FAD2-1 and an endogenous soybean FATB gene to obtain an R0 soybean plant with least one loss of function mutation in a FAD3 gene that is heterozygous for said transgene, selfing the R0 progeny plant from the previous step to obtain an R1 soybean plant that is homozygous for the transgene and homozygous for at least one loss of function mutation in a FAD3 gene, thereby obtaining a soybean plant comprising a transgene that decreases the expression of an endogenous soybean FAD2-1 gene and at least one loss-of-function mutation in an endogenous soybean FAD3 gene. In certain embodiments of this method, the transgene further comprises sequences that confer a herbicide tolerance trait. In other embodiments of the invention, the transgene further comprises sequences that confer glyphosate tolerance.

This invention also encompasses soybean plants produced by the aforementioned methods of the invention as well as plant parts of soybean plants produced by the methods of the invention. The soybean plant part produced can be pollen, an ovule, a meristem, a leaf, a stem, a root, or a cell. Progeny soybean plants from the soybean plants produced by these methods are also contemplated by this invention. The invention also encompasses seed of the soybean plant produced by the methods of the invention, where this seed has a fatty acid composition comprising a linolenic acid content of less than about 6% of total seed fatty acids by weight, a saturated fatty acid content of less than 8% by weight and an oleic acid content of about 55% to about 80% of total seed fatty acids by weight. The invention further encompasses seed of the soybean plant produced by methods wherein soybean plants comprising at least two loss of function mutations in at least two endogenous soybean FAD3 genes are used, said seed having a fatty acid composition comprising a linolenic acid content of less than about 3% of total seed fatty acids by weight, a saturated fatty acid content of less than 8% by weight and an oleic acid content of about 55% to about 80% of total seed fatty acids by weight.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE INVENTION

Description of the Nucleic Acid Sequences

Figure 1:
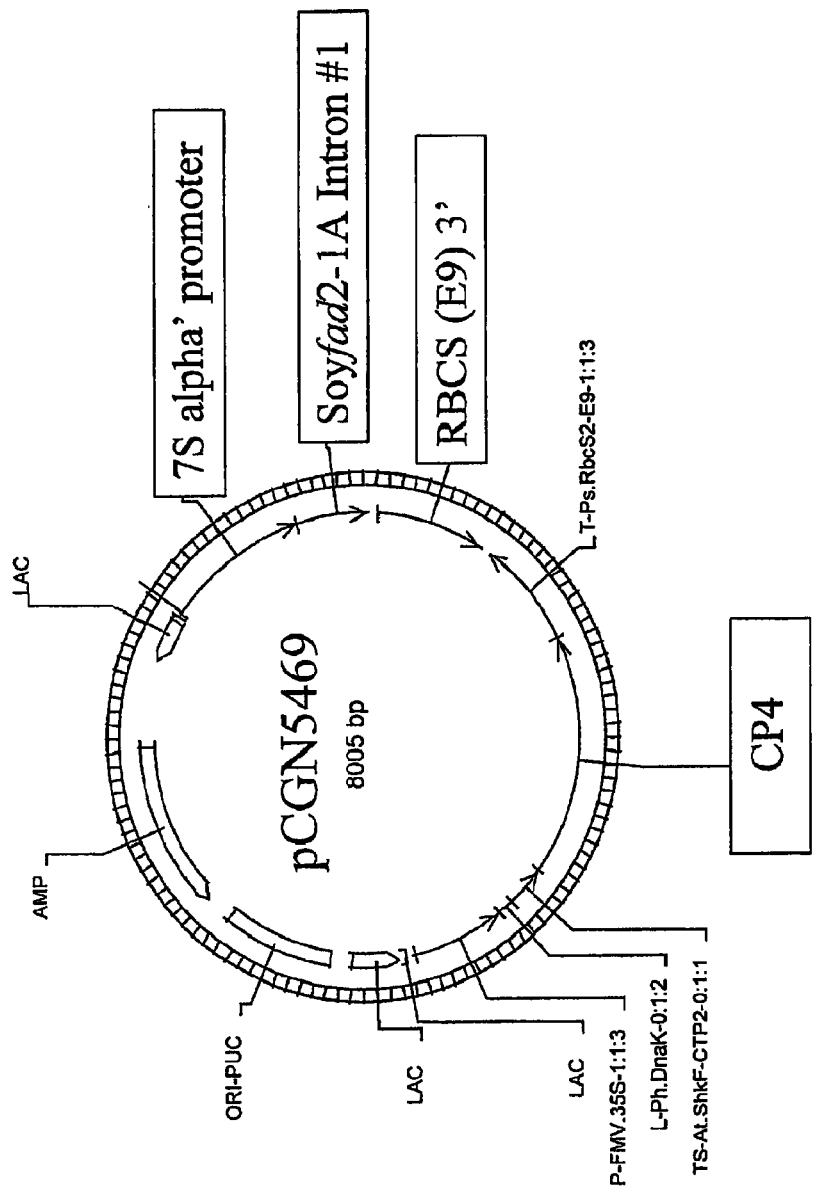
FIG. 1 illustrates pCGN5469, a plant vector for decreasing expression of the soybean FAD2-1 gene.
Figure 2:
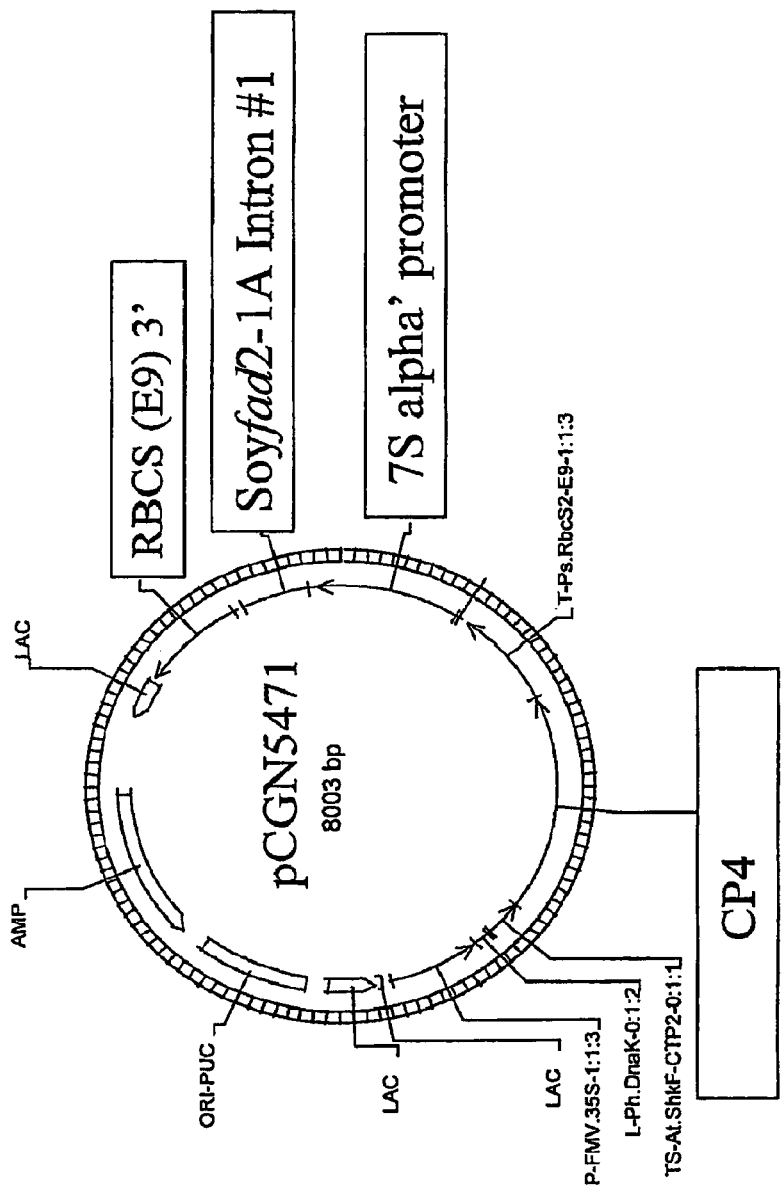
FIG. 2 illustrates pCGN5471, a plant vector for decreasing expression of the soybean FAD2-1 gene.
Figure 3:
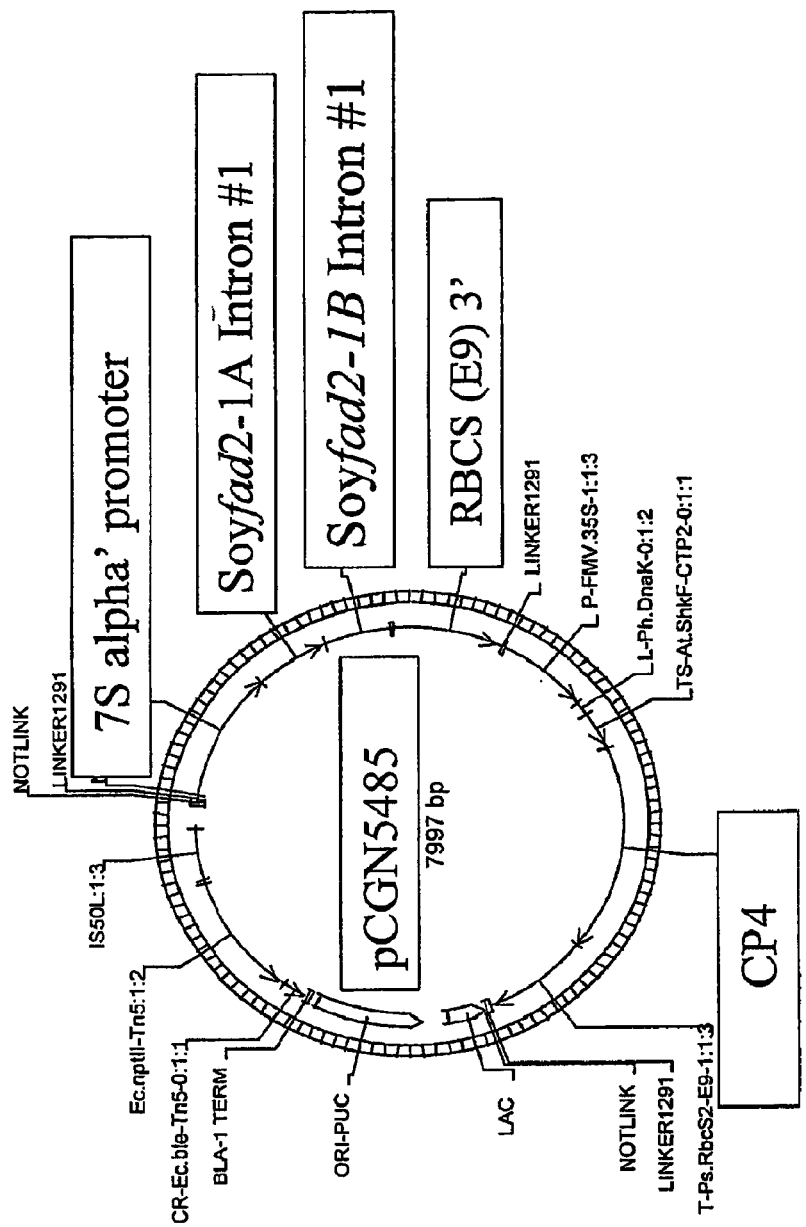
FIG. 3 illustrates pCGN5485, a plant vector for decreasing expression of the soybean FAD2-1 gene.

SEQ ID NO: 1 is a nucleic acid sequence of a FAD2-1A intron 1.

SEQ ID NO: 2 is a nucleic acid sequence of a FAD2-1B intron 1.

SEQ ID NO: 3 is a nucleic acid sequence of a FAD2-1B promoter.

SEQ ID NO: 4 is a nucleic acid sequence of a FAD2-1A genomic clone.

SEQ ID NOs: 5 & 6 are nucleic acid sequences of a FAD2-1A 3' UTR and 5'UTR, respectively.

SEQ ID NOs: 7-13 are nucleic acid sequences of FAD3-1A introns 1, 2, 3A, 4, 5, 3B, and 3C, respectively.

SEQ ID NO: 14 is a nucleic acid sequence of a FAD3-1C intron 4.

SEQ ID NO: 15 is a nucleic acid sequence of a partial FAD3-1A genomic clone.

SEQ ID NOs: 16 & 17 are nucleic acid sequences of a FAD3-1A 3'UTR and 5'UTR, respectively.

SEQ ID NO: 18 is a nucleic acid sequence of a partial FAD3-1B genomic clone.

SEQ ID NOs: 19-25 are nucleic acid sequences of FAD3-1B introns 1, 2, 3A, 3B, 3C, 4, and 5, respectively.

SEQ ID NOs: 26 & 27 are nucleic acid sequences of a FAD3-1B 3'UTR and 5'UTR, respectively.

SEQ ID NO: 28 is a nucleic acid sequence of a FATB-1 genomic clone.

SEQ ID NO: 29-35 are nucleic acid sequences of FATB-1 introns I, II, III, IV, V, VI, and VII, respectively.

SEQ ID NOs: 36 & 37 are nucleic acid sequences of a FATB-1 3'UTR and 5'UTR, respectively.

SEQ ID NO: 38 is a nucleic acid sequence of a *Cuphea pulcherrima* KAS I gene.

SEQ ID NO: 39 is a nucleic acid sequence of a *Cuphea pulcherrima* KAS IV gene.

SEQ ID NOs: 40 & 41 are nucleic acid sequences of *Ricinus communis* and *Simmondsia chinensis* delta-9 desaturase genes, respectively.

SEQ ID NO: 42 is a nucleic acid sequence of a FATB-2 cDNA.

SEQ ID NO: 43 is a nucleic acid sequence of a FATB-2 genomic clone.

SEQ ID NOs: 44-47 are nucleic acid sequences of FATB-2 introns I, II, III, and IV respectively.

SEQ ID NOs: 48-60 are nucleic acid sequences of PCR primers.

SEQ ID NO:61 is a FAD3-1B gene sequence that corresponds to SEQ ID NO:1 from U.S. patent application Ser. No. 10/176,149.

SEQ ID NO: 62 is a FAD3-1C gene sequence that corresponds to SEQ ID NO:2 from U.S. patent application Ser. No. 10/176,149.

SEQ ID NO:63 is a FAD3-1C promoter sequence that corresponds to SEQ ID NO:3 from U.S. patent application Ser. No. 10/176,149.

Definitions

"ACP" refers to an acyl carrier protein moiety. "Altered seed oil composition" refers to a seed oil composition from a transgenic or transformed plant of the invention which has altered or modified levels of the fatty acids therein, relative to a seed oil from a plant having a similar genetic background but that has not been transformed. "Antisense suppression" refers to gene-specific silencing that is induced by the introduction of an antisense RNA molecule.

"Agronomically elite", as used herein, means a genotype that has a culmination of many distinguishable traits such as emergence, vigor, vegetative vigor, disease resistance, seed set, standability and threshability which allows a producer to harvest a product of commercial significance.

"Allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

"Backcrossing" as used herein, refers to a process in which a breeder repeatedly crosses hybrid progeny, for example a first generation hybrid (F1), back to one of the parents of the hybrid progeny. Backcrossing can be used to introduce one or more single locus conversions from one genetic background into another.

"Coexpression of more than one agent such as an mRNA or protein" refers to the simultaneous expression of an agent in overlapping time frames and in the same cell or tissue as another agent. "Coordinated expression of more than one agent" refers to the coexpression of more than one agent when the production of transcripts and proteins from such agents is carried out utilizing a shared or identical promoter.

"Complement" of a nucleic acid sequence refers to the complement of the sequence along its complete length.

"Cosuppression" is the reduction in expression levels, usually at the level of RNA, of a particular endogenous gene or gene family by the expression of a homologous sense construct that is capable of transcribing mRNA of the same strandedness as the transcript of the endogenous gene. Napoli et al., Plant Cell 2:279-289 (1990); van der Krol et al., Plant Cell 2:291-299 (1990).

A "CP4 EPSPS" or "CP4 5-enolpyruvylshikimate-3-phosphate synthase" gene encodes an enzyme (CP4 EPSPS) capable of conferring a substantial degree of glyphosate resistance upon the plant cell and plants generated therefrom. The CP4 EPSPS sequence may be a CP4 EPSPS sequence derived from *Agrobacterium tumefaciens* sp. CP4 or a variant or synthetic form thereof, as described in U.S. Pat. No. 5,633,435. Representative CP4 EPSPS sequences include, without limitation, those set forth in U.S. Pat. Nos. 5,627,061 and 5,633,435.

"Crossing", as used herein, refers to the mating of two parent plants.

"Cross-pollination", as used herein, refers to fertilization by the union of two gametes from different plants.

"$F_1$" or "F1", as used herein, refers to first generation progeny of the cross of two plants.

"$F_1$ Hybrid" or F1 Hybrid", as used herein, refers to first generation progeny of the cross of two non-isogenic plants.

"$F_2$" or "F2", as used herein, refers to second generation progeny of the cross of two plants.

"$F_3$" or "F3", as used herein, refers to third generation progeny of the cross of two plants.

"Crude soybean oil" refers to soybean oil that has been extracted from soybean seeds, but has not been refined, processed, or blended, although it may be degummed.

"CTP" refers to a chloroplastic transit peptide, encoded by the "chloroplastic transit peptide coding sequence".

When referring to proteins and nucleic acids herein, "derived" refers to either directly (for example, by looking at the sequence of a known protein or nucleic acid and preparing a protein or nucleic acid having a sequence similar, at least in part, to the sequence of the known protein or nucleic acid) or indirectly (for example, by obtaining a protein or nucleic acid from an organism which is related to a known protein or nucleic acid) obtaining a protein or nucleic acid from a known protein or nucleic acid. Other methods of "deriving" a protein or nucleic acid from a known protein or nucleic acid are known to one of skill in the art.

Double-stranded RNA ("dsRNA"), double-stranded RNA interference ("dsRNAi") and RNA interference ("RNAi") all refer to gene-specific silencing that is induced by the introduction of a construct capable of transcribing an at least partially double-stranded RNA molecule. A "dsRNA molecule" and an "RNAi molecule" both refer to a region of an RNA molecule containing segments with complementary nucleotide sequences and therefore can hybridize with each other and form double-stranded RNA. Such double-stranded RNA molecules are capable, when introduced into a cell or organism, of at least partially reducing the level of an mRNA species present in a cell or a cell of an organism. In addition, the dsRNA can be created after assembly in vivo of appropriate DNA fragments through illegitimate recombination and site-specific recombination as described in International Application No. PCT/US2005/004681, filed on Feb. 11, 2005, which is hereby incorporated by reference in its entirety.

"Exon" refers to the normal sense of the term as meaning a segment of nucleic acid molecules, usually DNA, that encodes part of or all of an expressed protein.

"FAD2" refers to a gene or encoded protein capable of catalyzing the insertion of a double bond into a fatty acyl moiety at the twelfth position counted from the carboxyl terminus. FAD2 proteins are also referred to as "Δ12 desaturase" or "omega-6 desaturase". The term "FAD2-1" is used to refer to a FAD2 gene or protein that is naturally expressed in a specific manner in seed tissue, and the term "FAD2-2" is used to refer a FAD2 gene or protein that is (a) a different gene from a FAD2-1 gene or protein and (b) is naturally expressed in multiple tissues, including the seed. Representative FAD2 sequences include, without limitation, those set forth in U.S. patent application Ser. No. 10/176,149 filed on Jun. 21, 2002, and in SEQ ID NOs: 1-6.

A "FAD3", "Δ15 desaturase" or "omega-3 desaturase" gene encodes an enzyme (FAD3) capable of catalyzing the insertion of a double bond into a fatty acyl moiety at the fifteenth position counted from the carboxyl terminus. The terms "FAD3-1, FAD3-A, FAD3-B and FAD3-C" are used to refer to FAD3 gene family members that are naturally expressed in multiple tissues, including the seed. Representative FAD3 sequences include, without limitation, those set forth in U.S. patent application Ser. No. 10/176,149 filed on Jun. 21, 2002, and in SEQ ID NOs: 7-27.

A "FATB" or "palmitoyl-ACP thioesterase" refers to a gene that encodes an enzyme (FATB) capable of catalyzing the hydrolytic cleavage of the carbon-sulfur thioester bond in the panthothene prosthetic group of palmitoyl-ACP as its preferred reaction. Hydrolysis of other fatty acid-ACP thioesters may also be catalyzed by this enzyme. Representative FATB-1 sequences include, without limitation, those set forth in U.S. Provisional Application No. 60/390,185 filed on Jun. 21, 2002; U.S. Pat. Nos. 5,955,329; 5,723,761; 5,955,650; and 6,331,664; and SEQ ID NOs: 28-37. Representative FATB-2 sequences include, without limitation, those set forth in SEQ ID NOs: 42-47.

"Fatty acid" refers to free fatty acids and fatty acyl groups.

"Gene" refers to a nucleic acid sequence that encompasses a 5' promoter region associated with the expression of the gene product, any intron and exon regions and 3' or 5' untranslated regions associated with the expression of the gene product.

"Gene silencing" refers to the suppression of gene expression or downregulation of gene expression.

A "gene family" is two or more genes in an organism which encode proteins that exhibit similar functional attributes, and a "gene family member" is any gene of the gene family found within the genetic material of the plant, e.g., a "FAD2 gene family member" is any FAD2 gene found within the genetic material of the plant. An example of two members of a gene family are FAD2-1 and FAD2-2. A gene family can be additionally classified by the similarity of the nucleic acid sequences. A gene, FAD2, for example, includes alleles at that locus. Preferably, a gene family member exhibits at least 60%, more preferably at least 70%, more preferably at least 80% nucleic acid sequence identity in the coding sequence portion of the gene.

"Genotype", as used herein, refers to the genetic constitution of a cell or organism.

As used herein, "Heterologous" means not naturally occurring together.

A nucleic acid molecule is said to be "introduced" if it is inserted into a cell or organism as a result of human manipulation, no matter how indirect. Examples of introduced nucleic acid molecules include, but are not limited to, nucleic acids that have been introduced into cells via transformation, transfection, injection, and projection, and those that have been introduced into an organism via methods including, but not limited to, conjugation, endocytosis, and phagocytosis.

"Intron" refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein. An "intron dsRNA molecule" and an "intron RNAi molecule" both refer to a double-stranded RNA molecule capable, when introduced into a cell or organism, of at least partially reducing the level of an mRNA species present in a cell or a cell of an organism where the double-stranded RNA molecule exhibits sufficient identity to an intron of a gene present in the cell or organism to reduce the level of an mRNA containing that intron sequence.

A "low saturate" soybean seed oil composition contains between 3.6 and 8 percent saturated fatty acids by weight.

A "low linolenic" oil composition contains less than about 3% linolenic acid by weight of the total fatty acids by weight.

A "mid-oleic soybean seed" is a seed having between 55% and 85% oleic acid present in the oil composition of the seed by weight.

The term "non-coding" refers to sequences of nucleic acid molecules that do not encode part or all of an expressed protein. Non-coding sequences include but are not limited to introns, promoter regions, 3' untranslated regions (3'UTRs), and 5' untranslated regions (5'UTRs).

The term "oil composition" refers to levels of fatty acids.

"Phenotype", as used herein, refers to the detectable characteristics of a cell or organism, which characteristics are the manifestation of gene expression.

A promoter that is "operably linked" to one or more nucleic acid sequences is capable of driving expression of one or more nucleic acid sequences, including multiple coding or non-coding nucleic acid sequences arranged in a polycistronic configuration.

"Physically linked" nucleic acid sequences are nucleic acid sequences that are found on a single nucleic acid molecule. A "plant" includes reference to whole plants, plant organs (e.g., leaves, stems, roots, etc.), seeds, and plant cells and progeny of the same. The term "plant cell" includes, without limitation, seed suspension cultures, embryos, meristematic regions, callus tissue, leaves, roots, shoots, gametophytes, sporophytes, pollen, and microspores. "Plant promoters," include, without limitation, plant viral promoters, promoters derived from plants, and synthetic promoters capable of functioning in a plant cell to promote the expression of an mRNA.

A "polycistronic gene" or "polycistronic mRNA" is any gene or mRNA that contains transcribed nucleic acid sequences which correspond to nucleic acid sequences of more than one gene targeted for suppression. It is understood that such polycistronic genes or mRNAs may contain sequences that correspond to introns, 5'UTRs, 3'UTRs, transit peptide encoding sequences, exons, or combinations thereof, and that a recombinant polycistronic gene or mRNA might, for example without limitation, contain sequences that correspond to one or more UTRs from one gene and one or more introns from a second gene.

As used herein, the term "$R_0$," "R0", "$R_0$ generation" or "R0 generation" refers to a transformed plant obtained by regeneration of a transformed plant cell.

As used herein, the term "$R_1$," "R1", "$R_1$ generation" or "R1 generation" refers to seeds obtained from a selfed transgenic $R_0$ plant. $R_1$ plants are grown from the $R_1$ seeds.

A "seed-specific promoter" refers to a promoter that is active preferentially or exclusively in a seed. "Preferential activity" refers to promoter activity that is substantially greater in the seed than in other tissues, organs or organelles of the plant. "Seed-specific" includes without limitation activity in the aleurone layer, endosperm, and/or embryo of the seed.

"Sense intron suppression" refers to gene silencing that is induced by the introduction of a sense intron or fragment thereof. Sense intron suppression is described, for example by Fillatti in PCT WO 01/14538 A2.

"Simultaneous expression" of more than one agent such as an mRNA or protein refers to the expression of an agent at the same time as another agent. Such expression may only overlap in part and may also occur in different tissue or at different levels.

"Total oil level" refers to the total aggregate amount of fatty acid without regard to the type of fatty acid. As used herein, total oil level does not include the glycerol backbone.

"Transgene" refers to a nucleic acid sequence associated with the expression of a gene introduced into an organism. A transgene includes, but is not limited to, a gene endogenous or a gene not naturally occurring in the organism.

A "transgenic plant" is any plant that stably incorporates a transgene in a manner that facilitates transmission of that transgene from a plant by any sexual or asexual method.

A "zero saturate" soybean seed oil composition contains less than 3.6 percent saturated fatty acids by weight.

A "loss-of-function mutation" is a mutation in the coding sequence of a gene, which causes the function of the gene product, usually a protein, to be either reduced or completely absent. A loss-of-function mutation can, for instance, be caused by the truncation of the gene product because of a frameshift or nonsense mutation. A phenotype associated with an allele with a loss of function mutation can be either recessive or dominant.

A cell or organism can have a family of more than one gene encoding a particular enzyme, and the capital letter that follows the gene terminology (A, B, C) is used to designate the family member, i.e., FAD2-1A is a different gene family member from FAD2-1B. Similarly, FAD3-1A, FAD3-1B, and FAD3-1C represent distinct members of the FAD3-1 gene family. Loss of function alleles of various genes are represented in lowercase followed by a minus sign (i.e. fad3-1b– and fad3-1c– represent loss of function alleles of the FAD3-1B and FAD3-1C genes, respectively).

As used herein, any range set forth is inclusive of the end points of the range unless otherwise stated.

A. Transgenes that Decrease the Expression of the Endogenous Soybean FAD2-1 Gene Various transgenes that decrease the expression of the endogenous soybean FAD2-1 gene can be used to practice the methods of the invention. By suppressing, at least partially reducing, reducing, substantially reducing, or effectively eliminating the expression of the endogenous FAD2 gene, the amount of FAD2 protein available in a plant cell is decreased, i.e. the steady-state levels of the FAD2 protein are reduced. Thus, a decrease in expression of FAD2 protein in the soybean cell can result in an increased proportion of mono-unsaturated fatty acids such as oleate (C18:1). Soybean plants that contain transgenes that decrease the expression of the endogenous soybean FAD2-1 and produce seed with increased oleic acid are described in U.S. Pat. No. 7,067,722.

Various transgenes that decrease the expression of both an endogenous soybean FAD2-1 and an endogenous soybean FATB gene can be used to practice the methods of the invention for production of soybean plants with a low linolenic, low saturate, mid-oleic acid phenotype. By suppressing, at least partially reducing, reducing, substantially reducing, or effectively eliminating the expression of the endogenous FATB gene, the amount of FATB protein available in a plant cell is decreased, i.e. the steady-state levels of the FATB protein are reduced. When the amount of FATB is decreased in a plant cell, a decreased amount of saturated fatty acids such as palmitate and stearate can be provided. Thus, a decrease of FATB can result in an increased proportion of unsaturated fatty acids such as oleate (18:1).

Various methods for decreasing expression of either: 1) the endogenous soybean FAD2-1 gene(s) or 2) both the endogenous soybean FAD2-1 and FATB gene(s) in soybean plants and seed are contemplated by this invention, including, but not limited to, antisense suppression, co-suppression, ribozymes, combinations of sense and antisense (double-stranded RNAi), promoter silencing, and use of DNA binding proteins such as zinc finger proteins. The general practice of these methods with respect to various endogenous plant genes is described in WO 98/53083, WO 01/14538, and U.S. Pat. No. 5,759,829. Suppression of gene expression in plants, also known as gene silencing, occurs at both the transcriptional level and post-transcriptional level. Certain of these gene silencing mechanisms are associated with nucleic acid homology at the DNA or RNA level. Such homology refers to similarity in DNA or protein sequences within the same species or among different species. Gene silencing occurs if the DNA sequence introduced to a host cell is sufficiently homologous to an endogenous gene that transcription of the introduced DNA sequence will induce transcriptional or post transcriptional gene silencing of the endogenous gene. To practice this invention, DNA sequences with at least 50%, about 60%, or about 70% identical over the entire length of a DNA sequence of a soybean FAD2-1 or FATB coding region or non-coding region, or to a nucleic acid sequence that is complementary to a soybean FAD2-1 or FATB coding or non-coding region, have sufficient homology for suppression of steady state expression levels of FAD2-1 or FATB when introduced into soybean plants as transgenes. The transgenes of the invention more preferably comprise DNA sequences that are, over their entire length, at least 80% identical; at least 85% identical; at least 90% identical; at least 95% identical; at least 97% identical; at least 98% identical; at least 99% identical; or 100% identical to a soybean FAD2-1 or FATB gene coding region or non-coding region, or to a nucleic acid sequence that is complementary to a soybean FAD2-1 or FATB gene coding or non-coding region. The DNA sequences with the above indicated levels of identity to the soybean FAD2-1 or FAT gene(s) may be coding sequences, intron sequences, 3'UTR sequences, 5'UTR sequences, promoter sequences, other non-coding sequences, or any combination of the foregoing. The intron may be located between exons, or located within a 5' or 3' UTR of a plant gene. The coding sequence is preferably a fraction of a protein encoding frame that does not encode a protein with FAD2 enzymatic activity. However, it is recognized that in certain instances, such as in cosuppression, DNA sequences that encode an enzymatically active FAD2 or FATB protein can be used to decrease expression of the endogenous soybean FAD2-1 or FATB gene(s).

It is also understood that DNA sequences with the above indicated levels of identity to the soybean FAD2-1 gene that are useful in the methods of this invention can be derived from any soybean FAD2 gene, the soybean FAD2-1A gene (SEQ ID NO:4), the soybean FAD2-1A intron (SEQ ID NO:1), Soybean FAD2-1B introns (SEQ ID NO:2 or SEQ ID NO:3), the soybean FAD2-2 gene, alleles of the soybean FAD2-1 gene, alleles of the soybean FAD2-2 gene, and from FAD2 genes derived from other leguminous plants such as *Medicago* sp., *Pisum* sp., *Vicia* sp., *Phaseolus* sp., and *Pisum* sp. It is thus clear that the DNA sequence with the indicated levels of identity to the soybean FAD2-1 sequence can be derived from multiple sources. DNA sequences with the indicated levels of sequence identity can also be obtained synthetically.

Similarly, it is also understood that DNA sequences with the above indicated levels of identity to the soybean FATB gene that are useful in the methods of this invention can be derived from any soybean FATB gene, a soybean FATB-1 gene (SEQ ID NO:28), soybean FATB-1 introns (SEQ ID NO:29-35), soybean FATB-1 5'UTR (SEQ ID NO:36), soybean FATB-1 3'UTR (SEQ ID NO:37), the soybean FATB-2 gene (SEQ ID NO:43), alleles of the soybean FATB-1, alleles of the soybean FATB-2 gene, and from FATB genes derived from other leguminous plants such as *Medicago* sp., *Pisum* sp., *Vicia* sp., *Phaseolus* sp., and *Pisum* sp. It is thus clear that the DNA sequence with the indicated levels of identity to the soybean FAD2-1 sequence can be derived from multiple sources. DNA sequences with the indicated levels of sequence identity can also be obtained synthetically.

In the methods of this invention, transgenes specifically designed to produce double-stranded RNA (dsRNA) molecules with homology to the FAD2-1 gene can also induce FAD2-1 sequence-specific silencing and be used to decrease expression of the endogenous soybean FAD2-1 gene. The sense strand sequences of the dsRNA can be separated from the antisense sequences by a spacer sequence, preferably one that promotes the formation of a dsRNA molecule. Examples of such spacer sequences include those set forth in Wesley et al., Plant J., 27(6):581-90 (2001), and Hamilton et al., Plant J., 15:737-746 (1988). In a preferred aspect, the spacer sequence is capable of forming a hairpin structure as illustrated in Wesley et al., supra. Particularly preferred spacer sequences in this context are plant introns or parts thereof. A particularly preferred plant intron is a spliceable intron. Spliceable introns include, but are not limited to, an intron selected from the group consisting of PDK intron, FAD3-1A or FAD3-1B intron #5, FAD3 intron #1, FAD3 intron #3A, FAD3 intron #3B, FAD3 intron #3C, FAD3 intron #4, FAD3 intron #5, FAD2 intron #1, and FAD2-2 intron. The sense-oriented, non-coding molecules may be, optionally separated from the corresponding antisense-oriented molecules by a spacer segment of DNA. The spacer segment can be a gene fragment or artificial DNA. The spacer segment can be short to facilitate forming hairpin dsRNA or long to facilitate dsRNA without a hairpin structure. The spacer can be provided by extending the length of one of the sense or antisense molecules as disclosed in US 2005/0176670 A1. Alternatively, a right-border-right-border ("RB-RB") sequence can be created after insertion into the plant genome as disclosed in U.S. Patent Application 2005/0183170.

The transgenes of the invention will typically include a promoter functional in a plant cell, or a plant promoter, that is operably linked to an aforementioned DNA sequence that decreases expression of an endogenous soybean FAD2-1 or FATB gene. Design of such a vector is generally within the skill of the art (See, e.g., Plant Molecular Biology: A Laboratory Manual, Clark (ed.), Springer, New York (1997)). However, it is recognized that constructs or vectors may also contain a promoterless gene that may utilize an endogenous promoter upon insertion. A number of promoters that are active in plant cells have been described in the literature such as the CaMV 35S and FMV promoters. Enhanced or duplicated versions of the CaMV 35S and FMV 35S promoters can also be used to express an aforementioned DNA sequence that decreases expression of an endogenous FAD2-1 gene (Odell et al., Nature 313: 810-812 (1985); U.S. Pat. No. 5,378,619). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer can be used with a basal plant promoter. Basal promoters typically comprise a "TATA" box and an mRNA cap site but lack enhancer elements required for high levels of expression.

Particularly preferred promoters for use in the transgenes of the instant invention are promoters that express a DNA sequence that decreases expression of an endogenous soybean FAD2-1 or FATB gene in seeds or fruits. Indeed, in a preferred embodiment, the promoter used is a seed-specific promoter. Examples of such seed-specific promoters include the 5' regulatory regions from such genes as napin (Kridl et al., Seed Sci. Res. 1:209-219 (1991)), phaseolin, stearoyl-ACP desaturase, 7Sα, 7Sα' (Chen et al., Proc. Natl. Acad. Sci., 83:8560-8564 (1986)), USP, arcelin and oleosin. Preferred promoters for expression in the seed are 7Sα, 7Sα', napin, and FAD2-1A promoters.

Constructs or vectors will also typically include a 3' transcriptional terminator or 3' polyadenylation signal that is operably linked to an aforementioned DNA sequence that decreases expression of an endogenous soybean FAD2-1 or FATB gene. The transcriptional termination signal can be any transcriptional termination signal functional in a plant, or any plant transcriptional termination signal. Preferred transcriptional termination signals include, but are not limited to, a pea Rubisco E9 3' sequence, a *Brassica* napin 3' sequence, a tml 3' sequence, and an *Agrobacterium* tumor-inducing (Ti) plasmid nopaline synthase (NOS) gene 3' sequence. It is understood that this group of exemplary polyadenylation regions is non-limiting and that one skilled in the art could employ other polyadenylation regions that are not explicitly cited here in the practice of this invention.

Finally, it is also recognized that transgenes of the invention can be inserted in plant transformation vectors that also comprise genes that encode selectable or scoreable markers. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection). A preferred selectable marker gene is a CP4 EPSPS gene that confers resistance to the herbicide glyphosate. The scoreable marker gene can be a gene encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

The above-described nucleic acid molecules are embodiments which achieve the objects, features and advantages of the present invention. It is not intended that the present invention be limited to the illustrated embodiments. The arrangement of the sequences in the first and second sets of DNA sequences within the nucleic acid molecule is not limited to the illustrated and described arrangements, and may be altered in any manner suitable for achieving the objects, features and advantages of the present invention as described herein and illustrated in the accompanying drawings.

B. Transgenic Organisms, and Methods for Producing Same

Any of the nucleic acid molecules and constructs of the invention may be introduced into a soybean plant or plant cell in a permanent or transient manner. Methods and technology for introduction of DNA into soybean plant cells are well known to those of skill in the art, and virtually any method by which nucleic acid molecules may be introduced into a cell is suitable for use in the present invention. Non-limiting examples of suitable methods include: chemical methods; physical methods such as microinjection, electroporation, the gene gun, microprojectile bombardment, and vacuum infiltration; viral vectors; and receptor-mediated mechanisms. Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

*Agrobacterium*-mediated transfer is a widely applicable system for introducing genes into plant cells. See, e.g., Fraley et al., Bio/Technology 3:629-635 (1985); Rogers et al., Methods Enzymol. 153:253-277 (1987). The region of DNA to be transferred is defined by the border sequences and intervening DNA is usually inserted into the plant genome. Spielmann et al., Mol. Gen. Genet. 205:34 (1986). Modern *Agrobacterium* transformation vectors are capable of replication in *E. coli* as well as *Agrobacterium*, allowing for convenient manipulations. Klee et al., In: Plant DNA Infectious Agents, Hohn and Schell (eds.), Springer-Verlag, New York, pp. 179-203 (1985). *Agrobacterium*-mediated transformation of soybean is specifically described in U.S. Pat. No. 7,002,058.

Transgenic plants are typically obtained by linking the gene of interest (i.e., in this case a transgene that decreases expression of an endogenous soybean FAD2-1 gene or that decreases expression of both an FAD2-1 gene or FATB gene) to a selectable marker gene, introducing the linked transgenes into a plant cell, a plant tissue or a plant by any one of the methods described above, and regenerating or otherwise recovering the transgenic plant under conditions requiring expression of said selectable marker gene for plant growth. Exemplary selectable marker genes and the corresponding selective agents have been described in preceding sections of this description of the invention.

Transgenic plants can also be obtained by linking a gene of interest (i.e. in this case a transgene that decreases expression of an endogenous soybean FAD2-1 gene or that decreases expression of both an FAD2-1 gene or FATB gene) to a scoreable marker gene, introducing the linked transgenes into a plant cell by any one of the methods described above, and regenerating the transgenic plants from transformed plant cells that test positive for expression of the scoreable marker gene. Exemplary scoreable marker genes have been described in preceding sections of this description of the invention.

The regeneration, development and cultivation of plants from single plant protoplast transformants or from various transformed explants is well known in the art. See generally, Maliga et al., Methods in Plant Molecular Biology, Cold Spring Harbor Press (1995); Weissbach and Weissbach, In: Methods for Plant Molecular Biology, Academic Press, San Diego, Calif. (1988). Plants of the present invention can be part of or generated from a breeding program, and may also be reproduced using apomixis. Methods for the production of apomictic plants are known in the art. See, e.g., U.S. Pat. No. 5,811,636.

A particular method of obtaining low linolenic/mid-oleic soybean plants contemplated herein entails the direct transformation of soybean varieties comprising at least one loss-of-function mutation in an endogenous soybean FAD3 gene with a transgene that decreases the expression of an endogenous soybean FAD2-1 gene. Examples of soybean varieties comprising at least one loss-of-function mutation in an endogenous soybean FAD3 gene include A5, C1640, 6P248, N98-44, T27111, T27190, T26767, T26830, and Soyola™ soybean (see U.S. Patent Application 20060107348, now U.S. Pat. No. 7,442,850 and Burton et al., Crop Sci. 44:687-688, 2004). It is also contemplated that other soybean lines that comprise at least one loss-of-function mutation in an endogenous soybean FAD3 gene and that possess agronomically elite growth and/or yield characteristics produced by the marker-assisted breeding methods disclosed in U.S. Patent Application 20060107348, now U.S. Pat. No. 7,442,850 could be directly transformed with a transgene that decreases the expression of an endogenous soybean FAD2-1 gene. Alternatively, it is also contemplated that soybean lines that comprise at least one loss-of-function mutation in an endogenous soybean FAD3 gene and that are amenable to transformation can be produced by the marker-assisted breeding methods disclosed in U.S. patent application Ser. No. 11/239,676, now U.S. Pat. No. 7,442,850. Soybean plants comprising at least one loss-of-function mutation in an endogenous soybean FAD3 gene and that are amenable to transformation can also be directly transformed with a transgene that decreases the expression of an endogenous soybean FAD2-1 gene. Three other low linolenic soybeans that could be directly transformed by the methods of the invention include BARC12, which is a determinant maturity group #3 line, Vistive™ soybean lines (Monsanto, St. Louis, Mo., USA), or 0137648/01AHKW-38, which is a yellow hilum L2 NUL line.

It is also contemplated that the low linolenic soybean plants that are directly transformed with the transgene in the methods of the invention can be derived from soybean germplasm comprising soybean plant genomic regions that contain fad3-1b–, fad3-1c–, or both fad3-1b– and fad3-1c– alleles that confer decreased linolenic acid content. Such single nucleotide polymorphisms associated with the low linolenic soybean phenotype are described in U.S. patent application Ser. No. 11/239,676, now U.S. Pat. No. 7,442,850. In certain embodiments, a soybean genomic region that confers the low linolenic acid content phenotype is characterized by a single nucleotide polymorphism at a position in the FAD3-1B gene sequence corresponding to nucleotide 2021 of SEQ ID NO:61. In another embodiment, the soybean genomic region that confers the low linolenic acid content phenotype is characterized by a single nucleotide polymorphism at a position in the FAD3-1C gene sequence corresponding to nucleotide 687, 1129, 1203, 2316, 3292, 3360 or 3743 of SEQ ID NO:62. In another embodiment, the soybean genomic region that confers the low linolenic acid content phenotype is characterized by a single nucleotide polymorphism at a position in the FAD3-1C promoter corresponding to nucleotide 334, 364, 385, 387, 393, 729 or 747 of SEQ ID NO:63. In another embodiment, the soybean genomic region that confers the low linolenic acid content phenotype is characterized by a deletion in the FAD3-1C gene. The soybean genomic regions that confer the low linolenic acid content phenotype can also be characterized by both a single nucleotide polymorphism at a position in the FAD3-1B gene sequence corresponding to nucleotide 2021 of SEQ ID NO:61 and a deletion in the FAD3-1c gene sequence. The soybean genomic regions that confer the low linolenic acid content phenotype can also be characterized by both a single nucleotide polymorphism at a position in the FAD3-1B gene sequence corresponding to nucleotide 2021 of SEQ ID NO:61 and a polymorphism in the FAD3-1C promoter, such as a single nucleotide polymorphism at a position corresponding to nucleotide 334, 364, 385, 387, 393, 729 or 747 of SEQ ID NO:63. Soybean germplasm comprising a deletion in the Soybean FAD3-1C gene is useful in the practice of these methods and can be obtained from soybean lines that include but are not limited to soybean lines 6P248, T27111, T27190, T26767, T26830 and A5, described in U.S. patent application Ser. No. 11/239, 676, now U.S. Pat. No. 7,442,850.

Detecting the single nucleotide polymorphisms may be carried out by any method, including PCR, single strand conformational polymorphism analysis, denaturing gradient gel electrophoresis, cleavage fragment length polymorphism analysis and/or DNA sequencing as described in U.S. patent application Ser. No. 11/239,676, now U.S. Pat. No. 7,442, 850. Alternatively, the single nucleotide polymorphism can be detected by any one assay selected from the group consisting of single base extension (SBE), allele-specific primer extension sequencing (ASPE), sequencing, universal PCR, allele specific extension, hybridization, mass spectrometry, ligation, extension-ligation, and Flap Endonuclease-mediated assays. Primers and methods for detection of the aforementioned FAD3-1B and FAD3-1C genetic polymorphisms are described in U.S. patent application Ser. No. 11/239,676, now U.S. Pat. No. 7,442,850. Deletions such as those in the FAD3-1C gene can be detected by methods including but not limited to PCR, hybridization, cleavage fragment length polymorphism analysis and/or DNA sequencing—based methods.

Direct transformation methods as described above can also be used to obtain low linolenic/low saturate/mid-oleic soybean plants. In these methods, the aforementioned low linolenic soybean plants are directly transformed with transgenes that decrease the expression of both an endogenous soybean FAD2-1 and an endogenous soybean FATB gene for production of soybean plants with a low linolenic, low saturate, mid-oleic acid phenotype.

Transgenes that may be used in plant transformation or transfection may be any of the transgenes that decrease expression of either: 1) the endogenous soybean FAD2-1 gene(s) or 2) both the endogenous soybean FAD2-1 and FATB gene(s). It is further contemplated that vectors comprising transgenes that decrease expression of either: 1) the endogenous soybean FAD2-1 gene(s) or 2) both the endogenous soybean FAD2-1 and FATB gene(s) can also comprise or be genetically combined with additional transgenes. For example, additional transgenes that express other genes that affect oil composition, pathogen resistance, yield, morphology, protein composition, amino acid composition, starch composition, and phytate level are described in U.S. patent application Ser. No. 11/239,676, now U.S. Pat. No. 7,442,850 and can be combined with the transgenes and low linolenic mutants described herein.

It is not intended that the present invention be limited to the illustrated embodiments. Exemplary nucleic acid molecules have been described in Part A of the Detailed Description, and further non-limiting exemplary nucleic acid molecules are described below and illustrated in FIGS. 1-4, and in the Examples.

C. Crosses of Soybean Plants Containing Transgenes

In another aspect, a plant of the invention can be crossed with another plant that is transgenic or non-transgenic. A plant can be crossed with another plant that has an oil composition containing modified levels of fatty acids, for example without limitation, a variety with an oil composition having a lower level of linolenic acid. In a preferred embodiment, a plant of the present invention is crossed with a variety with less than 3% by weight linolenic acid. In another embodiment of the invention, a plant of the present invention is crossed with another plant having greater than 20% by weight stearic acid. Such plants having modified levels of fatty acids are known in the art and described, for example, in Hawkins and Kridl (1998) Plant Journal 13(6): 743-752 and U.S. Pat. No. 6,365,802.

In particular, crosses of soybean plants comprising a transgene that either decrease the expression of an endogenous soybean FAD2-1 gene or decrease the expression of both the endogenous soybean FAD2-1 and FATB gene(s) with soybean varieties comprising at least one loss-of-function mutation in an endogenous soybean FAD3 gene are contemplated by the methods of this invention. Examples of soybean varieties comprising at least one loss-of-function mutation in an endogenous soybean FAD3 gene include A5, C1640, 6P248, N98-44, T27111, T27190, T26767, T26830, and Soyola™ soybean (see U.S. Patent Application 20060107348, now U.S. Pat. No. 7,442,850 and Burton et al., Crop Sci. 44:687-688, 2004). It is also contemplated that other soybean lines that comprise at least one loss-of-function mutation in an endogenous soybean FAD3 gene and that possess agronomically elite growth and/or yield characteristics produced by the marker-assisted breeding methods disclosed in see U.S. Patent Application 20060107348, now U.S. Pat. No. 7,442,850 could be crossed with soybean plants comprising a transgene that decreases the expression of an endogenous soybean FAD2-1 gene. Three other low linolenic crossing parents that could be used in the methods of the invention include BARC12, which is a determinant maturity group #3 line, Vistive™ soybean lines, or 0137648/01AHKW-38, which is a yellow hilum L2 NUL line.

It is also contemplated that the low linolenic soybean plants used in the cross to the transgene(s) can be derived from soybean germplasm comprising soybean plant genomic regions that contain fad3-1b–, fad3-1c–, or both fad3-1b– and fad3-1c– alleles that confer decreased linolenic acid content. Such single nucleotide polymorphisms associated with the low linolenic soybean phenotype are described in U.S. patent application Ser. No. 11/239,676, now U.S. Pat. No. 7,442,850. In certain embodiments, a soybean genomic region that confers the low linolenic acid content phenotype is characterized by a single nucleotide polymorphism at a position in the FAD3-1B gene sequence corresponding to nucleotide 2021 of SEQ ID NO:61. In another embodiment, the soybean genomic region that confers the low linolenic acid content phenotype is characterized by a single nucleotide polymorphism at a position in the FAD3-1C gene sequence corresponding to nucleotide 687, 1129, 1203, 2316, 3292, 3360 or 3743 of SEQ ID NO:62. In another embodiment, the soybean genomic region that confers the low linolenic acid content phenotype is characterized by a single nucleotide polymorphism at a position in the FAD3-1C promoter corresponding to nucleotide 334, 364, 385, 387, 393, 729 or 747 of SEQ ID NO:63. In another embodiment, the soybean genomic region that confers the low linolenic acid content phenotype is characterized by a deletion in the FAD3-1C gene. The soybean genomic regions that confer the low linolenic acid content phenotype can also be characterized by both a single nucleotide polymorphism at a position in the FAD3-1B gene sequence corresponding to nucleotide 2021 of SEQ ID NO:61 and a deletion in the FAD3-1C gene sequence. The soybean genomic regions that confer the low linolenic acid content phenotype can also be characterized by both a single nucleotide polymorphism at a position in the FAD3-1B gene sequence corresponding to nucleotide 2021 of SEQ ID NO:61 and a polymorphism in the FAD3-1C promoter, such as a single nucleotide polymorphism at a position corresponding to nucleotide 334, 364, 385, 387, 393, 729 or 747 of SEQ ID NO:63. Soybean germplasm comprising a deletion in the Soybean FAD3-1C gene is useful in the practice of these methods and can be obtained from soybean lines that include but are not limited to soybean lines 6P248, T27111, T27190, T26767, T26830 and A5, described in U.S. patent application Ser. No. 11/239,676, now U.S. Pat. No. 7,442,850. Tables 3 and 4 of the Examples describe the association of specific polymorphisms with specific soybean germplasm or soybean lines that display low linolenic acid phenotypes.

Without being limited by theory, it is further noted that certain polymorphisms and deletions in certain FAD3-1C genes are potentially responsible in part for the low linolenic acid phenotypes displayed by soybean plants that carry these polymorphisms or deletions. The SNP at 2021 position in SEQ ID NO:61 is a sense mutation that changes an amino acid residue from Histidine to Tyrosine. The histidine residue has been found to be critical in a number of genes involved with desaturation. This particular SNP found caused a mutation in the motif His-Val-Ile-His-His (SEQ ID NO:64) to His-Val-Ile-His-Tyr (SEQ ID NO:65) in the low linolenic lines. The motif has been associated with a low-linolenic phenotype and is a likely cause for the reduced linolenic acid phenotype observed in soybeans with this polymorphism.

Detecting the single nucleotide polymorphism may be carried out by any method, including PCR, single strand conformational polymorphism analysis, denaturing gradient gel electrophoresis, cleavage fragment length polymorphism analysis and/or DNA sequencing as described in U.S. patent application Ser. No. 11/239,676, now U.S. Pat. No. 7,442,850. Alternatively, the single nucleotide polymorphism can be detected by any one of an assay selected from the group consisting of single base extension (SBE), allele-specific primer extension sequencing (ASPE), sequencing, universal PCR, allele specific extension, hybridization, mass spectrometry, ligation, extension-ligation, and Flap Endonuclease-mediated assays. Primers and methods for detection of the aforementioned FAD3-1B and FAD3-1C genetic polymorphisms are described in U.S. patent application Ser. No. 11/239,676, now U.S. Pat. No. 7,442,850. Deletions such as those in the FAD3-1C gene can be detected by methods including but not limited to PCR, hybridization, cleavage fragment length polymorphism analysis and/or DNA sequencing—based methods.

Crossing methods as described above can also be used to obtain low linolenic/low saturate/mid-oleic soybean plants. In these methods, the aforementioned low linolenic soybean plants are crossed with soybean plants comprising transgenes that decrease the expression of both an endogenous soybean FAD2-1 and an endogenous soybean FATB gene for production of soybean plants with a low linolenic, low saturate, mid-oleic acid phenotype.

It is further contemplated that the crosses of the transgene(s) to the low linolenic soybean lines can be facilitated by linkage of a selectable marker that confers resistance to a herbicide. For example, in crosses of soybean plants that are heterozygous for the transgene with plants that are either homozygous or heterozygous for the allele(s) conferring the low linolenic trait, F1 progeny that are heterozygous for the transgene can be selected by herbicide treatment. Also, F2 plants derived from F1 plants that are heterozygous for the transgene can be enriched for F2 soybean plants that are homozygous for said transgene by subjecting said plurality of F2 plants to herbicide selection for the transgene. Molecular markers that can distinguish soybean plants that are either heterozygous or homozygous for the transgene can also be used to identify soybean plants that are homozygous for the transgene insertion.

Soybean plants (Glycine max L.) can be crossed by either natural or mechanical techniques. Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod. The critical day length for flowering ranges from about 13 h for genotypes adapted to tropical latitudes to 24 h for photoperiod-insensitive genotypes grown at higher latitudes. Soybeans seem to be insensitive to day length for 9 days after emergence. Photoperiods shorter than the critical day length are required for 7 to 26 days to complete flower induction.

Soybean flowers typically are self-pollinated on the day the corolla opens. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed. Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Genetic male sterility is available in soybeans and may be useful to facilitate hybridization in the context of the current invention, particularly for recurrent selection programs. The distance required for complete isolation of a crossing block is not clear; however, out-crossing is less than 0.5% when male-sterile plants are 12 m or more from a foreign pollen source (Boerma and Moradshahi, Crop Sci., 15:858-861, 1975). Plants on the boundaries of a crossing block probably sustain the most out-crossing with foreign pollen and can be eliminated at harvest to minimize contamination.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

F. Products of the Present Invention

The plants of the present invention may be used in whole or in part. Preferred plant parts include reproductive or storage parts. The term "plant parts" as used herein includes, without limitation, seed, endosperm, ovule, pollen, roots, tubers, stems, leaves, stalks, fruit, berries, nuts, bark, pods, seeds and flowers. In a particularly preferred embodiment of the present invention, the plant part is a seed.

Any of the plants or parts thereof of the present invention may be processed to produce a feed, meal, protein, or oil preparation. A particularly preferred plant part for this purpose is a seed. In a preferred embodiment the feed, meal, protein or oil preparation is designed for livestock animals, fish or humans, or any combination. Methods to produce feed, meal, protein and oil preparations are known in the art. See, e.g., U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v.

In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such oil may exhibit enhanced oxidative stability. Also, such oil may be a minor or major component of any resultant product.

Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Seeds of the plants may be placed in a container. As used herein, a container is any object capable of holding such seeds. A container preferably contains greater than about 500, 1,000, 5,000, or 25,000 seeds where at least about 10%, 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

Soybean seeds produced by the methods of the invention can comprise various oil compositions. An oil produced by soybean seeds produced by the methods of the invention are referred to below as an "oil of the present invention".

A preferred oil of the present invention has a low saturate oil composition, or a zero saturate oil composition. In other preferred embodiments, oils of the present invention have increased oleic acid levels, reduced saturated fatty acid levels, and reduced polyunsaturated fatty acid levels. In further preferred embodiments, oils of the present invention have increased oleic acid levels and reduced saturated fatty acid levels. In a preferred embodiment, the oil is a soybean oil. The percentages of fatty acid content, or fatty acid levels, used herein refer to percentages by weight.

In a first embodiment, an oil of the present invention preferably has an oil composition that is 55 to 80% oleic acid, about 12 to 43% polyunsaturates, and 2 to 8% saturated fatty acids; more preferably has an oil composition that is 55 to 80% oleic acid, about 14 to 42% polyunsaturates, and 3 to 6% saturated fatty acids; and even more preferably has an oil composition that is 55 to 80% oleic acid, about 16.5 to 43% polyunsaturates, and 2 to 3.6% saturated fatty acids.

In a second embodiment, an oil of the present invention preferably has an oil composition that is 65 to 80% oleic acid, about 12 to 33% polyunsaturates, and 2 to 8% saturated fatty acids; more preferably has an oil composition that is 65 to 80% oleic acid, about 14 to 32% polyunsaturates, and 3 to 6% saturated fatty acids; and even more preferably has an oil composition that is 65 to 80% oleic acid, about 16.5 to 33% polyunsaturates, and 2 to 3.6% saturated fatty acids.

In a third embodiment, an oil of the present invention preferably has an oil composition that is about 42 to about 85% oleic acid and about 8% to about 1.5% saturated fatty acids.

In a fourth embodiment, an oil of the present invention has an oil composition that is about 42 to about 85% oleic acid, about 8% to about 1.5% saturated fatty acids, about 6% to about 15% by weight linolenic acid; more preferably has an oil composition that is about 42 to about 85% oleic acid, about 8% to about 1.5% saturated fatty acids, less than 35% by weight linolenic acid; and even more preferably has an oil composition that is about 42 to about 85% oleic acid, about 8% to about 1.5% saturated fatty acids, about 9% by weight linolenic acid.

In a fifth embodiment, an oil of the present invention has an oil composition that is about 50% to about 85% oleic acid and about 8% to about 1.5% saturated fatty acids; more preferably about 50% to about 85% oleic acid, about 8% to about 1.5% saturated fatty acids, about 4% to about 14% by weight linolenic acid; more preferably has an oil composition that is about 50% to about 85% oleic acid, about 8% to about 1.5% saturated fatty acids, less than 35% by weight linolenic acid; and even more preferably has an oil composition that is about 42 to about 85% oleic acid, about 8% to about 1.5% saturated fatty acids, about 2% to about 45% by weight linolenic acid.

In another embodiment, an oil of the present invention has an oil composition that is about 65-80% oleic acid, about 3-8% saturates, and about 12-32% polyunsaturates. In another embodiment, an oil of the present invention has an oil composition that is about 65-80% oleic acid, about 2-3.5% saturates, and about 16.5-33% polyunsaturates.

In a particularly preferred embodiment, an oil of the present invention has an oil composition that is about 47-83% oleic acid and about 5% saturates; about 60-80% oleic acid and about 5% saturates; about 50-85% oleic and about 2-7% saturates; about 55-85% oleic acid and about 2.5-7% saturates; about 47-88% oleic acid and about 3-7% saturates; about 43-85% oleic acid and about 5-7% saturates; about 81-85% oleic acid and about 5% saturates; about 74-83% oleic acid and about 6% saturates; about 65-87% oleic acid and about 6% saturates; about 66-80% oleic acid and about 6% saturates; about 42-77% oleic acid and about 5-8% saturates; about 60-77% oleic acid and about 6% saturates; about 70-81% oleic acid and about 5-7% saturates; about 52-71% oleic acid and about 5-7% saturates; about 44-71% oleic acid and about 6% saturates; about 61-71% oleic acid and about 8% saturates; about 57-71% oleic acid and about 7% saturates; about 23-58% oleic acid and about 8-14% saturates; about 20-70% oleic acid and about 6% saturates; about 21-35% oleic acid and about 5-6% saturates; or about 19-28% oleic acid and about 5% saturates.

In other embodiments, the percentage of oleic acid is 50% or greater; 55% or greater; 60% or greater; 65% or greater; 70% or greater; 75% or greater; or 80% or greater; or is a range from 50 to 80%; 55 to 80%; 55 to 75%; 55 to 65%; 60 to 85%; 60 to 80%; 60 to 75%; 60 to 70%; 65 to 85%;

65 to 80%; 65 to 75%; 65 to 70%; or 69 to 73%. Suitable percentage ranges for oleic acid content in oils of the present invention also include ranges in which the lower limit is selected from the following percentages: 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 percent; and the upper limit is selected from the following percentages: 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 percent.

In other embodiments, the percentage of linolenic acid in an oil of the present invention is 10% or less; 9% or less; 8% or less; 7% or less; 6% or less; 5% or less; 4.5% or less; 4% or less; 3.5% or less; 3% or less; 3.0% or less; 2.5% or less; or 2% or less; or is a range from 0.5 to 2%; 0.5 to 3%; 0.5 to 4.5%; 0.5% to 6%; 3 to 5%; 3 to 6%; 3 to 8%; 1 to 2%; 1 to 3%; or 1 to 4%.

In these other embodiments, the percentage of saturated fatty acids in an oil composition of the present invention is 15% or less; 14% or less; 13% or less; 12% or less, 11% or less; 10% or less; 9% or less; 8% or less; 7% or less; 6% or less; 5% or less; 4% or less; or 3.6% or less; or is a range from 2 to 3%; 2 to 3.6%; 2 to 4%; 2 to 8%; 3 to 15%; 3 to 10%; 3 to 8%; 3 to 6%; 3.6 to 7%; 5 to 8%; 7 to 10%; or 10 to 15%.

In other embodiments, saturated fatty acids in an oil of the present invention includes the combination of the palmitic and stearic fatty acids. In an embodiment, the percentage of saturated fatty acids ranges from about 10% or less; about 9% or less; about 8% or less; about 7% or less; about 6% or less; about 5% or less; about 4.5% or less; about 4% or less; about 3.5% or less; about 3% or less; about 3.0% or less; about 2.5% or less; or about 2% or less; or is a range from 0.5 to 2%; 0.5 to 3%; 0.5 to 4.5%; 0.5 to 6%; 0.5 to 7%; 0.5 to 8%; 0.5 to 9%; 1 to 4%; 1 to 5%; 1 to 6%; 1 to 7%; 1 to 8%; 1 to 9%; 1.5 to 5%; 1.5 to 6%; 1.5 to 7/0; 1.5 to 8%; 1.5 to 9%; 2 to 5%; 2 to 6%; 2 to 7%; 2 to 8%; 2 to 9%; 3 to 5%; 3 to 6%; 3 to 7%; 3 to 8%; 3 to 9%; 4 to 7%; 4 to 8%; 4 to 9%; 5 to 7%; 5 to 8%; and 5 to 9%. In these embodiments, suitable percentage ranges for saturated fatty acid content in oils of the present invention also include ranges in which the lower limit is selected from the following percentages: 0.5, 1, 1.5, 2, 2.5, 3, 3.5, 4, 4.5, 5, 5.5, 6, or 6.5 percent; and the upper limit is selected from the following percentages: 11, 10, 9, 8, 7, 6, 5, 4.5, 4, 3.5, 3, 2.5, 2, 1.5, 1, or 0.5 percent.

G. Modulation of Suppression

Another embodiment of the invention is directed to a method of modulating gene suppression levels. Modulation of gene suppression can result in more or less gene suppression. Suppression of a gene product can be the result from insertion of a construct of the present invention into a plant genome. Similarly, modulation of gene suppression can be the result from insertion of a construct of the present invention into a plant genome. Other examples of methods to modulate gene suppression include, without limitation, antisense techniques, cosuppression, RNA interference (dsRNAi), transgenic animals, hybrids, and ribozymes using a construct of the present invention. The following examples are provided by way of illustration, and are not intended to be limiting of the present invention.

Suppression of a gene can be modulated by altering the length of the transcribable DNA used for suppression, which sequence is derived from the gene targeted for suppression. Many methods can be used for suppressing a gene using post-transcriptional gene silencing mechanisms. Without being limited to the theory, these methods are believed to have in common the expression of an RNA molecule which hybridizes to another RNA molecule. Surprisingly, there can be advantages to using an RNA molecule of particular lengths to modulate or moderate suppression of the steady state expression levels of a targeted endogenous gene.

Gene suppression of FAD2-1 leads to elevated levels of oleic acid and reduction of linoleic acid levels. When FAD2-1 is heavily suppressed, levels of oleic acid can be greater than 65%, which causes a reduction in palmitic acid and linolenic acid levels. For example, when FAD2-1 is suppressed, oleic acid levels can reach 85% and the combined palmitic and stearic acid levels are reduced to about 10%. Similarly, downregulation of FATB results in decreased levels of saturated fatty acids, primarily palmitate. When FAD2 and FATB are suppressed so that oleic levels are about 85%, saturate levels are about 10%. When FAD2 and FATB are suppressed so that oleic levels are greater than 85%, saturate levels can fall below 10%.

In light of the present invention, saturate levels can be reduced to less than 10% without enhancing oleic acids above 85%. In one embodiment, the suppression of FAD2 is modulated by reducing the length of FAD2-1 intron introduced into the plant. Less suppression of FAD2 results in moderate levels of oleic acid, approximately 40-85% oleic acid. The suppression of FAD2 is reduced as the length of the FAD2-1 intron fragment introduced is reduced. For example, a FAD2-1 intron reduced in length by at least 100 contiguous nucleotides can reduce the suppression of FAD2 and the corresponding increase in oleic acid and decrease in linoleic acid levels.

The relationship between the decrease in endogenous gene suppression and the decrease in length of homologous DNA can be determined empirically by introducing different lengths of DNA. For example, the amount of reduction in suppression obtainable by reducing the length of homologous introduced DNA can be determined by deleting increasing portions of the homologous DNA being introduced and assaying for expression of the targeted gene.

Included in the present invention is a method for moderating suppression of FAD2 while still having a strong reduction of saturate levels in a plant. In such plants, oleic acid levels can range from 40-85%. Similarly, less than full suppression of FATB occurs when the combined 3' and 5' untranslated regions are introduced as compared to when the full-length FATB gene is introduced into a host cell. In a like manner, suppression levels of FATB are reduced when the 5' part of the open reading frame, which mostly encodes the chloroplast transit peptide, is introduced into a host cell. In cells with FAD2 and FATB suppressed using methods according to the present invention, oleic acid levels can be 40-85% while saturate levels can be between 1 to 9 percent.

In one embodiment, the present invention is directed to a method of modulating gene suppression to reduce suppression relative to the suppression from an entire gene element, where an entire gene element can be an entire gene, an entire exon, an entire intron, an entire signal sequence, or an entire UTR, then constructing a recombinant nucleic acid molecule comprising a fragment of the endogenous sequence from the gene element; initiating expression of the recombinant nucleic acid molecule in a host cell; and suppressing the endogenous gene with the recombinant nucleic acid molecule. The gene being suppressed can be any gene, including FAD2 and FATB. In one embodiment, the present invention is directed to a method of modulating FAD2 or FATB suppression comprising: expressing a partial FAD2 or FATB gene element sequence in a host cell, where a FAD2 or FATB gene element is from an endogenous FAD2 or FATB gene in the host cell and a FAD2 or FATB gene element sequence can be a FAD2 or FATB gene, a FAD2 or FATB exon, a FAD2 or FATB intron, a FAD2 or FATB transit peptide coding region, or a FAD2 or FATB UTR; and the partial FAD2 or FATB gene element sequence is less than the entire FAD2 or FATB gene element sequence; and suppressing an endogenous FAD2 or FATB with the partial FAD2 or FATB gene element sequence, where suppression levels of the FAD2 or FATB endogenous gene in the host cell are less than suppression levels of the FAD2 or FATB endogenous gene in a host cell with a similar genetic background and a second FAD2 or FATB nucleic acid sequence comprising the entire FAD2 or FATB gene element sequence of the FAD2 or FATB gene element.

In another embodiment, the present invention is directed to a method of altering the oil composition of a plant cell by transforming a plant cell with a recombinant nucleic acid molecule which comprises a DNA sequence that suppresses endogenous expression of FAD2, FATB, or FAD2 and FATB where the DNA sequence comprises a nucleic acid sequence of FAD2, FATB, or FAD2 and FATB that is shorter than the entire sequence of an entire genetic element selected from a gene, an exon, an intron, a transit peptide coding region, a 3'-UTR, a 5'-UTR, and an open reading frame; and growing the plant cell under conditions where transcription of said DNA sequence is initiated, whereby the oil composition is altered relative to a plant cell with a similar genetic background but lacking the recombinant nucleic acid molecule. A gene element of FAD2 or FATB can be shortened in length by 50, 75, 100, 150, 175, 200, 250, 300, 350, 400, 450, 500, 600, 800, 1000, 2000, 3000, or 4000 nucleotides. A length of a gene element of FAD2 or FATB can be 50, 75, 100, 150, 175, 200, 220, 250, 300, 320, 350, 400, 420, 450, 500, 550, 600, 800, or 1000 nucleotides.

In another embodiment, the present invention is directed to a method of enhancing oleic acid content and reducing saturated fatty acid content in a plant seed by: i) shortening the length of an exogenous FAD2 DNA sequence in a host cell until the amount of suppression of FAD2 expression from a transformed plant is at least partially reduced relative to the suppression of FAD2 expression in a host cell with a similar genetic background and an entire exogenous FAD2 gene DNA sequence; and ii) growing a plant with a nucleic acid molecule comprising the shortened FAD2 DNA sequence, where the shortened FAD2 DNA sequence at least partially suppresses endogenous expression of FAD2; and iii) cultivating a plant that produces seed with a reduced saturated fatty acid content relative to seed from a plant having a similar genetic background but lacking the shortened FAD2 DNA sequence. The amount that the exogenous FAD2 DNA sequence is shortened to at least partially reduce suppression of the endogenous FAD2 can be determined empirically by introducing different lengths of DNA. For example, the amount of reduction in suppression obtainable by reducing the length of homologous introduced DNA can be determined by deleting increasing portions of the homologous DNA being introduced and assaying for expression of the targeted gene. The amount of suppression of FAD2 expression can be obtained as an average of three or more, six or more, ten or more, fifteen or more, or twenty or more seeds from a plant.

In another embodiment, the present invention is directed to a method of producing a transformed plant having seed with a reduced saturated fatty acid content by transforming a plant cell with a recombinant nucleic acid molecule which comprises a DNA sequence that suppresses the endogenous expression of FAD2 and FATB, where the DNA sequence comprises a nucleic acid sequence of FAD2 that is shorter than the entire sequence of an entire genetic element selected from a gene, an exon, an intron, a transit peptide coding region, and a UTR; and growing the transformed plant, where the transformed plant produces seed with a reduced saturated fatty acid content relative to seed from a plant having a similar genetic background but lacking said recombinant nucleic acid molecule.

In another embodiment, the present invention is directed to a method of modulating the fatty acid composition of oil from a seed of a temperate oilseed crop by isolating a genetic element of at least 40 nucleotides in length that is capable of suppressing the expression of an endogenous gene in the fatty acid synthesis pathway; generating more than one shortened fragment of the genetic element; introducing each of the more than one shortened fragments into a plant cell of the temperate oilseed crop to produce transgenic plants; and selecting a transgenic plant comprising a shortened fragment of determined length and sequence that effects a desirable change in seed oil fatty acid composition. In a preferred embodiment, the method above also includes constructing a recombinant DNA construct having at least two shortened fragments of two different endogenous genes that effect different desirable changes in seed oil fatty acid composition; introducing the recombinant DNA construct into a plant cell of the temperate oilseed crop to produce transgenic plants; and selecting a transgenic plant comprising the at least two shortened fragments and a fatty acid composition of oil from a seed having more than one desirable change effected by the at least two shortened fragments.

In another embodiment, the present invention is directed to a soybean seed exhibiting an oil composition having a strongly reduced saturated fatty acid content and a moderately enhanced oleic acid content having a DNA sequence that suppresses the endogenous expression of FAD2 in a host cell, where the DNA sequence has a nucleic acid sequence of FAD2 that is shorter than the entire sequence of an entire genetic element selected from a gene, an exon, an intron, a transit peptide coding region, and a UTR.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1 Isolation of FATB-2 Sequences

Leaf tissue is obtained from Asgrow soy variety A3244, ground in liquid nitrogen and stored at 80° C. until use. Six ml of SDS Extraction buffer (650 ml sterile ddH20, 100 ml 1M Tris-Cl pH 8, 100 ml 0.25M EDTA, 50 ml 20% SDS, 100 ml 5M NaCl, 4 μl beta-mercaptoethanol) is added to 2 ml of frozen/ground leaf tissue, and the mixture is incubated at 65° C. for 45 minutes. The sample is shaken every 15 minutes. 2 ml of ice-cold 5M potassium acetate is added to the sample, the sample is shaken, and then is incubated on ice for 20 minutes. 3 ml of CHCl₃ is added to the sample and the sample is shaken for 10 minutes.

The sample is centrifuged at 10,000 rpm for 20 minutes and the supernatant is collected. 2 ml of isopropanol is added to the supernatant and mixed. The sample is then centrifuged at 10,000 rpm for 20 minutes and the supernatant is drained. The pellet is resuspended in 200 μl RNase and incubated at 65° C. for 20 minutes. 300 μl ammonium acetate/isopropanol (1:7) is added and mixed. The sample is then centrifuged at 10,000 rpm for 15 minutes and the supernatant is discarded. The pellet is rinsed with 500 μl 80% ethanol and allowed to air dry. The pellet of genomic DNA is then resuspended in 200 μl T10E1 (10 mM Tris:1 mM EDTA).

A soy FATB-2 cDNA contig sequence (SEQ ID NO: 42) is used to design thirteen oligonucleotides that span the gene: F1 (SEQ ID NO: 48), F2 (SEQ ID NO: 49), F3 (SEQ ID NO: 50), F4 (SEQ ID NO: 51), F5 (SEQ ID NO: 52), F6 (SEQ ID NO: 53), F7 (SEQ ID NO: 54), R1 (SEQ ID NO: 55), R2 (SEQ ID NO: 56), R3 (SEQ ID NO: 57), R4 (SEQ ID NO: 58), R5 (SEQ ID NO: 59), and R6 (SEQ ID NO: 60). The oligonucleotides are used in pairs for PCR amplification from the isolated soy genomic DNA: pair 1 (F1+R1), pair 2 (F2+R1), pair 3 (F3+R2), pair 4 (F4+R3), pair 5 (F5+R4), pair 6 (F6+R5), and pair 7 (F7+R6). The PCR amplification for pair 5 is carried out as follows: 1 cycle, 95° C. for 10 minutes; 30 cycles, 95° C. for 15 sec, 43° C. for 30 sec, 72° C. for 45 sec; 1 cycle, 72° C. for 7 minutes. For all other oligo pairs, PCR amplifications are carried out as follows: 1 cycle, 95° C. for 10 minutes; 30 cycles, 95° C. for 15 sec, 48° C. for 30 sec, 72° C. for 45 sec; 1 cycle, 72° C. for 7 minutes. Positive fragments are obtained from primer pairs 1, 2, 4, 5, 6 and 7. Each fragment is cloned into vector pCR2.1 (Invitrogen). Fragments 2, 4, 5 and 6 are confirmed and sequenced. These four sequences are aligned to form a genomic sequence for the FATB-2 gene (SEQ ID NO: 43).

Four introns are identified in the soybean FATB-2 gene by comparison of the genomic sequence to the cDNA sequence: intron I (SEQ ID NO: 44) spans base 119 to base 1333 of the genomic sequence (SEQ ID NO: 43) and is 1215 bp in length; intron II (SEQ ID NO: 45) spans base 2231 to base 2568 of the genomic sequence (SEQ ID NO: 43) and is 338 bp in length; intron III (SEQ ID NO: 46) spans base 2702 to base 3342 of the genomic sequence (SEQ ID NO: 43) and is 641 bp in length; and intron IV (SEQ ID NO: 47) spans base 3457 to base 3823 of the genomic sequence (SEQ ID NO: 43) and is 367 bp in length.

Example 2 Suppression Constructs

2A. FAD2-1 Constructs

The FAD2-1A intron #1 (SEQ ID NO: 1) is cloned into the expression cassette, pCGN3892, in sense and antisense orientations. The vector pCGN3892 contains the soybean 7S promoter and a pea rbcS 3'. Both gene fusions are then separately ligated into pCGN9372, a vector that contains the CP4 EPSPS gene regulated by the FMV promoter. The resulting expression constructs (pCGN5469 sense and pCGN5471 antisense, depicted in FIGS. 1 and 2, respectively) are used for transformation of soybean.

The FAD2-1B intron (SEQ ID NO: 2) is fused to the 3' end of the FAD2-1A intron #1 in plasmid pCGN5468 (contains the soybean 7S promoter fused to the FAD2-1A intron (sense) and a pea rbcS 3') or pCGN5470 (contains the soybean 7S promoter fused to the FAD2-1A intron (antisense) and a pea rbcS 3') in sense and antisense orientation, respectively. The resulting intron combination fusions are then ligated separately into pCGN9372, a vector that contains the CP4 EPSPS gene regulated by the FMV promoter. The resulting expression constructs (pCGN5485, FAD2-1A & FAD2-1B intron sense and pCGN5486, FAD2-1A & FAD2-1B intron antisense) are used for transformation of soybean.

2B. FAD3-1 Constructs

FAD3-1A introns #1, #2, #4 and #5 (SEQ ID NOs: 7, 8, 10 and 11, respectively), FAD3-1B introns #3C (SEQ ID NO: 23) and #4 (SEQ ID NO: 24), are all ligated separately into pCGN3892, in sense or antisense orientation. pCGN3892 contains the soybean 7S promoter and a pea rbcS 3'. These fusions are ligated into pCGN9372, a vector that contains the CP4 EPSPS gene regulated by the FMV promoter for transformation into soybean. The resulting expression constructs (pCGN5455, FAD3-1A intron #4 sense; pCGN5459, FAD3-1A intron #4 antisense; pCGN5456, FAD3 intron #5 sense; pCGN5460, FAD3-1A intron #5 antisense; pCGN5466, FAD3-1A intron #2 antisense; pCGN5473, FAD3-1A intron #1 antisense) are used for transformation of soybean.

2C. FatB Constructs

The soybean FATB-1 intron II sequence (SEQ ID NO: 30) is amplified via PCR using a FATB-1 partial genomic clone as a template. PCR amplification is carried out as follows: 1 cycle, 95° C. for 10 min; 25 cycles, 95° C. for 30 sec, 62° C. for 30 sec, 72° C. for 30 sec; 1 cycle, 72° C. for 7 min. PCR amplification results in a product that is 854 bp long, including reengineered restriction sites at both ends. The PCR product is cloned directly into the expression cassette pCGN3892 in sense orientation, by way of XhoI sites engineered onto the 5' ends of the PCR primers, to form pMON70674. Vector pCGN3892 contains the soybean 7S promoter and a pea rbcS 3'. pMON70674 is then cut with NotI and ligated into pMON41164, a vector that contains the CP4 EPSPS gene regulated by the FMV promoter. The resulting gene expression construct, pMON70678, is used for transformation of soybean using *Agrobacterium* methods.

2D. Combination Constructs

Expression constructs are made containing various permutations of: 1) a FAD2-1 sequences alone (for low linolenic, mid-oleic soybean production methods) and 2) combinations of FAD2-1 and FATB DNA sequences. The DNA sequences are any of those described, or illustrated in Table 2, or any other set of DNA sequences that contain various combinations of sense, antisense, or sense and antisense FAD2 and/or FATB non-coding or coding regions so that they are capable of forming dsRNA constructs, sense co-suppression constructs, antisense constructs, or various combinations of the foregoing.

Figure 4:
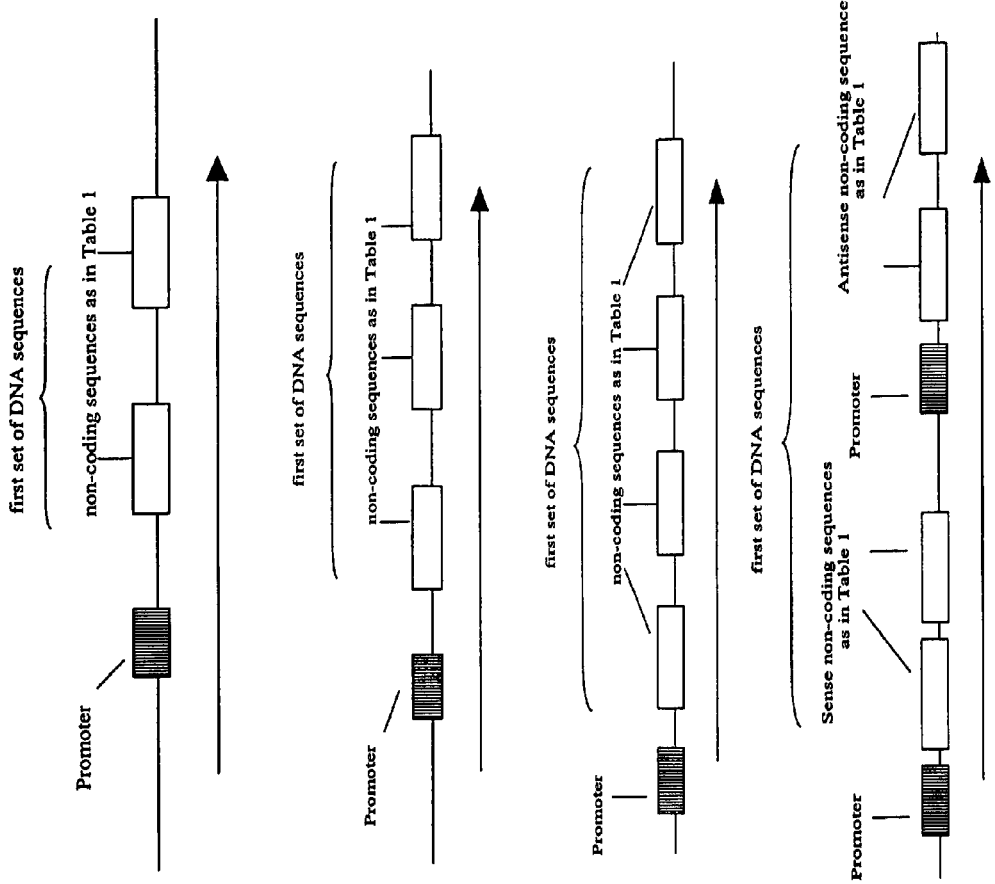
FIG. 4 illustrates exemplary plant vector configurations for decreasing expression of one or more genes by using the DNA sequence elements from the soybean genes listed in Table 1.

FIG. 4 depicts DNA sequences which are capable of expressing sense co-suppression or antisense constructs according to the present invention, the non-coding sequences of which are described in Table 1 and 2 below. The non-coding sequences may be single sequences, combinations of sequences (e.g., the 5'UTR linked to the 3'UTR), or any combination of the foregoing. To express a sense co-suppression construct, all of the non-coding sequences are sense sequences, and to express an antisense construct, all of the non-coding sequences are antisense sequences. To express sense and antisense constructs, both sense and antisense non-coding sequences are provided.

Figure 5:
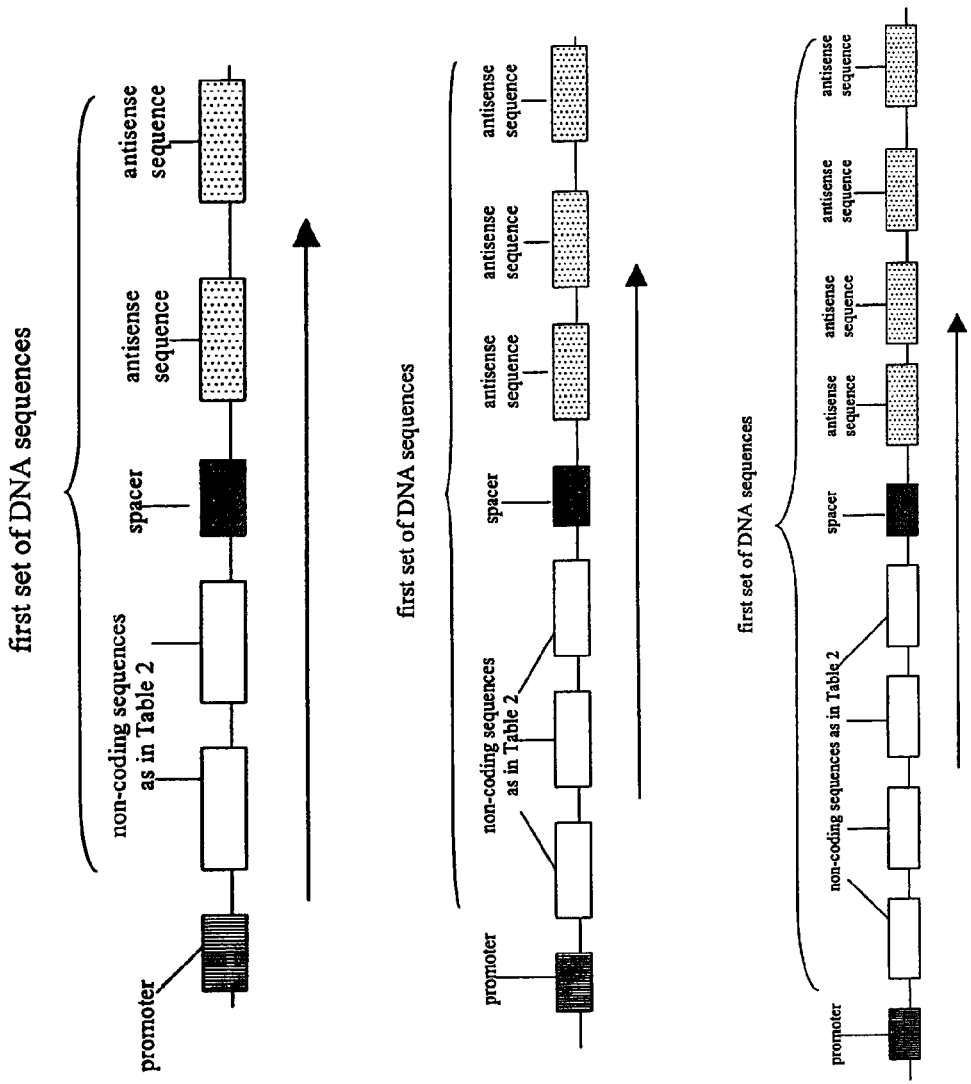
FIG. 5 illustrates exemplary plant vector configurations for decreasing expression of one or more genes by using the DNA sequence elements from the soybean FAD2-1 and/or soybean FATB genes listed in Table 2.
Figure 6:
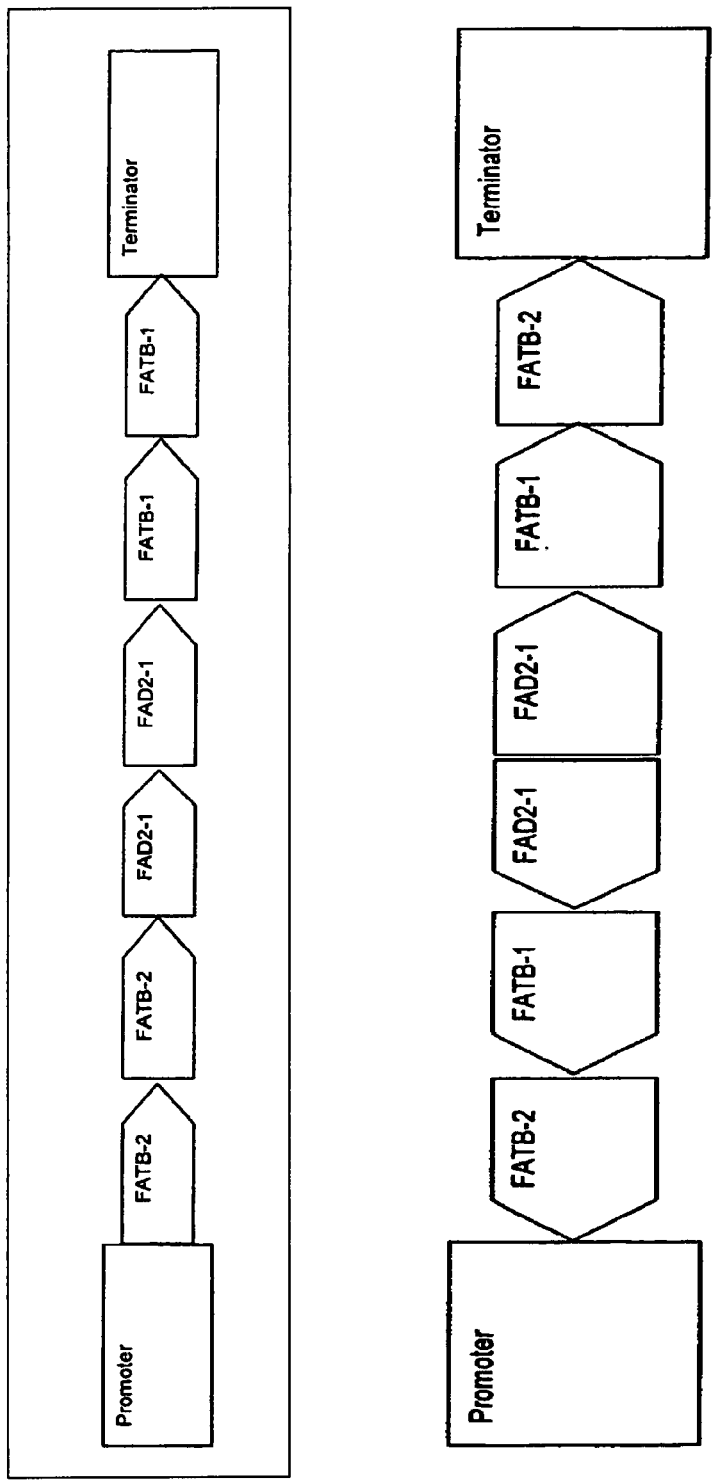
FIG. 6 illustrates exemplary plant vectors for decreasing expression of both the endogenous soybean FAD2-1 and FATB genes.

FIG. 5 depict several first sets of DNA sequences which are capable of expressing dsRNA constructs according to the present invention, the non-coding sequences of which are described in Tables 1 and 2 below. The first set of DNA sequences depicted in FIG. 5 comprises pairs of related sense and antisense sequences, arranged such that, e.g., the RNA expressed by the first sense sequence is capable of forming a double-stranded RNA with the antisense RNA expressed by the first antisense sequence. For example, referring to the topmost vector of FIG. 5 and illustrative combination No. 1 (of Table 1), the first set of DNA sequences comprises a sense FAD2-1 sequence, a sense FAD3-1 sequence, an antisense FAD2-1 sequence and an antisense FAD3-1 sequence. Both antisense sequences correspond to the sense sequences so that the expression products of the first set of DNA sequences are capable of forming a double-stranded RNA with each other. The sense sequences may be separated from the antisense sequences by a spacer sequence, preferably one that promotes the formation of a dsRNA molecule. Examples of such spacer sequences include those set forth in Wesley et al., supra, and Hamilton et al., Plant J., 15:737-746 (1988). The promoter is any promoter functional in a plant, or any plant promoter. Non-limiting examples of suitable promoters are described in Part A of the Detailed Description.

The first set of DNA sequences is inserted in an expression construct in either the sense or anti-sense orientation using a variety of DNA manipulation techniques. If convenient restriction sites are present in the DNA sequences, they are inserted into the expression construct by digesting with the restriction endonucleases and ligation into the construct that has been digested at one or more of the available cloning sites. If convenient restriction sites are not available in the DNA sequences, the DNA of either the construct or the DNA sequences is modified in a variety of ways to facilitate cloning of the DNA sequences into the construct. Examples of methods to modify the DNA include by PCR, synthetic linker or adapter ligation, in vitro site-directed mutagenesis, filling in or cutting back of overhanging 5' or 3' ends, and the like. These and other methods of manipulating DNA are well known to those of ordinary skill in the art.

TABLE 1

| Illustrative Combinations | Non-Coding or Coding Sequences (sense or antisense) | | | |
|---|---|---|---|---|
| | First | Second | Third | Fourth |
| 1 | FAD2-1A or B | FAD3-1A or B or C | | |
| 2 | FAD3-1A or B or C | FAD2-1A or B | | |
| 3 | FAD2-1A or B | FAD3-1A or B or C | different FAD3-1A or B or C sequence | |
| 4 | FAD2-1A or B | FAD3-1A or B or C | FATB-1 | |
| 5 | FAD2-1A or B | FATB-1 | FAD3-1A or B or C | |
| 6 | FAD3-1A or B or C | FAD2-1A or B | FATB-1 | |
| 7 | FAD3-1A or B or C | FATB-1 | FAD2-1A or B | |
| 8 | FATB-1 | FAD3-1A or B or C | FAD2-1A or B | |
| 9 | FATB-1 | FAD2-1A or B | FAD3-1A or B or C | |
| 10 | FAD2-1A or B | FAD3-1A or B or C | different FAD3-1A or B or C sequence | FATB-1 |
| 11 | FAD3-1A or B or C | FAD2-1A or B | different FAD3-1A or B or C sequence | FATB-1 |
| 12 | FAD3-1A or B or C | different FAD3-1A or B or C sequence | FAD2-1A or B | FATB-1 |
| 13 | FAD2-1A or B | FAD3-1A or B or C | FATB-1 | different FAD3-1A or B or C sequence |
| 14 | FAD3-1A or B or C | FAD2-1A or B | FATB-1 | different FAD3-1A or B or C sequence |
| 15 | FAD3-1A or B or C | different FAD3-1A or B or C sequence | FATB-1 | FAD2-1A or B |
| 16 | FAD2-1A or B | FATB-1 | FAD3-1A or B or C | different FAD3-1A or B or C sequence |
| 17 | FAD3-1A or B or C | FATB-1 | FAD2-1A or B | different FAD3-1A or B or C sequence |
| 18 | FAD3-1A or B or C | FATB-1 | different FAD3-1A or B or C sequence | FAD2-1A or B |
| 19 | FATB-1 | FAD2-1A or B | FAD3-1A or B or C | different FAD3-1A or B or C sequence |
| 20 | FATB-1 | FAD3-1A or B or C | FAD2-1A or B | different FAD3-1A or B or C sequence |
| 21 | FATB-1 | FAD3-1A or B or C | different FAD3-1A or B or C sequence | FAD2-1A or B |
| 22 | FAD2-1A or B | FAD3-1A or B or C | FATB-2 | |
| 23 | FAD2-1A or B | FATB-2 | FAD3-1A or B or C | |
| 24 | FAD3-1A or B or C | FAD2-1A or B | FATB-2 | |
| 25 | FAD3-1A or B or C | FATB-2 | FAD2-1A or B | |
| 26 | FATB-2 | FAD3-1A or B or C | FAD2-1A or B | |
| 27 | FATB-2 | FAD2-1A or B | FAD3-1A or B or C | |
| 28 | FAD2-1A or B | FAD3-1A or B or C | different FAD3-1A or B or C sequence | FATB-2 |
| 29 | FAD3-1A or B or C | FAD2-1A or B | different FAD3-1A or B or C sequence | FATB-2 |
| 30 | FAD3-1A or B or C | different FAD3-1A or B or C sequence | FAD2-1A or B | FATB-2 |
| 31 | FAD2-1A or B | FAD3-1A or B or C | FATB-2 | different FAD3-1A or B or C sequence |

TABLE 1-continued

| Illustrative Combinations | Non-Coding or Coding Sequences (sense or antisense) | | | |
|---|---|---|---|---|
| | First | Second | Third | Fourth |
| 32 | FAD3-1A or B or C | FAD2-1A or B | FATB-2 | different FAD3-1A or B or C sequence |
| 33 | FAD3-1A or B or C | different FAD3-1A or B or C sequence | FATB-2 | FAD2-1A or B |
| 34 | FAD2-1A or B | FATB-2 | FAD3-1A or B or C | different FAD3-1A or B or C sequence |
| 35 | FAD3-1A or B or C | FATB-2 | FAD2-1A or B | different FAD3-1A or B or C sequence |
| 36 | FAD3-1A or B or C | FATB-2 | different FAD3-1A or B or C sequence | FAD2-1A or B |
| 37 | FATB-2 | FAD2-1A or B | FAD3-1A or B or C | different FAD3-1A or B or C sequence |
| 38 | FATB-2 | FAD3-1A or B or C | FAD2-1A or B | different FAD3-1A or B or C sequence |
| 39 | FATB-2 | FAD3-1A or B or C | different FAD3-1A or B or C sequence | FAD2-1A or B |
| 40 | FAD2-1A or B | FATB-1 | | |
| 41 | FAD2-1A or B | FATB-2 | | |
| 42 | FAD2-1A or B | FATB-1 | FATB-2 | |
| 43 | FAD2-1A | FAD2-1B | FATB-1 | |
| 44 | FAD2-1A | FAD2-1B | FATB-1 | FATB-2 |
| 45 | FAD2-1A or B | FAD2-1A or B | | |
| 46 | FATB-1 or FATB-2 | FATB-1 or FATB-2 | | |

TABLE 2

Correlation of SEQ ID NOs with Sequences in Table 1

| | FAD2-1A | FAD2-1B | FAD3-1A | FAD3-1B | FAD3-1C | FATB-1 | FATB-2 |
|---|---|---|---|---|---|---|---|
| 3'UTR | SEQ NO: 5 | n/a | SEQ NO: 16 | SEQ NO: 26 | n/a | SEQ NO: 36 | n/a |
| 5'UTR | SEQ NO: 6 | n/a | SEQ NO: 17 | SEQ NO: 27 | n/a | SEQ NO: 37 | n/a |
| 5' + 3' UTR (or 3' + 5' UTR) | Linked SEQ NOs: 5 and 6 | n/a | Linked SEQ NOs: 16 and 17 | Linked SEQ NOs: 26 and 27 | n/a | Linked SEQ NOs: 36 and 37 | n/a |
| Intron #1 | SEQ NO: 1 | SEQ NO: 2 | SEQ NO: 7 | SEQ NO: 19 | n/a | SEQ NO: 29 | SEQ NO: 44 |
| Intron #2 | n/a | n/a | SEQ NO: 8 | SEQ NO: 20 | n/a | SEQ NO: 30 | SEQ NO: 45 |
| Intron #3 | n/a | n/a | n/a | n/a | n/a | SEQ NO: 31 | SEQ NO: 46 |
| Intron #3A | n/a | n/a | SEQ NO: 9 | SEQ NO: 21 | n/a | n/a | n/a |
| Intron #3B | n/a | n/a | SEQ NO: 12 | SEQ NO: 22 | n/a | n/a | n/a |
| Intron #3C | n/a | n/a | SEQ NO: 13 | SEQ NO: 23 | n/a | n/a | n/a |
| Intron #4 | n/a | n/a | SEQ NO: 10 | SEQ NO: 24 | SEQ NO: 14 | SEQ NO: 32 | SEQ NO: 47 |
| Intron #5 | n/a | n/a | SEQ NO: 11 | SEQ NO: 25 | n/a | SEQ NO: 33 | n/a |
| Intron #6 | n/a | n/a | n/a | n/a | n/a | SEQ NO: 34 | n/a |
| Intron #7 | n/a | n/a | n/a | n/a | n/a | SEQ NO: 35 | n/a |

Example 3

3A. Antisense Constructs

Referring now to FIG. 7, soybean FATB-2 non-coding sequences (SEQ ID NOs: 44-47), FATB-1 non-coding sequences (SEQ ID NOs: 29-37), and FAD2-1 non-coding sequences (SEQ ID NOs: 1 and 5-6) are amplified via PCR to result in PCR products that include reengineered restriction sites at both ends. The PCR products are cloned directly in sense and antisense orientation into a vector containing the soybean 7Sα' promoter and a tml 3' termination sequence. The vector is then cut with an appropriate restriction endonuclease and ligated into pMON80612 a vector that contains the CP4 EPSPS gene regulated by the FMV promoter and a pea Rubisco E9 3' termination sequence. The resulting gene expression construct is depicted in the bottom most construct of FIG. 7 and is used for transformation using methods as described herein.

3B. In Vivo Assembly

An aspect of the present invention includes a DNA construct that assembles into a recombinant transcription unit on a plant chromosome in planta that is capable of forming double-stranded RNA. The assembly of such constructs and the methods for assembling in vivo a recombinant transcription units for gene suppression are described in International Application No. PCT/US2005/00681, hereby incorporated by reference in its entirety.

pMON95829 is a construct used for in vivo assembly that has two T-DNA segments, each flanked by *Agrobacterium* T-DNA border elements, i.e. right border DNA (RB) and left border DNA (LB). The first T-DNA contains a soybean 7Sα' promoter operably linking to a soybean FAD2-1A intron 1 (SEQ ID NO: 1), which is reduced by 100 contiguous nucleotides from the 3' end and ligated to 42 contiguous nucleotides of a FATB-1a 5' UTR, followed by the FATB-1A chloroplast transit peptide ("CTP") coding region, and a CP4 EPSPS gene operably linking to an enhanced FMV promoter and a pea Rubisco E9 3' termination sequence all flanked by *Agrobacterium* T-DNA border elements, i.e. right border DNA (RB) and left border DNA (LB). On the same vector in the second T-DNA segment, flanked by another RB and LB, is a H6 3' termination sequence operably linking to a soybean FAD2-1A intron 1 (SEQ ID NO: 1), which is reduced by 100 contiguous nucleotides from the 3' end and ligated to 42 contiguous nucleotides of a FATB-1a 5' UTR, followed by the FATB-1A chloroplast transit peptide ("CTP") coding region. The resulting gene expression construct is used for transformation using methods as described herein.

pMON97595 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to 42 contiguous nucleotides of a FATB-1a 5' UTR followed by the FATB-1a chloroplast transit peptide ("CTP") coding region, and a CP4 EPSPS gene operably linking to an enhanced FMV promoter and a pea rubisco E9 3' termination sequence, all flanked by *Agrobacterium* T-DNA border elements, i.e. right border DNA (RB) and left border DNA (LB). On the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to 42 contiguous nucleotides of a FATB-1a5' UTR followed by the FATB-1A CTP coding region. The resulting gene expression construct is used for transformation using methods as described herein.

pMON97581 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to the FATB-1a chloroplast transit peptide ("CTP") coding region, and a CP4 EPSPS gene operably linking to an enhanced FMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to the FATB-1a CTP coding region. The resulting gene expression construct is used for transformation using methods as described herein.

pMON97596 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to the 5' 180 bp of the FATB-1a chloroplast transit peptide ("CTP") coding region, and a CP4 EPSPS gene operably linking to an enhanced FMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to the 5' 180 bp of the FATB-1a CTP coding region. The resulting gene expression construct is used for transformation using methods as described herein.

pMON97597 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to the 5' 120 bp of the FATB-1a chloroplast transit peptide ("CTP") coding region, and a CP4 EPSPS gene operably linking to an enhanced FMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to the 5' 120 bp of the FATB-1a CTP coding region. The resulting gene expression construct is used for transformation using methods as described herein.

pMON97598 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 340 contiguous nucleotides from the 3' end and ligated to the FATB-1a chloroplast transit peptide ("CTP") coding region, and a CP4 EPSPS gene operably linking to an enhanced FMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 340 contiguous nucleotides from the 3' end and ligated to the FATB-1a CTP coding region. The resulting gene expression construct is used for transformation using methods as described herein.

When the two T-DNA segments of the any one of the above constructs (i.e. pMON95829, pMON97595, pMON97581, pMON97597, pMON97598) are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

Example 4 Plant Transformation and Analysis

The constructs of Examples 2 and 3 are stably introduced into soybean (for example, Asgrow variety A4922 or Asgrow variety A3244 or Asgrow variety A3525) by the methods described earlier, including the methods of McCabe et al., Bio/Technology, 6:923-926 (1988), or *Agrobacterium*-mediated transformation. Transformed soybean plants are identified by selection on media containing a selectable agent or herbicide. The herbicide can be glyphosate when a transgene conferring resistance to glyphosate is used. Fatty acid compositions are analyzed from seed of soybean lines transformed with the constructs using gas chromatography.

For some applications, modified fatty acid compositions are detected in developing seeds, whereas in other instances, such as for analysis of oil profile, detection of fatty acid modifications occurring later in the FAS pathway, or for detection of minor modifications to the fatty acid composition, analysis of fatty acid or oil from mature seeds is performed. Furthermore, analysis of oil and/or fatty acid content of individual seeds may be desirable, especially in detection of oil modification in the segregating R1 seed populations. As used herein, R0 generation indicates the plant arising from transformation/regeneration protocols described herein, the R1 generation indicates seeds grown on the selfed transgenic R0 plant. R1 plants are grown from the R1 seeds.

Fatty acid compositions are determined for the seed of soybean lines transformed with the constructs of Example 3. One to ten seeds of each of the transgenic and control soybean lines are ground individually using a tissue homogenizer (Pro Scientific) for oil extraction. Oil from ground soybean seed is extracted overnight in 1.5 ml heptane containing triheptadecanoin (0.50 mg/ml). Aliquots of 200 µl of the extracted oil are derivatized to methyl esters with the addition of 500 µl sodium methoxide in absolute methanol. The derivatization reaction is allowed to progress for 20 minutes at 50° C. The reaction is stopped by the simultaneous addition of 500 µl 10% (w/v) sodium chloride and 400 µl heptane. The resulting fatty acid methyl esters extracted in hexane are resolved by gas chromatography (GC) on a Hewlett-Packard model 6890 GC (Palo Alto, Calif.). The GC was fitted with a Supelcowax 250 column (30 m, 0.25 mm id, 0.25 micron film thickness) (Supelco, Bellefonte, Pa.). Column temperature is 175° C. at injection and the temperature programmed from 175° C. to 245° C. to 175° C. at 40° C./min. Injector and detector temperatures are 250° C. and 270° C., respectively.

Example 5

This example illustrates plant transformation to produce soybean plants with suppressed genes.

A transformation vector pMON68537 is used to introduce an intron/3'UTR double-stranded RNA-forming construct into soybean for suppressing the Δ12 desaturase, Δ15 desaturase, and FATB genes. Vector pMON68537 also contains the delta-9 desaturase (FAB2) and the CP4 genes. The pMON68537 vector is designed for plant transformation to suppress FAD2, FAD3, and FATB genes and overexpress delta-9 desaturase in soybean. In particular, the construct comprises a 7S alpha promoter operably linked to soybean sense-oriented intron and 3'UTRs, i.e., a FAD2-1A intron #1, a FAD3-1A 3'UTR, a FATB-1 3'UTR, a hairpin loop-forming spliceable intron, and a complementary series of soybean anti-sense-oriented intron and 3'UTR's, i.e., a FATB-1 3'UTR, a FAD3-1A 3'UTR and a FAD2-1A intron #1 and the soybean FAD2 promoter driving the delta-9 desaturase. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with the intron/3'UTR dsRNAi expression constructs using gas chromatography. R1 pooled seed and R1 single seed oil compositions demonstrate that the mono- and polyunsaturated fatty acid compositions are altered in the oil of seeds from transgenic soybean lines as compared to that of the seed from non-transformed soybean, (See Table 3). For instance, FAD2 suppression provides plants with increased amount of oleic acid ester compounds; FAD3 suppression provides plants with decreased linolenic acid ester compounds; and FATB suppression provides plants with reduced saturated fatty ester compounds, e.g. palmitates and stearates. Selections can be made from such lines depending on the desired relative fatty acid composition. Fatty acid compositions are analyzed from seed of soybean lines transformed with constructs using gas chromatography.

TABLE 3

Fatty acid composition of R1 single seeds from pMON68537 Events

| Construct | Event | 18:1 | 18:3 | 16:0 | 18:0 | 18:2 |
|---|---|---|---|---|---|---|
| PMON68537 | GM_A36305 | 74.92 | 4.42 | 6.35 | 2.93 | 10.24 |
| PMON68537 | GM_A36305 | 74.8 | 4.33 | 6.57 | 2.93 | 10.23 |
| PMON68537 | GM_A36305 | 74.43 | 3.95 | 5.98 | 2.82 | 11.81 |
| PMON68537 | GM_A36305 | 73.32 | 3.99 | 6.79 | 3.24 | 11.48 |
| PMON68537 | GM_A36305 | 72.87 | 4.33 | 7.06 | 3.08 | 11.7 |
| PMON68537 | GM_A36305 | 16.63 | 9.53 | 13.5 | 4.06 | 55.31 |
| PMON68537 | GM_A36305 | 16.52 | 9.61 | 13.92 | 4.24 | 54.79 |
| PMON68537 | GM_A36305 | 15.67 | 9.66 | 13.64 | 4.19 | 55.89 |
| PMON68537 | GM_A36306 | 77.45 | 3.93 | 6.76 | 2.47 | 8.4 |
| PMON68537 | GM_A36306 | 74.51 | 4.38 | 6.58 | 2.47 | 10.94 |
| PMON68537 | GM_A36306 | 73.21 | 4.64 | 7.04 | 3.08 | 11.04 |
| PMON68537 | GM_A36306 | 72.78 | 4.4 | 6.97 | 2.55 | 12.21 |
| PMON68537 | GM_A36306 | 71.67 | 4.76 | 6.94 | 3.25 | 12.2 |
| PMON68537 | GM_A36306 | 71.01 | 4.86 | 7.64 | 3.05 | 12.41 |
| PMON68537 | GM_A36306 | 69.72 | 4.76 | 7.66 | 2.95 | 13.75 |
| PMON68537 | GM_A36306 | 17.41 | 8.88 | 13.35 | 3.85 | 55.63 |
| PMON68537 | GM_A36307 | 77.22 | 3.71 | 6.8 | 2.77 | 8.5 |
| PMON68537 | GM_A36307 | 76.79 | 3.65 | 6.76 | 2.85 | 8.75 |
| PMON68537 | GM_A36307 | 71.44 | 4.54 | 7.2 | 3.58 | 12.17 |
| PMON68537 | GM_A36307 | 18.83 | 8.62 | 13.94 | 4.02 | 53.61 |
| PMON68537 | GM_A36307 | 18.81 | 8.38 | 13.27 | 3.7 | 54.97 |
| PMON68537 | GM_A36307 | 15.68 | 9.97 | 14.06 | 4.55 | 54.79 |
| PMON68537 | GM_A36307 | 15.28 | 10.64 | 14.68 | 4.43 | 53.97 |
| PMON68537 | GM_A36307 | 14.08 | 9.36 | 14.39 | 4.31 | 56.89 |
| PMON68537 | GM_A36309 | 78.67 | 3.53 | 6.09 | 2.5 | 8.18 |
| PMON68537 | GM_A36309 | 75.43 | 3.96 | 6.7 | 2.53 | 10.3 |
| PMON68537 | GM_A36309 | 71.41 | 4.19 | 6.92 | 2.74 | 13.67 |
| PMON68537 | GM_A36309 | 70.51 | 4.14 | 6.85 | 3.16 | 14.33 |
| PMON68537 | GM_A36309 | 67.51 | 5.01 | 7.45 | 3.15 | 15.69 |
| PMON68537 | GM_A36309 | 66.99 | 4.92 | 7.15 | 3.9 | 15.79 |
| PMON68537 | GM_A36309 | 20.09 | 8.46 | 12.41 | 5 | 52.97 |
| PMON68537 | GM_A36309 | 15.15 | 9.73 | 14.61 | 3.85 | 55.79 |
| PMON68537 | GM_A36310 | 74.28 | 4.77 | 7.31 | 1.85 | 10.9 |
| PMON68537 | GM_A36310 | 74.03 | 5.43 | 8.23 | 1.63 | 9.66 |
| PMON68537 | GM_A36310 | 73.07 | 5.09 | 7.37 | 1.76 | 11.75 |
| PMON68537 | GM_A36310 | 71.83 | 5.04 | 7.78 | 1.86 | 12.54 |

TABLE 3-continued

Fatty acid composition of R1 single seeds from pMON68537 Events

| Construct | Event | 18:1 | 18:3 | 16:0 | 18:0 | 18:2 |
|---|---|---|---|---|---|---|
| PMON68537 | GM_A36310 | 68.01 | 6.26 | 9.8 | 1.97 | 13.13 |
| PMON68537 | GM_A36310 | 67.22 | 6.28 | 8.71 | 3.28 | 13.45 |
| PMON68537 | GM_A36310 | 65.37 | 6.87 | 10.01 | 1.94 | 14.9 |
| PMON68537 | GM_A36310 | 15.76 | 10.09 | 13.4 | 4.28 | 55.52 |
| PMON68537 | GM_A36311 | 77.87 | 3.56 | 5.9 | 2.46 | 9.05 |
| PMON68537 | GM_A36311 | 75.8 | 3.87 | 5.91 | 2.93 | 10.22 |
| PMON68537 | GM_A36311 | 75.61 | 3.71 | 6.21 | 2.56 | 10.75 |
| PMON68537 | GM_A36311 | 73.68 | 4.06 | 6 | 3.09 | 11.98 |
| PMON68537 | GM_A36311 | 72.66 | 4.11 | 6.41 | 3.14 | 12.48 |
| PMON68537 | GM_A36311 | 70.89 | 4.39 | 6.52 | 3.11 | 13.93 |
| PMON68537 | GM_A36311 | 70.82 | 3.97 | 6.52 | 3.18 | 14.29 |
| PMON68537 | GM_A36311 | 16.67 | 9.39 | 13.65 | 4.44 | 54.77 |
| PMON68537 | GM_A36312 | 78.32 | 4.3 | 6.36 | 1.79 | 8.16 |
| PMON68537 | GM_A36312 | 77.55 | 4.46 | 6.51 | 2.13 | 8.23 |
| PMON68537 | GM_A36312 | 77.43 | 4.17 | 6.31 | 1.81 | 9.24 |
| PMON68537 | GM_A36312 | 76.98 | 4.29 | 6.25 | 2.27 | 9.05 |
| PMON68537 | GM_A36312 | 76.43 | 4.55 | 6.82 | 2.16 | 8.96 |
| PMON68537 | GM_A36312 | 76.38 | 4.5 | 6.46 | 2.04 | 9.54 |
| PMON68537 | GM_A36312 | 75.25 | 4.27 | 6.41 | 1.97 | 11.06 |
| PMON68537 | GM_A36312 | 18.24 | 9.43 | 13.6 | 3.07 | 54.75 |
| PMON68537 | GM_A36313 | 80.18 | 4.07 | 6.17 | 2.59 | 5.85 |
| PMON68537 | GM_A36313 | 79.96 | 4.16 | 6.03 | 2.59 | 6.11 |
| PMON68537 | GM_A36313 | 78.88 | 3.9 | 5.6 | 2.8 | 7.65 |
| PMON68537 | GM_A36313 | 78.76 | 3.92 | 5.44 | 2.91 | 7.82 |
| PMON68537 | GM_A36313 | 77.64 | 4.22 | 5.88 | 2.9 | 8.25 |
| PMON68537 | GM_A36313 | 76.15 | 4.14 | 6.06 | 3.13 | 9.42 |
| PMON68537 | GM_A36313 | 19.05 | 8.87 | 13.45 | 3.71 | 54.03 |
| PMON68537 | GM_A36313 | 18.47 | 8.46 | 13.13 | 3.63 | 55.41 |
| PMON68537 | GM_A36314 | 80.27 | 3.17 | 5.77 | 3.4 | 6.03 |
| PMON68537 | GM_A36314 | 79.66 | 3.24 | 5.72 | 3.19 | 6.91 |
| PMON68537 | GM_A36314 | 79.5 | 3.45 | 5.83 | 3.23 | 6.74 |
| PMON68537 | GM_A36314 | 77.42 | 3.52 | 5.76 | 3.57 | 8.42 |
| PMON68537 | GM_A36314 | 77.33 | 3.71 | 6.36 | 3.34 | 8.01 |
| PMON68537 | GM_A36314 | 76.83 | 3.71 | 6.38 | 3.24 | 8.59 |
| PMON68537 | GM_A36314 | 16.6 | 9.3 | 12.63 | 4.43 | 55.99 |
| PMON68537 | GM_A36314 | 15.26 | 8.59 | 13.71 | 4.54 | 56.84 |
| PMON68537 | GM_A36315 | 20.21 | 8.25 | 13.61 | 3.59 | 53.37 |
| PMON68537 | GM_A36315 | 17.47 | 9.22 | 13.46 | 3.35 | 55.57 |
| PMON68537 | GM_A36315 | 16.75 | 9.3 | 13.61 | 3.66 | 55.75 |
| PMON68537 | GM_A36315 | 16.54 | 9.18 | 13.54 | 3.88 | 55.9 |
| PMON68537 | GM_A36315 | 16.06 | 10.07 | 13.44 | 4.01 | 55.42 |
| PMON68537 | GM_A36315 | 16.05 | 9.58 | 12.82 | 4.25 | 56.29 |
| PMON68537 | GM_A36315 | 15.95 | 10.42 | 13.12 | 3.63 | 55.91 |
| PMON68537 | GM_A36315 | 15.5 | 10.22 | 13.25 | 3.78 | 56.3 |
| PMON68537 | GM_A36316 | 79.61 | 3.56 | 5.79 | 2.94 | 6.87 |
| PMON68537 | GM_A36316 | 75.11 | 4.01 | 6.45 | 3.44 | 9.76 |
| PMON68537 | GM_A36316 | 75.07 | 4.25 | 6.74 | 3.09 | 9.64 |
| PMON68537 | GM_A36316 | 73.92 | 3.97 | 6.53 | 3.56 | 10.75 |
| PMON68537 | GM_A36316 | 17.26 | 9.59 | 13.1 | 4.26 | 54.78 |
| PMON68537 | GM_A36316 | 17.15 | 9.03 | 12.81 | 4.04 | 55.97 |
| PMON68537 | GM_A36316 | 16.62 | 9.2 | 13.15 | 3.99 | 56.03 |
| PMON68537 | GM_A36316 | 16.6 | 9.44 | 13.19 | 3.95 | 55.84 |
| PMON68537 | GM_A36317 | 18.96 | 7.55 | 13.2 | 3.75 | 55.51 |
| PMON68537 | GM_A36317 | 16.19 | 9.43 | 13.33 | 3.96 | 56.04 |
| PMON68537 | GM_A36317 | 16.05 | 9.1 | 14.02 | 3.94 | 55.91 |
| PMON68537 | GM_A36317 | 15.33 | 9.4 | 13.91 | 4.22 | 56.11 |
| PMON68537 | GM_A36317 | 15.28 | 9.2 | 13.87 | 4.27 | 56.36 |
| PMON68537 | GM_A36317 | 14.58 | 10.15 | 13.74 | 4.38 | 56.15 |
| PMON68537 | GM_A36317 | 13.95 | 9.47 | 13.98 | 4.76 | 56.79 |
| PMON68537 | GM_A36317 | 13.91 | 9.88 | 14.26 | 4.62 | 56.25 |
| PMON68537 | GM_A36318 | 78.82 | 3.64 | 5.7 | 2.77 | 7.87 |
| PMON68537 | GM_A36318 | 77.94 | 3.73 | 5.9 | 2.94 | 8.29 |
| PMON68537 | GM_A36318 | 75.18 | 4.11 | 6.08 | 3.48 | 9.95 |
| PMON68537 | GM_A36318 | 75.1 | 3.93 | 6.02 | 3.04 | 10.75 |
| PMON68537 | GM_A36318 | 75.01 | 4.22 | 6.57 | 3.29 | 9.72 |
| PMON68537 | GM_A36318 | 74.17 | 4.2 | 6.51 | 3.27 | 10.68 |
| PMON68537 | GM_A36318 | 73.47 | 4.27 | 6.37 | 3.22 | 11.16 |
| PMON68537 | GM_A36318 | 30.57 | 10.54 | 14.83 | 5.55 | 36.92 |
| PMON68537 | GM_A36319 | 80 | 3.65 | 5.83 | 2.31 | 7.02 |
| PMON68537 | GM_A36319 | 79.89 | 3.65 | 5.64 | 2.35 | 7.26 |
| PMON68537 | GM_A36319 | 79.4 | 3.59 | 5.73 | 1.76 | 8.46 |
| PMON68537 | GM_A36319 | 78 | 3.87 | 6.11 | 2.35 | 8.5 |
| PMON68537 | GM_A36319 | 76.08 | 4.22 | 6.5 | 2.35 | 9.74 |
| PMON68537 | GM_A36319 | 75.56 | 3.89 | 6.41 | 1.78 | 11.3 |
| PMON68537 | GM_A36319 | 75.26 | 4.27 | 6.47 | 2.37 | 10.5 |
| PMON68537 | GM_A36319 | 75.16 | 4.1 | 6.48 | 2.49 | 10.66 |
| PMON68537 | GM_A36320 | 81.27 | 3.19 | 5.84 | 2.4 | 6.09 |
| PMON68537 | GM_A36320 | 80.21 | 3.27 | 5.18 | 2.44 | 7.76 |
| PMON68537 | GM_A36320 | 79.64 | 3.38 | 5.5 | 2.67 | 7.63 |
| PMON68537 | GM_A36320 | 79.46 | 3.38 | 5.82 | 2.67 | 7.42 |
| PMON68537 | GM_A36320 | 78.5 | 3.59 | 6.24 | 2.49 | 8 |
| PMON68537 | GM_A36320 | 73.83 | 3.79 | 6.72 | 2.78 | 11.74 |
| PMON68537 | GM_A36320 | 73.1 | 3.95 | 6.9 | 2.39 | 12.48 |
| PMON68537 | GM_A36320 | 22.99 | 8.03 | 12.19 | 4.81 | 50.89 |
| PMON68537 | GM_A36324 | 75.93 | 3.77 | 6.58 | 2.76 | 9.76 |
| PMON68537 | GM_A36324 | 75.1 | 4.05 | 7.01 | 2.83 | 9.8 |
| PMON68537 | GM_A36324 | 17.83 | 8.79 | 12.78 | 4.11 | 55.49 |
| PMON68537 | GM_A36324 | 16.46 | 8.88 | 12.84 | 4.48 | 56.29 |
| PMON68537 | GM_A36324 | 16.35 | 9.25 | 13.51 | 4.17 | 55.66 |
| PMON68537 | GM_A36324 | 15.25 | 8.99 | 13.73 | 4.28 | 56.69 |
| PMON68537 | GM_A36324 | 14.16 | 10.17 | 13.95 | 4.11 | 56.58 |
| PMON68537 | GM_A36324 | 13.59 | 9.87 | 14.61 | 4.5 | 56.33 |
| PMON68537 | GM_A36357 | 80.19 | 3.03 | 5.59 | 3.2 | 6.62 |
| PMON68537 | GM_A36357 | 79.78 | 3.19 | 5.51 | 3.24 | 6.89 |
| PMON68537 | GM_A36357 | 78.5 | 3.55 | 5.75 | 3.17 | 7.71 |
| PMON68537 | GM_A36357 | 77.48 | 3.68 | 5.71 | 3.55 | 8.23 |
| PMON68537 | GM_A36357 | 77.28 | 3.79 | 5.66 | 3.48 | 8.46 |
| PMON68537 | GM_A36357 | 77.1 | 3.51 | 5.43 | 3.65 | 8.99 |
| PMON68537 | GM_A36357 | 71.9 | 4.24 | 6.47 | 3.67 | 12.39 |
| PMON68537 | GM_A36357 | 17.66 | 9.32 | 13.26 | 4.21 | 54.51 |
| PMON68537 | GM_A36359 | 77.91 | 3.35 | 5.67 | 3.24 | 8.53 |
| PMON68537 | GM_A36359 | 77.85 | 3.29 | 5.42 | 3.29 | 8.87 |
| PMON68537 | GM_A36359 | 76.71 | 3.65 | 6.07 | 3.35 | 8.95 |
| PMON68537 | GM_A36359 | 71.73 | 4.01 | 6.79 | 3.49 | 12.68 |
| PMON68537 | GM_A36359 | 69.32 | 4.51 | 6.99 | 3.66 | 14.13 |
| PMON68537 | GM_A36359 | 68.63 | 4.44 | 6.91 | 3.76 | 14.89 |
| PMON68537 | GM_A36359 | 18.87 | 8.03 | 13.38 | 3.86 | 54.81 |
| PMON68537 | GM_A36359 | 16.81 | 9.83 | 13.08 | 4.68 | 54.55 |
| PMON68537 | GM_A36360 | 79.34 | 3.29 | 5.99 | 3.15 | 6.88 |
| PMON68537 | GM_A36360 | 75.42 | 3.47 | 6.47 | 3.08 | 10.26 |
| PMON68537 | GM_A36360 | 75.3 | 3.86 | 6.69 | 3.2 | 9.64 |
| PMON68537 | GM_A36360 | 74.51 | 3.8 | 6.39 | 3.32 | 10.67 |
| PMON68537 | GM_A36360 | 21.49 | 6.95 | 13.07 | 3.92 | 53.46 |
| PMON68537 | GM_A36360 | 20.05 | 7.4 | 13.09 | 3.83 | 54.57 |
| PMON68537 | GM_A36360 | 16.08 | 9.14 | 13.02 | 4.64 | 56.03 |
| PMON68537 | GM_A36360 | 15.86 | 9.07 | 13.44 | 4.49 | 56.04 |
| PMON68537 | GM_A36361 | 82.13 | 2.83 | 5.67 | 3.13 | 4.81 |
| PMON68537 | GM_A36361 | 80.99 | 3.2 | 5.79 | 3.01 | 5.64 |
| PMON68537 | GM_A36361 | 74.39 | 3.85 | 6.33 | 3.5 | 10.59 |
| PMON68537 | GM_A36361 | 18.01 | 8.46 | 13.18 | 3.92 | 55.41 |
| PMON68537 | GM_A36361 | 17.99 | 8.11 | 13.05 | 4.09 | 55.7 |
| PMON68537 | GM_A36361 | 17.35 | 8.31 | 13.4 | 4 | 55.88 |
| PMON68537 | GM_A36361 | 16.81 | 10.2 | 12.9 | 4.32 | 54.87 |
| PMON68537 | GM_A36361 | 16.55 | 8.5 | 13.21 | 4.22 | 56.45 |
| PMON68537 | GM_A36362 | 78.05 | 3.89 | 6.29 | 2.81 | 7.76 |
| PMON68537 | GM_A36362 | 76.89 | 3.69 | 6.32 | 3.12 | 8.76 |
| PMON68537 | GM_A36362 | 76.1 | 4 | 6.57 | 3.02 | 9.24 |
| PMON68537 | GM_A36362 | 76.01 | 4.08 | 6.24 | 3.03 | 9.48 |
| PMON68537 | GM_A36362 | 75.86 | 3.76 | 5.68 | 3.56 | 9.95 |
| PMON68537 | GM_A36362 | 75.79 | 4.07 | 6.43 | 3.15 | 9.34 |
| PMON68537 | GM_A36362 | 74.89 | 4.14 | 6.63 | 3.11 | 10.07 |
| PMON68537 | GM_A36362 | 17.22 | 8.8 | 13.75 | 3.77 | 55.54 |
| PMON68537 | GM_A36363 | 79.15 | 3.57 | 6.2 | 3.03 | 6.84 |
| PMON68537 | GM_A36363 | 75.69 | 3.83 | 7.07 | 2.73 | 9.53 |
| PMON68537 | GM_A36363 | 73.97 | 4.22 | 6.82 | 3.39 | 10.33 |
| PMON68537 | GM_A36363 | 72.53 | 4.31 | 6.64 | 3.7 | 11.59 |
| PMON68537 | GM_A36363 | 68.42 | 4.5 | 7.05 | 3.95 | 14.79 |
| PMON68537 | GM_A36363 | 18.39 | 8.7 | 13.61 | 4.1 | 54.28 |
| PMON68537 | GM_A36363 | 17.54 | 8.87 | 14.08 | 4.07 | 54.56 |
| PMON68537 | GM_A36363 | 15.87 | 9.66 | 14.56 | 4.2 | 54.69 |
| PMON68537 | GM_A36365 | 78.79 | 3.11 | 5.87 | 1.27 | 9.9 |
| PMON68537 | GM_A36365 | 76.76 | 3.86 | 5.79 | 1.66 | 10.91 |
| PMON68537 | GM_A36365 | 75.41 | 3.49 | 6.06 | 1.83 | 12.15 |
| PMON68537 | GM_A36365 | 73.57 | 3.65 | 6.11 | 1.5 | 14.19 |
| PMON68537 | GM_A36365 | 71.55 | 3.56 | 6.62 | 1.24 | 16.08 |
| PMON68537 | GM_A36365 | 70.41 | 4 | 6.07 | 2.15 | 16.33 |
| PMON68537 | GM_A36365 | 66.66 | 3.9 | 6.84 | 1.5 | 20.21 |
| PMON68537 | GM_A36365 | 63.96 | 4.22 | 7.08 | 2.27 | 21.52 |
| PMON68537 | GM_A36366 | 75.44 | 4.33 | 6.49 | 3.21 | 9.32 |
| PMON68537 | GM_A36366 | 74.75 | 4.21 | 6.87 | 2.71 | 10.33 |
| PMON68537 | GM_A36366 | 74.69 | 4.65 | 6.91 | 3.06 | 9.65 |
| PMON68537 | GM_A36366 | 73.23 | 4.89 | 7.23 | 2.99 | 10.52 |

TABLE 3-continued

Fatty acid composition of R1 single seeds from pMON68537 Events

| Construct | Event | 18:1 | 18:3 | 16:0 | 18:0 | 18:2 |
|---|---|---|---|---|---|---|
| PMON68537 | GM_A36366 | 72.53 | 4.76 | 7.42 | 3.26 | 10.85 |
| PMON68537 | GM_A36366 | 67.15 | 5.05 | 7.47 | 3.33 | 15.87 |
| PMON68537 | GM_A36366 | 65.81 | 5.6 | 7.9 | 3.37 | 16.09 |
| PMON68537 | GM_A36366 | 62.31 | 6.19 | 8.71 | 3.22 | 18.55 |
| PMON68537 | GM_A36367 | 80.56 | 3.3 | 6.07 | 2.58 | 6.34 |
| PMON68537 | GM_A36367 | 77.78 | 3.58 | 6.47 | 2.66 | 8.45 |
| PMON68537 | GM_A36367 | 77.78 | 3.46 | 6.25 | 2.84 | 8.51 |
| PMON68537 | GM_A36367 | 77.39 | 3.81 | 6.71 | 2.86 | 8.11 |
| PMON68537 | GM_A36367 | 77.32 | 3.74 | 6.17 | 3.12 | 8.47 |
| PMON68537 | GM_A36367 | 75.93 | 3.97 | 6.23 | 3.43 | 9.29 |
| PMON68537 | GM_A36367 | 72.82 | 4.09 | 6.85 | 3.25 | 11.88 |
| PMON68537 | GM_A36367 | 19.31 | 7.58 | 13.7 | 3.59 | 55 |
| PMON68537 | GM_A36410 | 21.67 | 7.62 | 13.38 | 3.43 | 53.1 |
| PMON68537 | GM_A36410 | 20.9 | 8.33 | 12.93 | 3.64 | 53.33 |
| PMON68537 | GM_A36410 | 20.21 | 8.04 | 13.28 | 3.86 | 53.66 |
| PMON68537 | GM_A36410 | 20.02 | 8.71 | 12.79 | 3.71 | 53.87 |
| PMON68537 | GM_A36410 | 18.96 | 8.95 | 13.3 | 3.77 | 54.15 |
| PMON68537 | GM_A36410 | 18.18 | 8.98 | 13.56 | 3.74 | 54.66 |
| PMON68537 | GM_A36410 | 17.61 | 9.29 | 12.93 | 4.12 | 55.13 |
| PMON68537 | GM_A36410 | 16.78 | 9.8 | 13.78 | 3.92 | 54.83 |
| PMON68537 | GM_A36411 | 75.06 | 4.33 | 6.49 | 2.93 | 10.08 |
| PMON68537 | GM_A36411 | 74.32 | 4.46 | 6.76 | 2.96 | 10.38 |
| PMON68537 | GM_A36411 | 73.41 | 4.76 | 6.91 | 3.11 | 10.78 |
| PMON68537 | GM_A36411 | 73.24 | 4.87 | 7.28 | 2.89 | 10.67 |
| PMON68537 | GM_A36411 | 22.38 | 8.17 | 13.47 | 3.6 | 51.51 |
| PMON68537 | GM_A36411 | 18.26 | 9.07 | 14.14 | 3.81 | 54.02 |
| PMON68537 | GM_A36411 | 17.52 | 10.1 | 13.1 | 4.03 | 54.36 |
| PMON68537 | GM_A36411 | 17.02 | 9.71 | 13.45 | 4.02 | 54.89 |
| A3244 | A3244 | 18.29 | 7.79 | 13.69 | 4.15 | 55.08 |
| A3244 | A3244 | 17.54 | 8.19 | 13.32 | 4.32 | 55.57 |
| A3244 | A3244 | 17.13 | 8.13 | 13.21 | 4.46 | 56.04 |
| A3244 | A3244 | 15.47 | 9.56 | 13.04 | 4.43 | 56.46 |
| A3244 | A3244 | 15.17 | 8.95 | 13.79 | 4.3 | 56.78 |
| A3244 | A3244 | 15.05 | 9.03 | 14.16 | 4.01 | 56.8 |
| A3244 | A3244 | 13.51 | 10.07 | 12.95 | 5.07 | 57.3 |
| A3244 | A3244 | 13.49 | 9.91 | 13.31 | 4.56 | 57.67 |

Example 6 FAD2-1/FATB dsRNAi Construct in Transgenic Soybean

Construct pMON95829 as described in Example 3D is used to introduce a FAD2-1 intron, FATB, double-stranded RNA-forming construct into soybean for suppressing the FAD2 gene and FATB genes. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide. Subsequently, the genomes of transformed plants are screened for concurrent tandem insertion of the first T-DNA and the second T-DNA, i.e. in the "right border to right border" assembly. Screening is done with Southern hybridization mapping methods. Transformed soybean plants containing the preferred configuration in their genome are transferred to a green house for seed production.

For example, leaf tissue was taken from the R0 plants transformed with construct pMON95829 and Southern analysis is performed. Probes and restriction enzyme digests are chosen in order to identify events containing a right-border-right-border ("RB-RB") assembly of both T-DNAs. Typically, approximately 25% of all transformants have properly assembled RB-RB T-DNAs.

Fatty acid compositions are analyzed from seed of soybean lines transformed with a pMON95829 construct using gas chromatography as described in Example 4 to identify methyl esters of fatty acid compounds extracted from seeds. First, six R1 seeds taken from soybean plants transformed with construct pMON95829 are harvested, and the fatty acid composition of each single seed is determined. Since R1 plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 4). For example, FAD2 suppression provides plants with increased amount of oleic acid ester compounds and FATB suppression provides plants with reduced saturated fatty ester compounds, e.g. palmitates and stearates.

TABLE 4

Fatty acid composition of R1 single seeds from pMON95829 events.

| Construct | Event # | 16:0 | 18:0 | 18:1 | 18:2 | 18:3 |
|---|---|---|---|---|---|---|
| PMON95829 | GM_A94247 | 2.1 | 2.8 | 83.0 | 6.0 | 5.5 |
| PMON95829 | GM_A94296 | 2.6 | 2.9 | 80.6 | 7.1 | 5.8 |
| PMON95829 | GM_A93590 | 2.5 | 2.8 | 80.4 | 7.4 | 5.8 |
| PMON95829 | GM_A93437 | 2.6 | 2.8 | 79.8 | 7.9 | 6.0 |
| PMON95829 | GM_A93517 | 2.9 | 2.8 | 79.5 | 7.7 | 6.0 |
| PMON95829 | GM_A93647 | 2.3 | 3.0 | 78.6 | 9.0 | 6.5 |
| PMON95829 | GM_A93670 | 3.1 | 2.9 | 77.3 | 10.1 | 6.2 |
| PMON95829 | GM_A92396 | 2.9 | 2.6 | 76.0 | 11.1 | 7.0 |
| PMON95829 | GM_A92455 | 3.6 | 3.1 | 74.9 | 12.0 | 5.5 |
| PMON95829 | GM_A93678 | 2.8 | 3.4 | 74.0 | 11.9 | 7.4 |
| PMON95829 | GM_A93640 | 2.5 | 2.7 | 71.6 | 14.6 | 7.6 |
| PMON95829 | GM_A94937 | 4.5 | 3.3 | 67.2 | 17.7 | 7.1 |
| PMON95829 | GM_A92481 | 4.9 | 2.8 | 58.1 | 25.3 | 8.1 |
| PMON95829 | GM_A94306 | 3.1 | 3.2 | 55.9 | 29.0 | 7.9 |
| PMON95829 | GM_A94211 | 3.0 | 2.7 | 47.0 | 38.3 | 8.7 |

Example 7 pMON93505 is a construct used for in vivo assembly and has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 100 contiguous nucleotides from the 3' end and ligated to FATB-1a3' UTR followed by a FATB-1a5' UTR, a *C. pulcherrima* KAS IV gene (SEQ ID NO: 39) operably linking to a *Brassica* napin promoter and a *Brassica* napin 3' termination sequence, a *Ricinus communis* delta 9 desaturase gene (U.S. Patent Application Publication No. 2003/00229918 A1, now U.S. Pat. No. 7,078,588) operably linking to a soybean 7Sα' promoter and a nos 3' termination sequence, and a CP4 EPSPS gene operably linking to an eFMV promoter and a pea Rubisco E9 3' termination sequence all flanked by *Agrobacterium* T-DNA border elements, i.e. right border DNA (RB) and left border DNA (LB). On the same construct, in the second T-DNA segment, flanked by another RB and LB, is a H6 3' termination sequence operably linking to a soybean FAD2-1A intron 1 (SEQ ID NO: 1), which is reduced by 100 contiguous nucleotides from the 3' end and ligated to the FATB-1A 3' UTR followed by a FATB-1a 5' UTR.

Construct pMON93505 is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide. Subsequently, the genomes of transformed plants are screened for concurrent tandem insertion of the first T-DNA and the second T-DNA, i.e. in the "right border to right border" assembly. Screening is done with Southern hybridization mapping methods. Transformed soybean plants containing the preferred configuration in their genome are transferred to a green house for seed production.

For example, leaf tissue was taken from the R0 plants transformed with construct pMON93505 and Southern analysis is performed. Probes and restriction enzyme digests are chosen in order to identify events containing a right-border-right-border ("RB-RB") assembly of both T-DNAs. Typically, approximately 25% of all transformants have properly assembled RB-RB T-DNAs.

Fatty acid compositions are analyzed from seed of soybean lines transformed with a pMON93505 construct using gas chromatography as described in Example 4 to identify methyl esters of fatty acid compounds extracted from seeds. First, six R1 seeds taken from soybean plants transformed with construct pMON93505 are harvested, and the fatty acid composition of each single seed is determined. Since R1 plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 5). For example, FAD2 suppression provides plants with increased amount of oleic acid ester compounds. For instance, FAD2 suppression provides plants with increased amount of oleic acid ester compounds, FAD3 suppression provides plants with decreased linolenic acid ester compounds, and FATB suppression provides plants with reduced saturated fatty ester compounds, e.g. palmitates and stearates.

TABLE 5

Fatty acid composition of R1 single seeds from pMON93505 events

| Construct | Event # | 16:0 | 18:0 | 18:1 | 18:2 | 18:3 |
|---|---|---|---|---|---|---|
| PMON93505 | GM_A87814 | 1.3 | 1.0 | 84.9 | 5.5 | 6.3 |
| PMON93505 | GM_A86449 | 1.5 | 0.9 | 84.9 | 4.9 | 6.8 |
| PMON93505 | GM_A86032 | 1.5 | 1.1 | 83.5 | 6.3 | 7.0 |
| PMON93505 | GM_A86159 | 1.5 | 0.9 | 82.8 | 6.7 | 7.5 |
| PMON93505 | GM_A86178 | 1.7 | 1.0 | 82.5 | 6.7 | 7.3 |
| PMON93505 | GM_A86075 | 1.4 | 0.9 | 81.4 | 6.6 | 8.5 |
| PMON93505 | GM_A86303 | 1.0 | 0.6 | 81.4 | 7.4 | 8.8 |
| PMON93505 | GM_A86454 | 1.4 | 0.9 | 79.9 | 7.4 | 8.8 |
| PMON93505 | GM_A86799 | 1.4 | 1.1 | 79.4 | 9.6 | 7.7 |
| PMON93505 | GM_A85997 | 2.2 | 2.5 | 79.3 | 7.7 | 7.4 |
| PMON93505 | GM_A86058 | 1.8 | 1.0 | 76.8 | 11.3 | 8.3 |
| PMON93505 | GM_A86274 | 1.2 | 0.7 | 74.6 | 10.2 | 11.9 |
| PMON93505 | GM_A86325 | 1.1 | 0.7 | 72.8 | 15.4 | 9.2 |
| PMON93505 | GM_A85969 | 2.0 | 0.7 | 70.7 | 13.6 | 12.1 |
| PMON93505 | GM_A86033 | 1.7 | 0.9 | 69.1 | 18.2 | 9.5 |
| PM0N93505 | GM_A86372 | 1.7 | 1.0 | 65.7 | 12.6 | 17.6 |
| PMON93505 | GM_A86403 | 1.5 | 0.9 | 64.6 | 16.8 | 15.4 |
| PMON93505 | GM_A87803 | 1.1 | 0.6 | 57.7 | 26.0 | 13.8 |
| PMON93505 | GM_A86036 | 3.1 | 1.5 | 54.8 | 30.4 | 9.7 |
| PMON93505 | GM_A86269 | 4.9 | 1.8 | 51.4 | 31.9 | 9.5 |

Example 8 Transgenic Soybeans with Altered Fatty Acid Compositions pMON97563 contains a soybean 7Sα' promoter operably linked to a soybean FAD2-1A intron 1 (SEQ ID NO: 1), which is reduced by 100 contiguous nucleotides from the 3' end and linked to a FAD3-1A 5'UTR, followed by a FAD3-1A 3'UTR, linked to a FAD3-1B 5'UTR, followed by a FAD3-1B 3'UTR, linked to a FAD3-1C 5'UTR, followed by a FAD3-1C 3'UTR, followed by a FATB-1a CTP coding region, followed by a FATB-2a CTP coding region operably linking to 70 nucleotides from FAD3-1A intron 4, operably linking to a FATB-2a CTP coding region in the anti-sense orientation followed by a FATB-1a CTP coding region in the antisense orientation, linked to a FAD3-1C 3'UTR in antisense, followed by a FAD3-1C 5'UTR in antisense, linked to a FAD3-1B 3'UTR in antisense, followed by a FAD3-1B 5'UTR in antisense, linked to a FAD3-1A 3'UTR in antisense, followed by a FAD3-1A 5'UTR in antisense, followed by a soybean FAD2-1A intron 1 (SEQ ID NO: 1), which is reduced by 400 contiguous nucleotides from the 3' end and in the anti-sense orientation, operably linked to a H6 3' polyadenylation segment with a CP4 EPSPS gene operably linking to an eFMV promoter and a pea Rubisco E9 3' termination sequence all flanked by RB and LB on the same DNA molecule. The resulting gene expression construct is used for plant transformation using methods as described herein. Fatty acid compositions are determined from seed of soybean lines transformed with this construct using gas chromatography as described in Example 4. Table 6 gives the compositions of representative seeds. The level of 18:3 is reduced to approximately 1%.

TABLE 6

Fatty acid composition of R1 single seeds from pMON97563 events

| Construct | Event | 16:0 | 18:0 | 18:1 | 18:2 | 18:3 |
|---|---|---|---|---|---|---|
| PMON97563 | GM_A109156 | 2.21 | 2.78 | 85.05 | 8.48 | 0.69 |
| PMON97563 | GM_A109196 | 2.07 | 2.31 | 84.4 | 9.42 | 0.97 |
| PMON97563 | GM_A109207 | 2.24 | 2.78 | 83.98 | 9.36 | 0.82 |
| PMON97563 | GM_A103543 | 2.21 | 2.63 | 83.94 | 10.28 | 0.95 |
| PMON97563 | GM_A103547 | 2.06 | 2.47 | 83.67 | 10.47 | 0.89 |
| PMON97563 | GM_A109146 | 1.71 | 2.34 | 81.14 | 13.71 | 0.91 |
| PMON97563 | GM_A109155 | 2.33 | 2.7 | 80.76 | 12.28 | 1.11 |
| PMON97563 | GM_A109164 | 2.07 | 2.61 | 78.8 | 14.6 | 1 |
| PMON97563 | GM_A109170 | 2.68 | 1.95 | 78.78 | 14.14 | 1.55 |
| PMON97563 | GM_A109277 | 2.49 | 3.19 | 78.19 | 14.51 | 0.93 |
| PMON97563 | GM_A109194 | 2.46 | 2.81 | 76.62 | 16.26 | 0.92 |
| PMON97563 | GM_A109177 | 2.56 | 2.49 | 72.64 | 20.14 | 1.44 |
| PMON97563 | GM_A109201 | 2.46 | 2.9 | 72.21 | 20.13 | 1.11 |
| PMON97563 | GM_A103550 | 2.18 | 2.67 | 70.84 | 22.25 | 1.17 |
| PMON97563 | GM_A109203 | 2.18 | 2.81 | 69.93 | 22.91 | 0.98 |

Example 9 Crosses of Mid-Oleic Transgenic Soybean with Low Linolenic Soybean A soybean plant of a line with seeds having mid-oleic acid levels in its oil is crossed with a plant from a line with normal oleic acid levels but about 2.8% linolenic acid (18:3). This cross results in a soybean line producing oil with the combined properties, mid-oleic acid and low linolenic acid.

Briefly, plant breeding was performed as described below. One parent line, a transgenic soybean line, labeled event GM_A22234, contains the plasmid pMON68504 in a chromosome. pMON68504 is a 2T-DNA construct having a 7S promoter operably linked to a FAD2-1A intron #1 (SEQ ID NO: 2; PCT Publication WO 2001014538) in sense orientation in order to partially suppress the endogenous FAD2 gene and a CP4 selectable marker gene. The oil extracted from the seeds of this line contains approximately 65% oleic acid, up from the 20% of conventional soybean oil (see Table 7). Another parent line is a non-transgenic variety 6p248-5 (C1640 line) which has a linolenic acid content of about 3% by weight of total fatty acids in its seeds, as compared to the conventional 8-9% linolenic acid found in normal soybean oil (see Table 7). The reduction in linolenic acid is caused by a fad3-1b−/fad3-1c− double mutant. (See Wilcox, J. R. and J. F. Cavins, Inheritance of low linolenic acid content of the seed of a mutant of Glycine max., Theoretical and Applied Genetics 71: 74-78, 1985).

Plants of the transgenic line GM_A22234 (used as female) and the mutant line 6p248-5 (used as the male) were crossed. Thirty F1 seeds were produced and planted to produce 2.3 lbs of selfed F2 seeds. Putative triple homozygous seeds were identified from 200 F2 seeds through single seed fatty acid methyl-ester (FAME) analysis of seed chips. Twenty-seven seeds with about 60% 18:1, about 20% 18:2, and about 2-3% 18:3 were identified and planted to produce selfed F3 seeds.

For marker analysis, F2 leaf tissue samples were collected and established molecular markers for the FAD3 mutant alleles were used to identify double positive plants (plants having both FAD3-1B and FAD3-1C mutations). Three genotypes were targeted for recovery from this experiment: 1) fad3-1b−/fad3-1c− double homozygous mutants; 2) single homozygous plants for the fad3-1c− allele alone; and 3) single homozygous for fad3-1b− allele alone.

The F2 plants were single plant harvested, and 10 F3 seed sub-samples were analyzed. From 27 seeds with about 60% 18:1 (oleic acid), about 20% 18:2 (linoleic acid), and about 2-3% 18:3 (linolenic acid), 5 plants were identified as putative double-FAD3 mutant and were bulked together for further growth. Table 7 summarizes the F3 seed composition data from 120 F2 plants.

TABLE 7

Mid-oleic acid phenotype/fad3 mutant stack-F3 seed fatty acid composition

| GOI | Fatty acid, Relative mole % | | | | |
|---|---|---|---|---|---|
|  | 18:1 | 16:0 | 18:0 | 18:2 | 18:3 |
| mid-oleic(GM_A22234), fad3-1b−, Fad3-1c-(6p248-5) | 74.3 | 9.08 | 3.65 | 7.89 | 1.91 |
| fad3-1b−, Fad3-1c-Mutant Parent (6p248-5) | 30.5 | 12.3 | 3.61 | 50.90 | 2.3 |
| ~65% mid-oleic Parent (GM_A22234) | 64.6 | 9.4 | 3.61 | 14.53 | 7.27 |

The triple fad3-1b−, fad3-1c−, mid-oleic acid line (GM_AA22234) has 1.9% 18:3 linolenic and 74.3% of oleic acid. The combination of fad3-1b− and fad3-1c− mutants with the transgenic mid-oleic (GM_AA22234) locus leads to further reduction of linolenic and increase of oleic relative to the respective parent lines.

To evaluate the field efficacy of the triple fad3-1b−, fad3-1c−, mid-oleic (GM_AA22234) line, the breeding stack entries were planted in a group block design with the stacks and parental controls grouped and randomized within the testblock, and seed samples were analyzed. A fatty acid profile for the triple fad3-1b−, fad3-1c−, mid-oleic (GM_AA22234) stack was generated with F4 field grown seed using single seed FAME. F4 fatty acid profile demonstrated approximately 68% 18:1, 13% total saturates, 16% 18:2 and 2.3% 18:3. Oil and protein levels were similar to the parental lines.

Example 10 Crosses of Mid-Oleic, Low Saturate Transgenic Soybean with Low Linolenic Soybean A soybean plant of a line with seeds having mid-oleic acid and low saturates level in its oil is crossed with a plant from a line with normal oleic and saturate levels but about 2.8% linolenic acid (18:3). This cross results in a soybean line producing oil with the combined properties, mid-oleic, low saturated and low linolenic fatty acid levels.

Briefly, plant breeding was performed as described below. One parent line is a transgenic soybean line harboring recombinant DNA for partial suppression of the endogenous genes FAD2-1 and FATB as well as a CP4 selectable marker gene which renders the plant tolerant to glyphosate. The oil extracted from the seeds of this line contains approximately 55-85% oleic acid, up from the 20% of conventional soybean oil. It also contains less than 8% saturated fatty acids (16:0 plus 18:0), reduced from the conventional 14-16% of normal soybean oil. Another parent line is a non-transgenic variety 6p248-5 (C1640 line) which has about 3% linolenic acid levels in its seeds, as compared to the conventional 8-9% linolenic acid found in normal soybean oil. The reduction in linolenic acid is caused by a fad3-1b−/fad3-1c− double mutant. (See Wilcox, J. R. and J. F. Cavins, Inheritance of low linolenic acid content of the seed of a mutant of Glycine max., Theoretical and Applied Genetics 71: 74-78, 1985.)

Plants of the transgenic mid-high oleic/low saturate line are crossed with plants from the mutant line 6p248-5. F1 seeds are produced and planted to produce selfed F2 seed. Putative triple homozygous seeds are identified from F2 seeds through single seed fatty acid methyl-ester (FAME) analysis of seed chips. Seeds with combined oil traits are identified and planted to produce selfed F3 seeds. For marker analysis, F2 leaf tissue samples are collected and established molecular markers for the FAD3 mutant alleles are used to identify double positive plants (plants having both FAD3 deletions). F3 seed lots which indicate homozygosity for the transgene locus as well as the two FAD3 mutations are selected and used for line establishment.

To evaluate the field efficacy of the fad3-1b−, fad3-1c−, mid-oleic/low sat lines, the breeding stack entries are planted in a group block design with the stacks and parental controls grouped and randomized within the test block, and seed samples are analyzed. A fatty acid profile for the triple fad3-1b−, fad3-1c−, mid-oleic/low sat stack is determined with F4 field grown seed using single seed FAME. F4 fatty acid profile shows 55-85% 18:1, less than 8% saturates, and 2-3% 18:3. Oil and protein levels are similar to the parental lines.

Example 11 Use of Polymorphisms at FAD3-1b

To practice the methods of the invention, polymorphisms associated with the soybean FAD3-1B gene can be used to identify the presence of soybean genomic regions associated with certain low linolenic acid phenotypes. A single nucleotide polymorphism at a position corresponding to position 2021 of SEQ ID NO:61 is detected among all the lines in an entire sequence length of 2683 bp (Table 8) and is associated with a low-linolenic acid phenotype. Low-linolenic lines 6P248, T27111, T27190, T26767 and T26830 carry a "T" allele at this position while all other lines carry a "C". Consequently, the presence of a "T" allele can be used to identify the presence of the low linolenic soybean genomic regions in crosses where low linolenic germplasm derived from 6P248, T27111, T27190, T26767 and T26830 are used. Other low-linolenic lines such as A5, Soyola, and N98-4445 carry a wild type allele at this locus, indicating that one or more other loci contribute to the low-linolenic phenotype in the A5, Soyola, and N98-4445 lines.

TABLE 8

Polymorphisms at the FAD3-1B locus

| Lines | Position 2021 of SEQ ID NO: 61 |
|---|---|
| Orig seq | C |
| 6P248 | T |
| T27111 | T |
| T27190 | T |
| T26767 | T |
| T26830 | T |
| A5 | C |
| C1640 | C |
| Soyola | C |
| N98-4445 | C |
| A2247 | C |
| AG1701 | C |
| AG1902 | C |
| AG2402 | C |
| AG2703 | C |
| AG3201 | C |
| AG3302 | C |
| AG3702 | C |
| AJB2102J0C | C |
| AJB2302K0C | C |
| CSR2533 | C |
| CSR2622N | C |
| CSR3922N | C |
| DKB19-51 | C |
| DKB23-95 | C |
| WP25920 | C |

Example 12 Identification of Polymorphisms in the FAD3-1C Gene

To practice the methods of the invention, polymorphisms associated with the soybean FAD3-1C gene are used to identify the presence of soybean genomic regions associated with certain low linolenic acid phenotypes. Four SNPs and one indel (insertion/deletion) are identified at FAD3-1C that are associated with certain low linolenic acid phenotypes (Table 9). The SNPs corresponding to positions 687, 2316, 3743, as well as the indel at 1129 of SEQ ID NO:62 are associated with the low-linolenic phenotype. Low-linolenic lines, Soyola and N98-4445 carry a different allele at positions 687 and 1129 from all the other lines.

Mutant lines 6P248, T27111, T27190, T26767, T26830 and A5 will fail to amplify with certain FAD3-1C locus-specific primers as there is a large deletion at the FAD3-1C locus in these lines. The failure of these regions to be amplified, coupled with appropriate positive control reactions (i.e. using soybean genomic DNA that contains an intact FAD3-1C gene with FAD3-1C primers from the deleted region as well as use of primers to other non-FAD3-1C genes with the soybean genomic DNA from the FAD3-1C deletion), is diagnostic for FAD3-1C deletions.

TABLE 9

Polymorphisms at the FAD3-1C locus

| Lines | Sequence position | | | | | | |
|---|---|---|---|---|---|---|---|
| | 687 | 1129 | 1203 | 2316 | 3292 | 3360 | 3743 |
| 6P248 | NA | NA | NA | N/A | | | |
| T27111 | | NA | NA | NA | N/A | | |
| T27190 | | NA | NA | NA | N/A | | |
| T26767 | | NA | NA | NA | N/A | | |
| T26830 | | NA | NA | NA | N/A | | |
| A5 | NA | NA | NA | T | | | |
| C1640 | T | * | A | | | | |
| Soyola | | C | T | A | T | C | A | A |
| N98-4445 | | C | T | A | | | |
| A2247 | T | * | A | G | T | * | * |
| AG1701 | T | * | A | G | T | * | * |
| AG1902 | T | * | A | | T | * | * |
| AG2402 | T | * | A | G | T | * | * |
| AG2703 | T | * | A | | | | |
| AG3201 | T | * | G | | | | |
| AG3302 | T | * | A | | | | |
| AG3702 | T | * | A | | | | |
| AJB2102J0C | T | * | A | | | | |
| AJB2302K0C | | T | * | A | | | |
| CSR2533 | T | * | A | | | | |
| CSR2622N | T | * | G | | | | |
| CSR3922N | T | * | A | | | | |
| DKB19-51 | T | * | A | | | | |
| DKB23-95 | T | * | A | | | | |
| WP25920 | T | * | A | | | | |

Note:
1. NA means no amplification

Example 13 Identification of Soybean FAD3-1C Promoter Polymorphisms

To practice the methods of the invention, polymorphisms associated with the soybean FAD3-1C promoter are used to identify the presence of soybean genomic regions associated with certain low linolenic acid phenotypes. As noted in Table 10, low linolenic lines Soyola and N98-4445 carried a different allele at all seven positions from the other wild-type lines. The presence of these polymorphisms could be used to identify the presence of Soyola or N98-4445 germplasm in crosses to wild type germplasm.

TABLE 10

Polymorphisms at FAD3-1C Promoter Region

| | Position | | | | | | |
|---|---|---|---|---|---|---|---|
| | 334 | 364 | 385 | 387 | 393 | 729 | 747 |
| Soyola | G | C | T | A | C | G | C |
| N98-4445 | G | C | T | A | C | G | C |
| Wildtypes (16 lines) | A | G | G | T | T | T | T |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications and patent applications cited in this specification are herein incorporated by reference as if each individual publication or patent application was specifically and individually indicated to be incorporated by reference.

What is claimed is:

1. A seed of a soybean plant, the seed comprising:
   (i) a transgene comprising a fragment of at least 40 nucleotides of a soybean FAD2-1 exon or intron of SEQ ID NO:4, wherein said fragment is shorter than the entire sequence of the entire intron or entire exon; and
   (ii) a loss-of-function mutation in an endogenous soybean FAD3 gene of SEQ ID NO:61; and
   wherein the seed has a fatty acid composition that comprises a linolenic acid content in a range of 0.5% to 6% by weight of total seed fatty acids, a saturated fatty acid content in a range of 10% to 15% by weight of total seed fatty acids, and an oleic acid content in a range of 55% to 78% by weight of total seed fatty acids.

2. The seed of claim 1, wherein the transgene comprises a fragment of 400 to 800 nucleotides of a soybean FAD2-1 exon of SEQ ID NO:4.

3. The seed of claim 1, wherein the transgene comprises a fragment of 600 nucleotides of a soybean FAD2-1 exon of SEQ ID NO:4.

4. The seed of claim 1, wherein the loss-of-function mutation causes the delta-15 desaturase activity encoded by the endogenous soybean FAD3 gene of SEQ ID NO:61 to be reduced or absent.

5. The seed of claim 1, wherein the loss-of-function mutation comprises a frameshift or nonsense mutation in the FAD3 gene of SEQ ID NO:61.

6. The seed of claim 1, wherein the linolenic acid content is in a range of 1% to 3% by weight of total seed fatty acids, and the oleic acid content is in a range of 70% to 78% by weight of total seed fatty acids.

7. A seed of a soybean plant, the seed comprising:
   (i) a transgene comprising a fragment of at least 40 nucleotides of a soybean FAD2-1 exon or intron of SEQ ID NO:4 wherein said fragment is shorter than the entire sequence of the entire intron or entire exon; and
   (ii) a loss-of-function mutation in an endogenous soybean FAD3 gene of SEQ ID NO:62; and
   wherein the seed has a fatty acid composition that comprises a linolenic acid content in a range of 0.5% to 6% by weight of total seed fatty acids, a saturated fatty acid content in a range of 10% to 15% by weight of total seed fatty acids, and an oleic acid content in a range of 55% to 78% by weight of total seed fatty acids.

8. The seed of claim 7, wherein the transgene comprises a fragment of 400 to 800 nucleotides of a soybean FAD2-1 exon of SEQ ID NO:4.

9. The seed of claim 7, wherein the transgene comprises a fragment of 600 nucleotides of a soybean FAD2-1 exon of SEQ ID NO:4.

10. The seed of claim 7, wherein the loss-of-function mutation causes the delta-15 desaturase activity encoded by the endogenous soybean FAD3 gene of SEQ ID NO:62 to be reduced or absent.

11. The seed of claim 7, wherein the loss-of-function mutation comprises a frameshift or nonsense mutation in the FAD3 gene of SEQ ID NO:62.

12. The seed of claim 7, wherein the loss-of-function mutation comprises a deletion in the FAD3 gene of SEQ ID NO:62.

13. The seed of claim 7, wherein the linolenic acid content is in a range of 1% to 3% by weight of total seed fatty acids, and the oleic acid content is in a range of 70% to 78% by weight of total seed fatty acids.

* * * * *

```
                        SEQUENCE LISTING

<160> NUMBER OF SEQ ID NOS: 65

<210> SEQ ID NO 1
<211> LENGTH: 420
<212> TYPE: DNA
<213> ORGANISM: Glycine max
<220> FEATURE:
<221> NAME/KEY: Intron
<222> LOCATION: (1)..(420)
<223> OTHER INFORMATION: FAD2-1A intron 1

<400> SEQUENCE: 1
gtaaattaaa ttgtgcctgc acctcgggat atttcatgtg gggttcatca tatttgttga      60
ggaaaagaaa ctcccgaaat tgaattatgc atttatatat ccttttcat ttctagattt      120 cctgaaggct taggtgtagg cacctagcta gtagctacaa tatcagcact tctctctatt     180
gataaacaat tggctgtaat gccgcagtag aggacgatca caacatttcg tgctggttac     240
tttttgtttt atggtcatga tttcactctc tctaatctct ccattcattt tgtagttgtc     300
attatcttta gatttttcac tacctggttt aaaattgagg gattgtagtt ctgttggtac     360
atattacaca ttcagcaaaa caactgaaac tcaactgaac ttgtttatac tttgacacag     420

<210> SEQ ID NO 2
<211> LENGTH: 405
<212> TYPE: DNA
<213> ORGANISM: Glycine max
<220> FEATURE:
<221> NAME/KEY: Intron
<222> LOCATION: (1)..(405)
<223> OTHER INFORMATION: FAD2-1B intron 1

<400> SEQUENCE: 2
gtatgatgct aaattaaatt gtgcctgcac cccaggatat ttcatgtggg attcatcatt      60
tattgaggaa aactctccaa attgaatcgt gcatttatat tttttttcca tttctagatt     120
tcttgaaggc ttatggtata ggcacctaca attatcagca cttctctcta ttgataaaca     180
attggctgta ataccacagt agagaacgat cacaacattt tgtgctggtt acctttttgtt    240 ttatggtcat gatttcactc tctctaatct gtcacttccc tccattcatt ttgtacttct     300
catatttttc acttcctggt tgaaaattgt agttctcttg gtacatacta gtattagaca     360
ttcagcaaca acaactgaac tgaacttctt tatactttga cacag                     405

<210> SEQ ID NO 3
```

<211> LENGTH: 1704
<212> TYPE: DNA
<213> ORGANISM: Glycine max
<220> FEATURE:
<221> NAME/KEY: promoter
<222> LOCATION: (1)..(1704)
<223> OTHER INFORMATION: FAD2-1B promoter

<400> SEQUENCE: 3

```
actatagggc acgcgtggtc gacggcccgg gctggtcctc ggtgtgactc agcccaagt    60
gacgccaacc aaacgcgtcc taactaaggt gtagaagaaa cagatagtat ataagtatac   120
catataagag gagagtgagt ggagaagcac ttctcctttt tttttctctg ttgaaattga   180
aagtgttttc cgggaaataa ataaaataaa ttaaaatctt acacactcta ggtaggtact   240
tctaatttaa tccacacttt gactctatat atgttttaaa ataattata atgcgtactt    300
acttcctcat tatactaaat ttaacatcga tgattttatt ttctgtttct cttctttcca   360
cctacataca tcccaaaatt tagggtgcaa ttttaagttt attaacacat gttttagct    420
gcatgctgcc tttgtgtgtg ctcaccaaat tgcattcttc tctttatatg ttgtatttga   480
attttcacac catatgtaaa caagattacg tacgtgtcca tgatcaaata caaatgctgt   540
cttatactgg caatttgata aacagccgtc cattttttct ttttctcttt aactatatat   600
gctctagaat ctctgaagat tcctctgcca tcgaatttct ttcttggtaa caacgtcgtc   660
gttatgttat tattttattc tatttttatt ttatcatata tatttcttat tttgttcgaa   720
gtatgtcata ttttgatcgt gacaattaga ttgtcatgta ggagtaggaa tatcacttta   780
aaacattgat tagtctgtag gcaatattgt cttcttttc ctcctttatt aatatatttt    840
gtcgaagttt taccacaagg ttgattcgct tttttgtcc ctttctcttg ttcttttac     900
ctcaggtatt ttagtctttc atggattata agatcactga gaagtgtatg catgtaatac   960
taagcaccat agctgttctg cttgaattta tttgtgtgta aattgtaatg tttcagcgtt  1020
ggctttccct gtagctgcta caatggtact gtatatctat tttttgcatt gttttcattt  1080
tttcttttac ttaatcttca ttgctttgaa attaataaaa caatataata tagtttgaac  1140
tttgaactat tgcctattca tgtaattaac ttattcactg actcttattg ttttttctggt 1200
agaattcatt ttaaattgaa ggataaatta agaggcaata cttgtaaatt gacctgtcat  1260
aattacacag gaccctgttt tgtgccttt tgtctctgtc tttggttttg catgttagcc    1320
tcacacagat atttagtagt tgttctgcat acaagcctca cacgtatact aaaccagtgg  1380
acctcaaagt catggcctta cacctattgc atgcgagtct gtgacacaac ccctggtttc  1440
catattgcaa tgtgctacgc cgtcgtcctt gtttgtttcc atatgtatat tgataccatc  1500
aaattattat atcatttata tggtctggac cattacgtgt actctttatg acatgtaatt  1560
gagttttta attaaaaaaa tcaatgaaat ttaactacgt agcatcatat agagataatt   1620
gactagaaat ttgatgactt attctttcct aatcatattt tcttgtattg atagccccgc  1680
tgtccctttt aaactcccga gaga                                          1704
```

<210> SEQ ID NO 4
<211> LENGTH: 4497
<212> TYPE: DNA
<213> ORGANISM: Glycine max
<220> FEATURE:
<221> NAME/KEY: gene
<222> LOCATION: (1)..(4497)
<223> OTHER INFORMATION: FAD2-1A genomic clone

<400> SEQUENCE: 4

```
cttgcttggt aacaacgtcg tcaagttatt attttgttct ttttttttt atcatatttc      60
ttattttgtt ccaagtatgt catattttga tccatcttga caagtagatt gtcatgtagg    120
aataggaata tcactttaaa ttttaaagca ttgattagtc tgtaggcaat attgtcttct    180
tcttcctcct tattaatatt ttttattctg ccttcaatca ccagttatgg gagatggatg    240
taatactaaa taccatagtt gttctgcttg aagtttagtt gtatagttgt tctgcttgaa    300
gtttagttgt gtgtaatgtt tcagcgttgg cttcccctgt aactgctaca atggtactga    360
atatatattt tttgcattgt tcattttttt cttttactta atcttcattg ctttgaaatt    420
aataaaacaa aaagaaggac cgaatagttt gaagttgaa ctattgccta ttcatgtaac     480
ttattcaccc aatcttatat agtttttctg gtagagatca ttttaaattg aaggatataa    540
attaagagga aatacttgta tgtgatgtgt ggcaatttgg aagatcatgc gtagagagtt    600
taatggcagg ttttgcaaat tgacctgtag tcataattac actgggccct ctcggagttt    660
tgtgcctttt tgttgtcgct gtgtttggtt ctgcatgtta gcctcacaca gatatttagt    720
agttgttgtt ctgcatataa gcctcacacg tatactaaac gagtgaacct caaaatcatg    780
gccttacacc tattgagtga aattaatgaa cagtgcatgt gagtatgtga ctgtgacaca    840
acccccggtt ttcatattgc aatgtgctac tgtggtgatt aaccttgcta cactgtcgtc    900
cttgtttgtt tccttatgta tattgatacc ataaattatt actagtatat cattttatat    960
tgtccatacc attacgtgtt tatagtctct ttatgacatg taattgaatt ttttaattat   1020
aaaaaataat aaaacttaat tacgtactat aaagagatgc tcttgactag aattgtgatc   1080
tcctagtttc ctaaccatat actaatattt gcttgtattg atagcccctc cgttcccaag   1140
agtataaaac tgcatcgaat aatacaagcc actaggcatg gtaaattaaa ttgtgcctgc   1200
acctcgggat atttcatgtg gggttcatca tatttgttga ggaaagaaa ctcccgaaat    1260
tgaattatgc atttatatat ccttttttcat ttctagattt cctgaaggct taggtgtagg   1320
cacctagcta gtagctacaa tatcagcact tctctctatt gataaacaat tggctgtaat   1380
gccgcagtag aggacgatca caacatttcg tgctggttac ttttgtttt atggtcatga    1440
tttcactctc tctaatctct ccattcattt tgtagttgtc attatcttta gatttttcac   1500
tacctggttt aaaattgagg gattgtagtt ctgttggtac atattacaca ttcagcaaaa   1560
caactgaaac tcaactgaac ttgtttatac tttgacacag gtctagcaa aggaaacaac    1620
aatgggaggt agaggtcgtg tggcaaagtg gaagttcaag ggaagaagcc tctctcaagg   1680
gttccaaaca caaagccacc attcactgtt ggccaactca agaaagcaat tccaccacac   1740
tgctttcagc gctccctcct cacttcattc tcctatgttg tttatgacct tcatttgcc    1800
ttcattttct acattgccac cacctacttc cacctccttc ctcaacccctt tccctcatt    1860
gcatggccaa tctattgggt tctccaaggt tgccttctca ctggtgtgtg ggtgattgct   1920
cacgagtgtg gtcaccatgc cttcagcaag taccaatggg ttgatgatgt tgtgggtttg   1980
acccttcact caacactttt agtcccttat ttctcatgga aaataagcca tcgccgccat   2040
cactccaaca caggttccct tgaccgtgat gaagtgtttg tcccaaaacc aaaatccaaa   2100
gttgcatggt tttccaagta cttaaacaac cctctaggaa gggctgtttc tcttctcgtc   2160
acactcacaa tagggtggcc tatgtattta gccttcaatg tctctggtag accctatgat   2220
agttttgcaa gccactacca cccctatgct cccatatatt ctaaccgtga gaggcttctg   2280
atctatgtct ctgatgttgc tttgttttct gtgacttact ctctctaccg tgttgcaacc   2340
```

```
ctgaaagggt tggtttggct gctatgtgtt tatggggtgc ctttgctcat tgtgaacggt    2400
tttcttgtga ctatcacata tttgcagcac acacactttg ccttgcctca ttacgattca    2460
tcagaatggg actggctgaa gggagctttg caactatgg acagagatta tgggattctg     2520
aacaaggtgt ttcatcacat aactgatact catgtggctc accatctctt ctctacaatg    2580
ccacattacc atgcaatgga ggcaaccaat gcaatcaagc caatattggg tgagtactac    2640
caatttgatg acacaccatt ttacaaggca ctgtggagag aagcgagaga gtgcctctat    2700
gtggagccag atgaaggaac atccgagaag ggcgtgtatt ggtacaggaa caagtattga    2760
tggagcaacc aatgggccat agtgggagtt atggaagttt tgtcatgtat tagtacataa    2820
ttagtagaat gttataaata agtggatttg ccgcgtaatg actttgtgtg tattgtgaaa    2880
cagcttgttg cgatcatggt tataatgtaa aaataattct ggtattaatt acatgtggaa    2940
agtgttctgc ttatagcttt ctgcctaaaa tgcacgctgc acgggacaat atcattggta    3000 attttttaa aatctgaatt gaggctactc ataatactat ccataggaca tcaaagacat     3060
gttgcattga ctttaagcag aggttcatct agaggattac tgcataggct tgaactacaa    3120
gtaatttaag ggacgagagc aactttagct ctaccacgtc gttttacaag gttattaaaa    3180
tcaaattgat cttattaaaa ctgaaaattt gtaataaaat gctattgaaa aattaaaata    3240
tagcaaacac ctaaattgga ctgatttttta gattcaaatt taataattaa tctaaattaa   3300
acttaaattt tataatatat gtcttgtaat atatcaagtt ttttttttta ttattgagtt    3360
tggaaacata taataaggaa cattagttaa tattgataat ccactaagat cgacttagta    3420
ttacagtatt tggatgattt gtatgagata ttcaaacttc actcttatca taatagagac    3480
aaaagttaat actgatggtg gagaaaaaaa aatgttattg ggagcatatg gtaagataag    3540
acggataaaa atatgctgca gcctggagag ctaatgtatt ttttggtgaa gttttcaagt    3600
gacaactatt catgatgaga acacaataat attttctact tacctatccc acataaaata    3660
ctgattttaa taatgatgat aaataatgat taaaatattt gattctttgt taagagaaat    3720
aaggaaaaca taaatattct catggaaaaa tcagcttgta ggagtagaaa ctttctgatt    3780
ataattttaa tcaagtttaa ttcattcttt taattttatt attagtacaa aatcattctc    3840
ttgaatttag agatgtatgt tgtagcttaa tagtaatttt ttattttat aataaaattc     3900 aagcagtcaa atttcatcca aataatcgtg ttcgtgggtg taagtcagtt attccttctt    3960
atcttaatat acacgcaaag gaaaaaataa aaataaaatt cgaggaagcg cagcagcagc    4020
tgataccacg ttggttgacg aaactgataa aaagcgctgt cattgtgtct ttgtttgatc    4080
atcttcacaa tcacatctcc agaacacaaa gaagagtgac ccttcttctt gttattccac    4140
ttgcgttagg tttctacttt cttctctctc tctctctctc tcttcattcc tcattttcc     4200 ctcaaacaat caatcaattt tcattcagat tcgtaaattt ctcgattaga tcacggggtt    4260
aggtctccca ctttatcttt tcccaagcct ttctctttcc ccctttccct gtctgcccca    4320
taaaattcag gatcggaaac gaactgggtt cttgaatttc actctagatt ttgacaaatt    4380
cgaagtgtgc atgcactgat gcgacccact cccccttttt tgcattaaac aattatgaat    4440
tgaggttttt cttgcgatca tcattgcttg aattgaatca tattaggttt agattct       4497
```

<210> SEQ ID NO 5
<211> LENGTH: 206
<212> TYPE: DNA
<213> ORGANISM: Glycine max
<220> FEATURE:
<221> NAME/KEY: 3'UTR

```
<222> LOCATION: (1)..(206)
<223> OTHER INFORMATION: FAD2-1A 3' UTR

<400> SEQUENCE: 5
tggagcaacc aatgggccat agtgggagtt atggaagttt tgtcatgtat agtacataa      60 ttagtagaat gttataaata agtggatttg ccgcgtaatg actttgtgtg tattgtgaaa    120
cagcttgttg cgatcatggt tataatgtaa aaataattct ggtattaatt acatgtggaa    180
agtgttctgc ttatagcttt ctgcct                                         206

<210> SEQ ID NO 6
<211> LENGTH: 125
<212> TYPE: DNA
<213> ORGANISM: Glycine max
<220> FEATURE:
<221> NAME/KEY: 5'UTR
<222> LOCATION: (1)..(125)
<223> OTHER INFORMATION: FAD2-1A 5' UTR

<400> SEQUENCE: 6
ccatatacta atatttgctt gtattgatag cccctccgtt cccaagagta taaaactgca     60
tcgaataata caagccacta ggcatgggtc tagcaaagga acaacaatg ggaggtagag     120 gtcgt                                                                125

<210> SEQ ID NO 7
<211> LENGTH: 191
<212> TYPE: DNA
<213> ORGANISM: Glycine max
<220> FEATURE:
<221> NAME/KEY: Intron
<222> LOCATION: (1)..(191)
<223> OTHER INFORMATION: FAD3-1A intron 1

<400> SEQUENCE: 7
gtaataattt ttgtgtttct tactcttttt tttttttttt tgtttatgat atgaatctca     60
cacattgttc tgttatgtca tttcttcttc atttggcttt agacaactta aatttgagat    120
ctttattatg tttttgctta tatggtaaag tgattcttca ttatttcatt cttcattgat    180
tgaattgaac a                                                         191

<210> SEQ ID NO 8
<211> LENGTH: 346
<212> TYPE: DNA
<213> ORGANISM: Glycine max
<220> FEATURE:
<221> NAME/KEY: Intron
<222> LOCATION: (1)..(346)
<223> OTHER INFORMATION: FAD3-1A intron 2

<400> SEQUENCE: 8
ttagttcata ctggcttttt tgtttgttca tttgtcattg aaaaaaaatc ttttgttgat     60
tcaattattt ttatagtgtg tttggaagcc gtttgagaa aataagaaat cgcatctgga    120
atgtgaaagt tataactatt tagcttcatc tgtcgttgca agttctttta ttggttaaat    180
ttttatagcg tgctaggaaa cccattcgag aaaataagaa atcacatctg gaatgtgaaa    240
gttataactg ttagcttctg agtaaacgtg gaaaaaccac attttggatt tggaaccaaa    300 tttttatttga taaatgacaa ccaaattgat tttgatggat tttgca                  346

<210> SEQ ID NO 9
<211> LENGTH: 142
<212> TYPE: DNA
```

<213> ORGANISM: Glycine max
<220> FEATURE:
<221> NAME/KEY: Intron
<222> LOCATION: (1)..(142)
<223> OTHER INFORMATION: FAD3-1A intron 3A

<400> SEQUENCE: 9

```
gtatgtgatt aattgcttct cctatagttg ttcttgattc aattacattt tatttatttg    60
gtaggtccaa gaaaaaaggg aatctttatg cttcctgagg ctgttcttga acatggctct   120
ttttatgtg tcattatctt ag                                             142
```

<210> SEQ ID NO 10
<211> LENGTH: 1228
<212> TYPE: DNA
<213> ORGANISM: Glycine max
<220> FEATURE:
<221> NAME/KEY: Intron
<222> LOCATION: (1)..(1228)
<223> OTHER INFORMATION: FAD3-1A intron 4

<400> SEQUENCE: 10

```
taacaaaaat aaatagaaaa tagtgggtga acacttaaat gcgagatagt aatacctaaa     60
aaagaaaaa aatataggta taataaataa tataactttc aaaataaaaa gaaatcatag    120
agtctagcgt agtgtttgga gtgaaatgat gttcacctac cattactcaa agattttgtt   180
gtgtccctta gttcattctt attatttac atatcttact tgaaaagact ttttaattat    240
tcattgagat cttaaagtga ctgttaaatt aaaataaaaa acaagtttgt taaaacttca   300
aataaataag agtgaaggga gtgtcatttg tcttctttct tttattgcgt tattaatcac   360
gtttctcttc tcttttttt ttttcttctc tgctttccac ccattatcaa gttcatgtga    420
agcagtggcg gatctatgta aatgagtggg gggcaattgc acccacaaga ttttattttt   480
tatttgtaca ggaataataa aataaaactt tgcccccata aaaataaat attttttctt    540
aaaataatgc aaaataaata taagaaataa aaagagaata aattattatt aattttatta   600
ttttgtactt tttatttagt tttttttagcg gttagatttt ttttcatga cattatgtaa    660
tcttttaaaa gcatgtaata tttttatttt gtgaaaataa atataaatga tcatattagt   720
ctcagaatgt ataaactaat aataatttta tcactaaaag aaattctaat ttagtccata   780
aataagtaaa acaagtgaca attatatttt atatttactt aatgtgaaat aatacttgaa   840
cattataata aaacttaatg acaggagata ttacatagtg ccataaagat attttaaaaa   900
ataaaatcat taatacactg tactactata taatattcga tatatatttt taacatgatt   960
ctcaatagaa aaattgtatt gattatattt tattagacat gaatttacaa gccccgtttt  1020
tcatttatag ctcttacctg tgatctattg ttttgcttcg ctgttttgt tggtcaaggg   1080
acttagatgt cacaatatta atactagaag taaatattta tgaaacatg taccttacct   1140
caacaaagaa agtgtggtaa gtggcaacac acgtgttgca ttttggccc agcaataaca  1200
cgtgtttttg tggtgtacta aaatggac                                     1228
```

<210> SEQ ID NO 11
<211> LENGTH: 625
<212> TYPE: DNA
<213> ORGANISM: Glycine max
<220> FEATURE:
<221> NAME/KEY: Intron
<222> LOCATION: (1)..(625)
<223> OTHER INFORMATION: FAD3-1A intron 5

<400> SEQUENCE: 11

```
gtacatttta ttgcttattc acctaaaaac aatacaatta gtacatttgt tttatctctt      60
ggaagttagt cattttcagt tgcatgattc taatgctctc tccattctta aatcatgttt     120
tcacacccac ttcatttaaa ataagaacgt gggtgttatt ttaatttcta ttcactaaca     180
tgagaaatta acttatttca agtaataatt ttaaaatatt tttatgctat tattttatta     240
caaataatta tgtatattaa gtttattgat tttataataa ttatattaaa attatatcga     300 tattaattttt tgattcactg atagtgtttt atattgttag tactgtgcat ttattttaaa    360
attggcataa ataatatatg taaccagctc actatactat actgggagct tggtggtgaa     420
aggggttccc aaccctcctt tctaggtgta catgctttga tacttctggt accttcttat     480
atcaatataa attatatttt gctgataaaa aaacatggtt aaccattaaa ttcttttttt     540
aaaaaaaaaa ctgtatctaa actttgtatt attaaaaaga agtctgagat taacaataaa     600
ctaacactca tttggattca ctgca                                           625

<210> SEQ ID NO 12
<211> LENGTH: 98
<212> TYPE: DNA
<213> ORGANISM: Glycine max
<220> FEATURE:
<221> NAME/KEY: Intron
<222> LOCATION: (1)..(98)
<223> OTHER INFORMATION: FAD3-1A intron 3B

<400> SEQUENCE: 12
ggtgagtgat tttttgactt ggaagacaac aacacattat tattataata tggttcaaaa     60
caatgacttt ttctttatga tgtgaactcc atttttta                             98

<210> SEQ ID NO 13
<211> LENGTH: 115
<212> TYPE: DNA
<213> ORGANISM: Glycine max
<220> FEATURE:
<221> NAME/KEY: Intron
<222> LOCATION: (1)..(115)
<223> OTHER INFORMATION: FAD3-1A intron 3C

<400> SEQUENCE: 13
ggtaactaaa ttactcctac attgttactt tttcctcctt ttttttatta tttcaattct     60
ccaattggaa atttgaaata gttaccataa ttatgtaatt gtttgatcat gtgca          115

<210> SEQ ID NO 14
<211> LENGTH: 1037
<212> TYPE: DNA
<213> ORGANISM: Glycine max
<220> FEATURE:
<221> NAME/KEY: Intron
<222> LOCATION: (1)..(1037)
<223> OTHER INFORMATION: FAD3-1C intron 4

<400> SEQUENCE: 14
gtaacaaaaa taaatagaaa atagtgagtg aacacttaaa tgttagatac taccttcttc     60
ttcttttttt tttttttttt gaggttaatg ctagataata gctagaaaga gaaagaaaga    120
caaatatagg taaaaataaa taatataacc tgggaagaag aaaacataaa aaagaaaata    180
atagagtcta cgtaatgttt ggattttttga gtgaaatggt gttcacctac cattactcaa   240
agattctgtt gtctacgtag tgtttggact tggagtgaa atggtgttca cctaccatta     300
ctcagattct gttgtgtccc ttagttactg tcttatattc ttagggtata ttctttattt    360
```

| | | |
|---|---|---|
| tacatcctttt tcacatctta cttgaaaaga ttttaattat tcattgaaat attaacgtga | 420 | |
| cagttaaatt aaaataataa aaaattcgtt aaaacttcaa ataaataaga gtgaaaggat | 480 | |
| catcatttttt cttctttctt ttattgcgtt attaatcatg cttctcttct ttttttttctt | 540 | |
| cgcttttccac ccatatcaaa ttcatgtgaa gtatgagaaa atcacgattc aatggaaagc | 600 | |
| tacaggaacy ttttttgttt tgttttttata atcggaatta atttatactc catttttttca | 660 | |
| caataaatgt tacttagtgc cttaaagata atatttgaaa aattaaaaaa attattaata | 720 | |
| cactgtacta ctatataata tttgacatat atttaacatg attttctatt gaaaatttgt | 780 | |
| atttattatt ttttaatcaa aacccataag gcattaattt acaagaccca tttttcattt | 840 | |
| atagctttac ctgtgatcat ttatagcttt aagggactta gatgttacaa tcttaattac | 900 | |
| aagtaaatat ttatgaaaaa catgtgtctt accccttaac cttacctcaa caaagaaagt | 960 | |
| gtgataagtg gcaacacacg tgttgctttt ttggcccagc aataacacgt gttttttgtgg | 1020 | |
| tgtacaaaaa tggacag | 1037 | |

<210> SEQ ID NO 15
<211> LENGTH: 4010
<212> TYPE: DNA
<213> ORGANISM: Glycine max
<220> FEATURE:
<221> NAME/KEY: gene
<222> LOCATION: (1)..(4010)
<223> OTHER INFORMATION: partial FAD3-1A genomic clone

<400> SEQUENCE: 15

| | | |
|---|---|---|
| acaaagcctt tagcctatgc tgccaataat ggataccaac aaaagggttc ttcttttgat | 60 | |
| tttgatccta gcgctcctcc accgtttaag attgcagaaa tcagagcttc aataccaaaa | 120 | |
| cattgctggg tcaagaatcc atggagatcc ctcagttatg ttctcaggga tgtgcttgta | 180 | |
| attgctgcat tggtggctgc agcaattcac ttcgacaact ggcttctctg gctaatctat | 240 | |
| tgccccattc aaggcacaat gttctgggct ctcttttgttc ttggacatga ttggtaataa | 300 | |
| ttttttgtgtt tcttactctt tttttttttttt ttttgtttat gatatgaatc tcacacattg | 360 | |
| ttctgttatg tcatttcttc ttcatttggc tttagacaac ttaaatttga gatctttatt | 420 | |
| atgttttttgc ttatatggta aagtgattct tcattatttc attcttcatt gattgaattg | 480 | |
| aacagtggcc atgaagcttt tcagatagc cctttgctga atagcctggt gggacacatc | 540 | |
| ttgcattcct caattcttgt gccataccat ggatggtag ttcatactgg cttttttgtt | 600 | |
| tgttcatttg tcattgaaaa aaaatctttt gttgattcaa ttatttttat agtgtgtttg | 660 | |
| gaagcccgtt tgagaaaata agaaatcgca tctggaatgt gaaagttata actatttagc | 720 | |
| ttcatctgtc gttgcaagtt cttttattgg ttaaatttttt atagcgtgct aggaaaccca | 780 | |
| ttcgagaaaa taagaaatca catctggaat gtgaaagtta taactgttag cttctgagta | 840 | |
| aacgtggaaa aaccacattt tggatttgga accaaatttt atttgataaa tgacaaccaa | 900 | |
| attgatttttg atggattttg caggagaatt agccacagaa ctcaccatga aaccatgga | 960 | |
| cacattgaga aggatgagtc atgggttcca gtatgtgatt aattgcttct cctatagttg | 1020 | |
| ttcttgattc aattacattt tattttatttg gtaggtccaa gaaaaagggg aatctttatg | 1080 | |
| cttcctgagg ctgttcttga acatggctct ttttttatgtg tcattatctt agttaacaga | 1140 | |
| gaagatttac aagaatctag acagcatgac aagactcatt agattcactg tgccatttcc | 1200 | |
| atgtttgtgt atccaattta tttggtgagt gattttttga cttggaagac aacaacacat | 1260 | |
| tattattata atatggttca aaacaatgac ttttttcttta tgatgtgaac tccatttttt | 1320 | |

```
agttttcaag aagccccgga aaggaaggct ctcacttcaa tccctacagc aatctgtttc    1380
cacccagtga gagaaaagga atagcaatat caacactgtg ttgggctacc atgttttctc    1440
tgcttatcta tctctcattc attaactagt ccacttctag tgctcaagct ctatggaatt    1500
ccatattggg taactaaatt actcctacat tgttactttt tcctccttt ttttattatt    1560 tcaattctcc aattggaaat ttgaaatagt taccataatt atgtaattgt ttgatcatgt    1620
gcagatgttt gttatgtggc tggactttgt cacatacttg catcaccatg gtcaccacca    1680
gaaactgcct tggtaccgcg gcaaggtaac aaaaataaat agaaatagt gggtgaacac     1740 ttaaatgcga gatagtaata cctaaaaaaa gaaaaaaata taggtataat aaataatata    1800
actttcaaaa taaaagaaa tcatagagtc tagcgtagtg tttggagtga atgatgttc      1860 acctaccatt actcaaagat tttgttgtgt cccttagttc attcttatta ttttacatat    1920
cttacttgaa aagactttt aattattcat tgagatctta aagtgactgt taaattaaaa    1980
taaaaaacaa gttgttaaa acttcaaata aataagagtg aagggagtgt catttgtctt    2040
ctttctttta ttgcgttatt aatcacgttt ctcttctctt ttttttttt cttctctgct    2100 ttccacccat tatcaagttc atgtgaagca gtggcggatc tatgtaaatg agtgggggc    2160 aattgcaccc acaagatttt atttttatt tgtacaggaa taataaata aactttgcc    2220 cccataaaaa ataaatattt tttcttaaaa taatgcaaaa taaatataag aaataaaaag    2280
agaataaatt attattaatt ttattatttt gtactttta tttagtttt ttagcggtta    2340 gatttttttt tcatgacatt atgtaatctt ttaaaagcat gtaatatttt tattttgtga    2400
aaataaatat aaatgatcat attagtctca gaatgtataa actaataata attttatcac    2460
taaaagaaat tctaatttag tccataaata agtaaaacaa gtgacaatta tatttatat    2520 ttacttaatg tgaaataata cttgaacatt ataataaaac ttaatgacag gagatattac    2580
atagtgccat aaagatattt taaaaataa aatcattaat acactgtact actatataat    2640
attcgatata tattttaac atgattctca atagaaaaat tgtattgatt atattttatt    2700
agacatgaat ttacaagccc cgttttcat ttatagctct tacctgtgat ctattgtttt    2760
gcttcgctgt ttttgttggt caagggactt agatgtcaca atattaatac tagaagtaaa    2820
tatttatgaa aacatgtacc ttacctcaac aaagaaagtg tggtaagtgg caacacacgt    2880
gttgcatttt tggcccagca ataacacgtg tttttgtggt gtactaaaat ggacaggaat    2940
ggagttattt aagaggtggc ctcaccactg tggatcgtga ctatggttgg atcaataaca    3000
ttcaccatga cattggcacc catgttatcc accatcttt ccccaaatt cctcattatc     3060 acctcgttga agcggtacat tttattgctt attcacctaa aaacaataca attagtacat    3120
ttgttttatc tcttggaagt tagtcatttt cagttgcatg attctaatgc tctctccatt    3180
cttaaatcat gttttcacac ccacttcatt taaaataaga acgtgggtgt tattttaatt    3240
tctattcact aacatgagaa attaacttat ttcaagtaat aatttaaaa tattttatg     3300 ctattatttt attacaaata attatgtata ttaagtttat tgattttata ataattatat    3360
taaaattata tcgatattaa tttttgattc actgatagtg ttttatattg ttagtactgt    3420
gcatttattt taaaattggc ataaataata tatgtaacca gctcactata ctatactggg    3480
agcttggtgg tgaaaggggt tcccaaccct cctttctagg tgtacatgct tgatacttc    3540 tggtaccttc ttatatcaat ataaattata ttttgctgat aaaaaaacat ggttaaccat    3600
taaattcttt ttttaaaaaa aaaactgtat ctaaactttg tattattaaa aagaagtctg    3660
```

-continued

```
agattaacaa taaactaaca ctcatttgga ttcactgcag acacaagcag caaaaccagt    3720
tcttggagat tactaccgtg agccagaaag atctgcgcca ttaccatttc atctaataaa    3780
gtatttaatt cagagtatga gacaagacca cttcgtaagt gacactggag atgttgttta    3840
ttatcagact gattctctgc tcctccactc gcaacgagac tgagtttcaa acttttgggg   3900
ttattattta ttgattctag ctactcaaat tactttttt ttaatgttat gttttttgga    3960
gtttaacgtt ttctgaacaa cttgcaaatt acttgcatag agagacatgg               4010
```

<210> SEQ ID NO 16
<211> LENGTH: 184
<212> TYPE: DNA
<213> ORGANISM: Glycine max
<220> FEATURE:
<221> NAME/KEY: 3'UTR
<222> LOCATION: (1)..(184)
<223> OTHER INFORMATION: FAD3-1A 3' UTR

<400> SEQUENCE: 16

```
gtttcaaact ttttgggtta ttatttattg gattctagct actcaaatta cttttttttt     60
aatgttatgt tttttggagt ttaacgtttt ctgaacaact tgcaaattac ttgcatagag    120
agacatggaa tatttatttg aaattagtaa ggtagtaata ataaattttg aattgtcagt    180
ttca                                                                 184
```

<210> SEQ ID NO 17
<211> LENGTH: 143
<212> TYPE: DNA
<213> ORGANISM: Glycine max
<220> FEATURE:
<221> NAME/KEY: 5'UTR
<222> LOCATION: (1)..(143)
<223> OTHER INFORMATION: FAD3-1A 5' UTR

<400> SEQUENCE: 17

```
tgcggttata taaatgcact atcccataag agtattttc gaagatttcc ttcttcctat      60
tctaggtttt tacgcaccac gtatccctga gaaaagagag gaaccacact ctctaagcca   120
aagcaaaagc agcagcagca gca                                            143
```

<210> SEQ ID NO 18
<211> LENGTH: 2683
<212> TYPE: DNA
<213> ORGANISM: Glycine max
<220> FEATURE:
<221> NAME/KEY: gene
<222> LOCATION: (1)..(2683)
<223> OTHER INFORMATION: partial FAD3-1B genomic clone

<400> SEQUENCE: 18

```
gttcaagcac agcctctaca acatgttggt aatggtgcag ggaaagaaga tcaagcttat      60
tttgatccaa gtgctccacc acccttcaag attgcaaata tcagagcagc aattccaaaa    120
cattgctggg agaagaacac attgagatct ctgagttatg ttctgaggga tgtgttggta    180
gtgactgcat tggtagctgc agcaatcggc ttcaatagct ggttcttctg ccactctat     240 tggcctgcac aaggcacaat gttttgggca cttttttgttc ttggacatga ttggtaacta   300
attattatta caaattgtta tgttatgtta tgttatgttg ttgtgccttt ttctcagtga    360
tgctttagtc atttcatttc acttggttat gcatgattgt tcgttcatat gttctgtcat    420
ggtgagttct aatttgattg atgcatggaa cagtggtcat ggaagttttt caaacagtcc    480
tttgttgaac agcattgtgg gccacatctt gcactcttca attcttgtac cataccatgg    540
```

```
atggtcggtt cctttagca acttttcatg ttcactttgt ccttaaattt tttttatgt      600
ttgttaaaaa atctttggtc tgatttaaca acctaaccat ttttacaact catggatttt    660
ttgcaggaga attagccaca ggactcacca tcagaaccat ggccatgttg agaaggatga    720
atcatggggt ccgtattac tatgagtttg cttgattaat ttccacattt tttctttctt    780
cttaatttta atcagtggtt agatttggtt gtgttccgat agaagaaaag ggggtatcta   840
gagagatgtg aatttcatga agtggttcat gattatgtgt ctttatgcct ttatgtcagc   900
ttacagagaa agtttacaag aatctagaca acatgacaag aatgatgaga ttcactcttc   960
cttcccccat ctttgcatac ccctttatt tggtgagacc ctcttttcc agaatgacag     1020
cattatttta ctatatagta cctcaattt tatattcta aaattttgaa ttcttgaaat    1080
tgaaaggaaa ggactttatt gggtctagca tctcactctc tctttgtgat atgaaccata   1140
tatttcagtg gagcagaagc cctggaaaag aaggctctca tttcaaccct tacagcaact   1200
tgttctctcc tggtgagaga agagatgtgc taacttcaac tctatgttgg ggcatcatgc   1260
tttctgtgct tctctatctt tccctcacaa tgggtccact ttttatgctc aagctctatg   1320
gggttcccta tttggtaatc tcactctcac acttctttta tacatcgcac gccagtgtgg   1380
gttatttgca acctacaccg aagtaatgcc ctataattaa tgaggttaac acatgtccaa   1440
gtccaatatt ttgttcactt atttgaactt gaacatgtgt agatcttcgt catgtggctg   1500
gatttcgtca cgtacttgca tcatcatggt tacaagcaga aactgccttg gtaccgtggc   1560
caggtatccc atttaacaca atttgtttca ttaacattt aagagaattt tttttttcaaa    1620
atagttttcg aaattaagca aataccaagc aaattgttag atctacgctt gtacttgttt   1680
taaagtcaaa ttcatgacca aattgtcctc acaagtccaa accgtccact attttatttt    1740
cacctacttt atagcccaat ttgccatttg gttacttcag aaaagagaac cccatttgta    1800
gtaaatatat tatttatgaa ttatggtagt ttcaacataa aacatactta tgtgcagttt    1860
tgccatcctt caaaagaagg tagaaactta ctccatgtta ctctgtctat atgtaatttc    1920
acaggaatgg agttatctaa ggggtggtct tacaacagta gatcgcgact atggttggat    1980
caacaacatt caccatgaca ttggcaccca tgttatccat cacctttttcc ctcaaattcc   2040
acattatcat ttaatcgaag cggtattaat tctctatttc acaagaaatt attgtatgtc    2100
tgcctatgtg atctaagtca attttcacat aacacatgat caaactttct taattctttc    2160
ttctaaattg aaaaagtgga ttatatgtca attgaaaatt ggtcaagacc acaaacatgt    2220
gatgatctcc cacctacat ataataattt ctcctattct acaatcaata atccttctat     2280
ggtcctgaat tgttccttc tttttttcatt ttcttattct ttttgttgtc ccacaataga    2340
ctaaagcagc aaaggcagtg ctaggaaagt attatcgtga gcctcagaaa tctgggccat    2400
tgccacttca tctaataaag tacttgctcc acagcataag tcaggatcac ttcgttagcg    2460
actctggcga cattgtgtac taccagactg attcccagct ccacaaagat tcttggaccc    2520
agtccaacta aagttttga tgctacattt acctatttca ctcttaaata ctatttccta    2580
tgtaatatgt aatttagaat atgttaccta ctcaaatcaa ttaggtgaca tgtataagct    2640
ttcataaatt atgctagaaa tgcacttact tttcaaagca tgc                      2683
```

<210> SEQ ID NO 19
<211> LENGTH: 160
<212> TYPE: DNA
<213> ORGANISM: Glycine max
<220> FEATURE:

```
<221> NAME/KEY: Intron
<222> LOCATION: (1)..(160)
<223> OTHER INFORMATION: FAD3-1B intron 1

<400> SEQUENCE: 19
gtaactaatt attattacaa attgttatgt tatgttatgt tatgttgttg tgccttttc      60 tcagtgatgc tttagtcatt tcatttcact tggttatgca tgattgttcg ttcatatgtt     120
ctgtcatggt gagttctaat ttgattgatg catggaacag                          160

<210> SEQ ID NO 20
<211> LENGTH: 119
<212> TYPE: DNA
<213> ORGANISM: Glycine max
<220> FEATURE:
<221> NAME/KEY: Intron
<222> LOCATION: (1)..(119)
<223> OTHER INFORMATION: FAD3-1B intron 2

<400> SEQUENCE: 20 gttccttta gcaacttttc atgttcactt tgtccttaaa ttttttttta tgtttgttaa      60
aaaatctttg gtctgattta caacctaac cattttaca actcatggat tttttgcag      119

<210> SEQ ID NO 21
<211> LENGTH: 166
<212> TYPE: DNA
<213> ORGANISM: Glycine max
<220> FEATURE:
<221> NAME/KEY: Intron
<222> LOCATION: (1)..(166)
<223> OTHER INFORMATION: FAD3-1B intron 3A

<400> SEQUENCE: 21
gtattactat gagtttgctt gattaatttc cacattttt ctttcttctt aattttaatc      60
agtggttaga tttggttgtg ttccgataga agaaaagggg gtatctagag agatgtgaat    120
ttcatgaagt ggttcatgat tatgtgtctt tatgccttta tgtcag                   166

<210> SEQ ID NO 22
<211> LENGTH: 156
<212> TYPE: DNA
<213> ORGANISM: Glycine max
<220> FEATURE:
<221> NAME/KEY: Intron
<222> LOCATION: (1)..(156)
<223> OTHER INFORMATION: FAD3-1B intron 3B

<400> SEQUENCE: 22
gtgagaccct cttttccag aatgacagca ttattttact atatagtacc tcaattttta      60
tatttctaaa attttgaatt cttgaaattg aaaggaaagg actttattgg gtctagcatc    120
tcactctctc tttgtgatat gaaccatata tttcag                              156

<210> SEQ ID NO 23
<211> LENGTH: 148
<212> TYPE: DNA
<213> ORGANISM: Glycine max
<220> FEATURE:
<221> NAME/KEY: Intron
<222> LOCATION: (1)..(148)
<223> OTHER INFORMATION: FAD3-1B intron 3C

<400> SEQUENCE: 23
gtaatctcac tctcacactt tctttataca tcgcacgcca gtgtgggtta tttgcaacct    60
acaccgaagt aatgccctat aattaatgag gttaacacat gtccaagtcc aatattttgt   120
```

```
tcacttattt gaacttgaac atgtgtag                                        148
```

<210> SEQ ID NO 24
<211> LENGTH: 351
<212> TYPE: DNA
<213> ORGANISM: Glycine max
<220> FEATURE:
<221> NAME/KEY: Intron
<222> LOCATION: (1)..(351)
<223> OTHER INFORMATION: FAD3-1B intron 4

<400> SEQUENCE: 24

```
taacacaatt tgtttcatta acattttaag agaatttttt tttcaaaata gttttcgaaa     60
ttaagcaaat accaagcaaa ttgttagatc tacgcttgta cttgttttaa agtcaaattc    120
atgaccaaat tgtcctcaca agtccaaacc gtccactatt ttattttcac ctactttata   180
gcccaatttg ccatttggtt acttcagaaa agagaacccc atttgtagta aatatattat   240
ttatgaatta tggtagtttc aacataaaac atacttatgt gcagttttgc catccttcaa   300
aagaaggtag aaacttactc catgttactc tgtctatatg taatttcaca g            351
```

<210> SEQ ID NO 25
<211> LENGTH: 277
<212> TYPE: DNA
<213> ORGANISM: Glycine max
<220> FEATURE:
<221> NAME/KEY: Intron
<222> LOCATION: (1)..(277)
<223> OTHER INFORMATION: FAD3-1B intron 5

<400> SEQUENCE: 25

```
gtattaattc tctatttcac aagaaattat tgtatgtctg cctatgtgat ctaagtcaat    60
tttcacataa cacatgatca aactttctta attctttctt ctaaattgaa aaagtggatt   120
atatgtcaat tgaaaattgg tcaagaccac aaacatgtga tgatctccca ccttacatat   180
aataatttct cctattctac aatcaataat ccttctatgg tcctgaattg ttcctttctt   240
ttttcatttt cttattcttt tgttgtccc acaatag                             277
```

<210> SEQ ID NO 26
<211> LENGTH: 158
<212> TYPE: DNA
<213> ORGANISM: Glycine max
<220> FEATURE:
<221> NAME/KEY: 3'UTR
<222> LOCATION: (1)..(158)
<223> OTHER INFORMATION: FAD3-1B 3' UTR

<400> SEQUENCE: 26

```
agttttttgat gctacattta cctatttcac tcttaaatac tatttcctat gtaatatgta    60
atttagaata tgttacctac tcaaatcaat taggtgacat gtataagctt tcataaatta   120
tgctagaaat gcacttactt ttcaaagcat gctatgtc                           158
```

<210> SEQ ID NO 27
<211> LENGTH: 83
<212> TYPE: DNA
<213> ORGANISM: Glycine max
<220> FEATURE:
<221> NAME/KEY: 5'UTR
<222> LOCATION: (1)..(83)
<223> OTHER INFORMATION: FAD3-1B 5' UTR

<400> SEQUENCE: 27

```
tctaatacga ctcactatag ggcaagcagt ggtatcaacg cagagtacgc ggggggtaaca    60 gagaaagaaa catttgagca aaa                                            83

<210> SEQ ID NO 28
<211> LENGTH: 4083
<212> TYPE: DNA
<213> ORGANISM: Glycine max
<220> FEATURE:
<221> NAME/KEY: gene
<222> LOCATION: (1)..(4083)
<223> OTHER INFORMATION: FATB-1 genomic clone

<400> SEQUENCE: 28
gggaaacaac aaggacgcaa aatgacacaa tagcccttct tccctgtttc cagcttttct    60
ccttctctct ctccatcttc ttcttcttct tcactcagtc aggtacgcaa acaaatctgc   120
tattcattca ttcattcctc tttctctctg atcgcaaact gcacctctac gctccactct   180
tctcattttc tcttcctttc tcgcttctca gatccaactc ctcagataac acaagaccaa   240
acccgctttt tctgcatttc tagactagac gttctaccgg agaaggttct cgattctttt   300
ctcttttaac tttatttta aaataataat aatgagagct ggatgcgtct gttcgttgtg   360
aatttcgagg caatggggtt ctcattttcg ttacagttac agattgcatt gtctgctttc   420
ctcttctccc ttgtttcttt gccttgtctg attttttcgtt tttatttctt actttttaatt   480 tttggggatg atattttttt ctgcattttt tcggtttgcg atgttttcag gattccgatt   540
ccgagtcaga tctgcgccgg cttatacgac gaatttgttc ttattcgcaa cttttcgctt   600
gattggcttg ttttacctct ggaatctcac acgtgatcaa ataagcctgc tattttagtt   660
gaagtagaat ttgttcttta tcggaaagaa ttctatggat ctgttctgaa attggagcta   720
ctgtttcgag ttgctatttt ttttagtagt attaagaaca agtttgcctt ttattttaca   780 ttttttcct ttgcttttgc caaaagttt tatgatcact ctcttctgtt tgtgatataa    840
ctgatgtgct gtgctgttat tatttgttat ttggggtgaa gtataatttt ttgggtgaac   900
ttggagcatt tttagtccga ttgatttctc gatatcattt aaggctaagg ttgacctcta   960
ccacgcgttt gcgtttgatg ttttttccat tttttttta tctcatatct tttacagtgt   1020
ttgcctattt gcatttctct tctttatccc cttttctgtgg aaaggtggga gggaaaatgt  1080
attttttttt tctcttctaa cttgcgtata ttttgcatgc agcgacctta gaaattcatt  1140
atggtggcaa cagctgctac ttcatcattt ttccctgtta cttcaccctc gccggactct  1200
ggtggagcag gcagcaaact tggtggtggg cctgcaaacc ttggaggact aaaatccaaa  1260
tctgcgtctt ctggtggctt gaaggcaaag gcgcaagccc cttcgaaaat taatggaacc  1320
acagttgtta catctaaaga aggcttcaag catgatgatg atctaccttc gcctcccccc  1380
agaactttta tcaaccagtt gcctgattgg agcatgcttc ttgctgctat cacaacaatt  1440
ttcttggccg ctgaaaagca gtggatgatg cttgattgga agccacggcg acctgacatg  1500
cttattgacc cctttgggat aggaaaaaat tgttcaggat gtcttgtgtt ccgtgaaaac  1560
ttttctatta gatcatatga gattggtgct gatcgtaccg catctataga aacagtaatg  1620
aaccatttgc aagtaagtcc gtcctcatac aagtgaatct ttatgatctt cagagatgag  1680
tatgctttga ctaagatagg gctgtttatt tagacactgt aattcaattt catatataga  1740
taatatcatt ctgttgttac ttttcatact atatttatat caactatttg cttaacaaca  1800
ggaaactgca cttaatcatg ttaaaagtgc tgggcttctt ggtgatggct ttggttccac  1860
gccagaaatg tgcaaaaaga acttgatatg ggtggttact cggatgcagg ttgtggtgga  1920
```

-continued

```
acgctatcct acatggttag tcatctagat tcaaccatta catgtgattt gcaatgtatc    1980
catgttaagc tgctatttct ctgtctattt tagtaatctt tatgaggaat gatcactcct    2040
aaatatattc atggtaatta ttgagactta attatgagaa ccaaaatgct ttggaaattt    2100
gtctgggatg aaaattgatt agatacacaa gctttataca tgatgaacta tgggaaacct    2160
tgtgcaacag agctattgat ctgtacaaga gatgtagtat agcattaatt acatgttatt    2220
agataaggtg acttatcctt gtttaattat tgtaaaaata gaagctgata ctatgtattc    2280
tttgcatttg ttttcttacc agttatatat accctctgtt ctgtttgagt actactagat    2340
gtataaagaa tgcaattatt ctgacttctt ggtgttgggt tgaagttaga taagctatta    2400
gtattattat ggttattcta aatctaatta tctgaaattg tgtgtctata tttgcttcag    2460
gggtgacata gttcaagtgg acacttgggt ttctggatca gggaagaatg gtatgcgtcg    2520
tgattggctt ttacgtgact gcaaaactgg tgaaatcttg acaagagctt ccaggtagaa    2580
atcattctct gtaattttcc ttcccctttc cttctgcttc aagcaaattt taagatgtgt    2640
atcttaatgt gcacgatgct gattggacac aattttaaat ctttcaaaca tttacaaaag    2700
ttatggaacc ctttctttc tctcttgaag atgcaaattt gtcacgactg aagtttgagg    2760
aaatcatttg aattttgcaa tgttaaaaaa gataatgaac tacatatttt gcaggcaaaa    2820
acctctaatt gaacaaactg aacattgtat cttagtttat ttatcagact ttatcatgtg    2880
tactgatgca tcaccttgga gcttgtaatg aattacatat tagcattttc tgaactgtat    2940
gttatggttt tggtgatcta cagtgtttgg gtcatgatga ataagctgac acggaggctg    3000
tctaaaattc cagaagaagt cagacaggag ataggatctt attttgtgga ttctgatcca    3060
attctagaag aggataacag aaaactgact aaacttgacg acaacacagc ggattatatt    3120
cgtaccggtt taagtgtatg tcaactagtt tttttgtaat tgttgtcatt aatttctttt    3180
cttaaattat ttcagatgtt gctttctaat tagtttacat tatgtatctt cattcttcca    3240
gtctaggtgg agtgatctag atatcaatca gcatgtcaac aatgtgaagt acattgactg    3300
gattctggag gtatttttct gttcttgtat tctaatccac tgcagtcctt gttttgttgt    3360
taaccaaagg actgtccttt gattgtttgc agagtgctcc acagccaatc ttggagagtc    3420
atgagctttc ttccgtgact ttagagtata ggagggagtg tggtagggac agtgtgctgg    3480
attccctgac tgctgtatct ggggccgaca tgggcaatct agctcacagt ggacatgttg    3540
agtgcaagca tttgcttcga ctcgaaaatg gtgctgagat tgtgaggggc aggactgagt    3600
ggaggcccaa acctatgaac aacattggtg ttgtgaacca ggttccagca gaaagcacct    3660
aagattttga aatggttaac ggttggagtt gcatcagtct ccttgctatg tttagactta    3720
ttctggcctc tggggagagt tttgcttgtg tctgtccaat caatctacat atctttatat    3780
ccttctaatt tgtgttactt tggtgggtaa ggggaaaag ctgcagtaaa cctcattctc    3840
tctttctgct gctccatatt tcatttcatc tctgattgcg ctactgctag gctgtcttca    3900
atatttaatt gcttgatcaa aatagctagg catgtatatt attattcttt tctcttggct    3960
caattaaaga tgcaattttc attgtgaaca cagcataact attattctta ttattttgt    4020 atagcctgta tgcacgaatg acttgtccat ccaatacaac cgtgattgta tgctccagct    4080
cag                                                                  4083
```

<210> SEQ ID NO 29
<211> LENGTH: 109
<212> TYPE: DNA

```
<213> ORGANISM: Glycine max
<220> FEATURE:
<221> NAME/KEY: Intron
<222> LOCATION: (1)..(109)
<223> OTHER INFORMATION: FATB-1 intron I

<400> SEQUENCE: 29
gtacgcaaac aaatctgcta ttcattcatt cattcctctt tctctctgat cgcaaactgc      60
acctctacgc tccactcttc tcattttctc ttcctttctc gcttctcag                 109

<210> SEQ ID NO 30
<211> LENGTH: 836
<212> TYPE: DNA
<213> ORGANISM: Glycine max
<220> FEATURE:
<221> NAME/KEY: Intron
<222> LOCATION: (1)..(836)
<223> OTHER INFORMATION: FATB-1 intron II

<400> SEQUENCE: 30
gttctcgatt ctttctctt taactttat ttttaaaata ataataatga gagctggatg        60
cgtctgttcg ttgtgaattt cgaggcaatg gggttctcat tttcgttaca gttacagatt    120
gcattgtctg ctttcctctt ctcccttgtt tctttgcctt gtctgatttt tcgttttat     180 ttcttacttt taattttggg ggatggatat ttttctgca ttttttcggt ttgcgatgtt     240
ttcaggattc cgattccgag tcagatctgc gccggcttat acgacgaatt tgttcttatt    300
cgcaactttt cgcttgattg gcttgtttta cctctggaat ctcacacgtg atcaaataag    360
cctgctattt tagttgaagt agaatttgtt ctttatcgga aagaattcta tggatctgtt    420
ctgaaattgg agctactgtt tcgagttgct attttttta gtagtattaa aacaagttt     480 gccttttatt ttacattttt ttcctttgct tttgccaaaa gtttttatga tcactctctt    540
ctgtttgtga tataactgat gtgctgtgct gttattattt gttatttggg gtgaagtata    600
attttttggg tgaacttgga gcatttttag tccgattgat ttctcgatat catttaaggc    660
taaggttgac ctctaccacg cgtttgcgtt tgatgttttt tccattttttt ttttatctca    720 tatcttttac agtgtttgcc tatttgcatt tctcttcttt atccccttttc tgtggaaggt    780 gggagggaaa atgtattttt ttttttctctt ctaacttgcg tatattttgc atgcag       836

<210> SEQ ID NO 31
<211> LENGTH: 169
<212> TYPE: DNA
<213> ORGANISM: Glycine max
<220> FEATURE:
<221> NAME/KEY: Intron
<222> LOCATION: (1)..(169)
<223> OTHER INFORMATION: FATB-1 intron III

<400> SEQUENCE: 31
gtaagtccgt cctcatacaa gtgaatcttt atgatcttca gagatgagta tgctttgact     60
aagatagggc tgtttatta gacactgtaa ttcaattca tatatagata atatcattct      120
gttgttactt ttcatactat atttatatca actatttgct taacaacag                169

<210> SEQ ID NO 32
<211> LENGTH: 525
<212> TYPE: DNA
<213> ORGANISM: Glycine max
<220> FEATURE:
<221> NAME/KEY: Intron
<222> LOCATION: (1)..(525)
<223> OTHER INFORMATION: FATB-1 intron IV
```

<400> SEQUENCE: 32

```
gttagtcatc tagattcaac cattacatgt gatttgcaat gtatccatgt taagctgcta       60
tttctctgtc tatttagta atctttatga ggaatgatca ctcctaaata tattcatggt      120
aattattgag acttaattat gagaaccaaa atgctttgga aatttgtctg ggatgaaaat      180
tgattagata cacaagcttt atacatgatg aactatggga aaccttgtgc aacagagcta      240
ttgatctgta caagagatgt agtatagcat taattacatg ttattagata aggtgactta      300
tccttgttta attattgtaa aaatagaagc tgatactatg tattctttgc atttgttttc      360
ttaccagtta tatataccct ctgttctgtt tgagtactac tagatgtata aagaatgcaa      420
ttattctgac ttcttggtgt tgggttgaag ttagataagc cattagtatt attatggtta      480
ttctaaatct aattatctga aattgtgtgt ctatatttgc ttcag                     525
```

<210> SEQ ID NO 33
<211> LENGTH: 389
<212> TYPE: DNA
<213> ORGANISM: Glycine max
<220> FEATURE:
<221> NAME/KEY: Intron
<222> LOCATION: (1)..(389)
<223> OTHER INFORMATION: FATB-1 intron V

<400> SEQUENCE: 33

```
gtagaaatca ttctctgtaa ttttccttcc cctttccttc tgcttcaagc aaattttaag       60
atgtgtatct taatgtgcac gatgctgatt ggacacaatt ttaaatcttt caaacattta      120
caaaagttat ggaaccctt cttttctctc ttgaagatgc aaatttgtca cgactgaagt      180
ttgaggaaat catttgaatt ttgcaatgtt aaaaagata atgaactaca tattttgcag      240
gcaaaaacct ctaattgaac aaactgaaca ttgtatctta gtttattat cagactttat      300
catgtgtact gatgcatcac cttggagctt gtaatgaatt acatattagc attttctgaa      360
ctgtatgtta tggttttggt gatctacag                                      389
```

<210> SEQ ID NO 34
<211> LENGTH: 106
<212> TYPE: DNA
<213> ORGANISM: Glycine max
<220> FEATURE:
<221> NAME/KEY: Intron
<222> LOCATION: (1)..(106)
<223> OTHER INFORMATION: FATB-1 intron VI

<400> SEQUENCE: 34

```
tatgtcaact agttttttg taattgttgt cattaatttc ttttcttaaa ttatttcaga       60
tgttgctttc taattagttt acattatgta tcttcattct tccagt                   106
```

<210> SEQ ID NO 35
<211> LENGTH: 82
<212> TYPE: DNA
<213> ORGANISM: Glycine max
<220> FEATURE:
<221> NAME/KEY: Intron
<222> LOCATION: (1)..(82)
<223> OTHER INFORMATION: FATB-1 intron VII

<400> SEQUENCE: 35

```
gtattttct gttcttgtat tctaatccac tgcagtcctt gttttgttgt taaccaaagg       60
actgtccttt gattgtttgc ag                                              82
```

<210> SEQ ID NO 36
<211> LENGTH: 208
<212> TYPE: DNA
<213> ORGANISM: Glycine max
<220> FEATURE:
<221> NAME/KEY: 3'UTR
<222> LOCATION: (1)..(208)
<223> OTHER INFORMATION: FATB-1 3' UTR

<400> SEQUENCE: 36

```
gatttgaaat ggttaacgat tggagttgca tcagtctcct tgctatgttt agacttattc     60
tggttccctg gggagagttt tgcttgtgtc tatccaatca atctacatgt ctttaaatat    120
atacaccttc taatttgtga tactttggtg ggtaaggggg aaaagcagca gtaaatctca    180
ttctcattgt aattaaaaaa aaaaaaaa                                       208
```

<210> SEQ ID NO 37
<211> LENGTH: 229
<212> TYPE: DNA
<213> ORGANISM: Glycine max
<220> FEATURE:
<221> NAME/KEY: 5'UTR
<222> LOCATION: (1)..(229)
<223> OTHER INFORMATION: FATB-1 5' UTR

<400> SEQUENCE: 37

```
acaattacac tgtctctctc ttttccaaaa ttagggaaac aacaaggacg caaaatgaca     60
caatagccct tcttccctgt ttccagcttt tctccttctc tctctctcca tcttcttctt    120
cttcttcact cagtcagatc caactcctca gataacacaa gaccaaaccc gcttttctg     180
catttctaga ctagacgttc taccggagaa gcgaccttag aaattcatt                229
```

<210> SEQ ID NO 38
<211> LENGTH: 1398
<212> TYPE: DNA
<213> ORGANISM: Cuphea pulcherrima
<220> FEATURE:
<221> NAME/KEY: gene
<222> LOCATION: (1)..(1398)
<223> OTHER INFORMATION: KAS I gene

<400> SEQUENCE: 38

```
atgcattccc tccagtcacc ctcccttcgg gcctccccgc tcgacccctt ccgccccaaa     60
tcatccaccg tccgcccccct ccaccgagca tcaattccca acgtccgggc cgcttccccc    120
accgtctccg ctcccaagcg cgagaccgac cccaagaagc gcgtcgtgat caccggaatg    180
ggccttgtct ccgttttcgg ctccgacgtc gatgcgtact acgacaagct cctgtcaggc    240
gagagcggga tcggcccaat cgaccgcttc gacgcctcca gttccccac caggttcggc    300
ggccagattc gtggcttcaa ctccatggga tacattgacg gcaaaaacga caggcggctt    360
gatgattgcc ttcgctactg cattgtcgcc gggaagaagt ctcttgagga cgccgatctc    420
ggtgccgacc gcctctccaa gatcgacaag gagagagccg gagtgctggt tgggacagga    480
atgggtggtc tgactgtctt ctctgacggg gttcaatctc ttatcgagaa gggtcaccgg    540
aaaatcaccc ctttcttcat ccctatgcc attacaaaca tggggtctgc cctgctcgct    600
attgaactcg gtctgatggg cccaaactat tcaatttcca ctgcatgtgc cacttccaac    660
tactgcttcc atgctgctgc taatcatatc cgccgtggtg aggctgatct tatgattgct    720
ggaggcactg aggccgcaat cattccaatt gggttgggag ctttgtggc ttgcagggct    780
ctgtctcaaa ggaacgatga ccctcagact gcctctaggc cctgggataa agaccgtgat    840
```

```
ggttttgtga tgggtgaagg tgctggagtg ttggtgctgg agagcttgga acatgcaatg    900
aaacgaggag cacctattat tgcagagtat ttgggaggtg caatcaactg tgatgcttat    960
cacatgactg acccaagggc tgatggtctc ggtgtctcct cttgcattga gagtagcctt   1020
gaagatgctg gcgtctcacc tgaagaggtc aattacataa atgctcatgc gacttctact   1080
ctagctgggg atctcgccga gataaatgcc atcaagaagg ttttcaagaa cacaaaggat   1140
atcaaaatta atgcaactaa gtcaatgatc ggacactgtc ttggagcctc tggaggtctt   1200
gaagctatag cgactattaa gggaataaac accggctggc ttcatcccag cattaatcaa   1260
ttcaatcctg agccatccgt ggagttcgac actgttgcca acaagaagca gcaacacgaa   1320
gttaatgttg cgatctcgaa ttcatttgga ttcggaggcc acaactcagt cgtggctttc   1380
tcggctttca agccatga                                                 1398

<210> SEQ ID NO 39
<211> LENGTH: 1218
<212> TYPE: DNA
<213> ORGANISM: Cuphea pulcherrima

<400> SEQUENCE: 39
atgggtgtgg tgactcctct aggccatgac cctgatgttt ctacaataa tctgcttgat     60 ggaacgagtg gcataagcga gatagagacc tttgattgtg ctcaatttcc tacgagaatt    120
gctggagaga tcaagtcttt ctccacagat ggttgggtgg ccccgaagct ctctaagagg    180
atggacaagt tcatgctata catgctgacc gctggcaaga agcattaac agatggtgga    240 atcaccgaag atgtgatgaa agagctagat aaaagaaaat gcggagttct cattggctca    300
gcaatgggtg gaatgaaggt attcaatgat gccattgaag ccctaaggat ttcatataag    360
aagatgaatc ccttttgtgt acctttcgct accacaaata tgggatcagc tatgcttgca    420
atggacttgg gatggatggg gcccaactac tcgatatcta ctgcttgtgc aacgagtaac    480
ttttgtataa tgaatgctgc gaaccatata atcagaggcg aagcagatgt gatgctttgc    540
gggggctcag atgcggtaat catacctatt ggtatgggag gttttgttgc atgccgagct    600
ttgtcccaga gaaattccga ccctactaaa gcttcaagac catgggacag taatcgtgat    660
ggatttgtta tgggggaagg agctggagtg ctactactag aggagttgga gcatgcaaag    720
aaaagaggtg cgactatttta cgcagaattt ctaggtggga gtttcacttg cgatgcctac    780
cacatgaccg agcctcaccc tgatggagct ggagtgattc tctgcataga gaaggctttg    840
gctcagtcag gagtctctag ggaagacgta aattacataa atgcccatgc cacatccact    900
ccggctggag atatcaaaga gtaccaagct cttatccact gtttcggcca aaacagagag    960
ttaaaagtta attcaaccaa atcaatgatt ggtcaccttc tcggagcagc cggtggtgtg   1020
gaagcagttt cagtagttca ggcaataagg actgggtgga tccatccgaa tattaatttg   1080
gaaaacccag atgaaggcgt ggatacaaaa ttgctcgtgg gtcctaagaa ggagagactg   1140
aacgttaagg tcggtttgtc taattcattt gggtttggtg ggcacaactc gtccatactc   1200 ttcgccccctt acatctag                                                1218

<210> SEQ ID NO 40
<211> LENGTH: 1191
<212> TYPE: DNA
<213> ORGANISM: Ricinus communis
<220> FEATURE:
<221> NAME/KEY: gene
<222> LOCATION: (1)..(1191)
```

<223> OTHER INFORMATION: delta-9 desaturase

<400> SEQUENCE: 40

| | | | | | |
|---|---|---|---|---|---|
| atggctctca | agctcaatcc | tttcctttct | caaacccaaa | agttaccttc | tttcgctctt | 60 |
| ccaccaatgg | ccagtaccag | atctcctaag | ttctacatgg | cctctaccct | caagtctggt | 120 |
| tctaaggaag | ttgagaatct | caagaagcct | tcatgcctc | ctcgggaggt | acatgttcag | 180 |
| gttaccatt | ctatgccacc | ccaaaagatt | gagatcttta | atccctaga | caattgggct | 240 |
| gaggagaaca | ttctggttca | tctgaagcca | gttgagaaat | gttggcaacc | gcaggatttt | 300 |
| ttgccagatc | ccgcctctga | tggatttgat | gagcaagtca | gggaactcag | ggagagagca | 360 |
| aaggagattc | ctgatgatta | ttttgttgtt | ttggttggag | acatgataac | ggaagaagcc | 420 |
| cttcccactt | atcaaacaat | gctgaatacc | ttggatggag | ttcgggatga | aacaggtgca | 480 |
| agtcctactt | cttgggcaat | ttggacaagg | gcatggactg | cggaagagaa | tagacatggt | 540 |
| gacctcctca | ataagtatct | ctacctatct | ggacgagtgg | acatgaggca | aattgagaag | 600 |
| acaattcaat | atttgattgg | ttcaggaatg | gatccacgga | cagaaaacag | tccatacctt | 660 |
| gggttcatct | atacatcatt | ccaggaaagg | gcaaccttca | tttctcatgg | gaacactgcc | 720 |
| cgacaagcca | aagagcatgg | agacataaag | ttggctcaaa | tatgtggtac | aattgctgca | 780 |
| gatgagaagc | gccatgagac | agcctacaca | aagatagtgg | aaaaactctt | tgagattgat | 840 |
| cctgatggaa | ctgttttggc | ttttgctgat | atgatgagaa | agaaaatttc | tatgcctgca | 900 |
| cacttgatgt | atgatggccg | agatgataat | cttttgacc | acttttcagc | tgttgcgcag | 960 |
| cgtcttggag | tctacacagc | aaaggattat | gcagatatat | ggagttctt | ggtgggcaga | 1020 |
| tggaaggtgg | ataaactaac | gggccttca | gctgagggac | aaaaggctca | ggactatgtt | 1080 |
| tgtcggttac | ctccaagaat | tagaaggctg | aagagagag | ctcaaggaag | ggcaaaggaa | 1140 |
| gcacccacca | tgcctttcag | ctggattttc | gataggcaag | tgaagctgta | g | 1191 |

<210> SEQ ID NO 41
<211> LENGTH: 1194
<212> TYPE: DNA
<213> ORGANISM: Simmondsia chinensis
<220> FEATURE:
<221> NAME/KEY: gene
<222> LOCATION: (1)..(1194)
<223> OTHER INFORMATION: delta-9 desaturase

<400> SEQUENCE: 41

| | | | | | |
|---|---|---|---|---|---|
| atggcgttga | agcttcacca | cacggccttc | aatccttcca | tggcggttac | ctcttcggga | 60 |
| cttcctcgat | cgtatcacct | cagatctcac | cgcgttttca | tggcttcttc | tacaattgga | 120 |
| attacttcta | aggagatacc | caatgccaaa | aagcctcaca | tgcctcctag | agaagctcat | 180 |
| gtgcaaaaga | cccattcaat | gccgcctcaa | aagattgaga | ttttcaaatc | cttggagggt | 240 |
| tgggctgagg | agaatgtctt | ggtgcatctt | aaacctgtgg | agaagtgttg | gcaaccacaa | 300 |
| gattttctac | ccgacccggc | ctccgaggga | tttatggatc | aagtcaagga | gttgagggaa | 360 |
| agaaccaaag | aaatcccgga | tgagtacctt | gtggtgttgg | ttggcgatat | gatcactgaa | 420 |
| gaagctcttc | cgacctacca | gacgatgcta | aacacgctcg | atggagtacg | tgatgagacg | 480 |
| ggtgccagcc | ttacttcttg | ggctatctgg | acccgggcat | ggaccgctga | agagaatagg | 540 |
| cacggtgatc | ttttgaacaa | gtatctttac | cttactggtc | gagttgacat | gaagcagata | 600 |
| gagaagacaa | tccagtatct | aatcggatct | ggaatggacc | ctcgaagtga | aaacaacccc | 660 |
| tatctaggct | tcatctacac | ttccttccaa | gagagagcaa | ccttcatctc | ccatggaaac | 720 |

```
accgctaggc tcgccaaaga ccacggcgac tttcaactag cacaagtatg tggcatcatc    780
gctgcagatg agaagcgcca cgaaactgcc tacacaaaaa ttgtcgaaaa gctctttgaa    840
atcgacccag acggcgctgt tctagcacta gctgacatga tgagaaagaa ggtttccatg    900
ccagcccact taatgtatga tggcaaagat gacaatctct tgagaactac tcagccgtc    960 gctcaacaaa ttggagttta caccgcgaag gactacgctg acatcctcga cacctcgtt   1020 aatcgctgga agtcgagaa tttaatgggt ctgtctggcg agggacataa ggctcaagat   1080
ttcgtatgtg ggttggcccc gaggatcagg aaactcgggg agagagctca gtcgctaagc   1140
aaaccggtat ctcttgtccc cttcagctgg attttcaaca aggaattgaa ggtt         1194

<210> SEQ ID NO 42
<211> LENGTH: 2077
<212> TYPE: DNA
<213> ORGANISM: Artificial
<220> FEATURE:
<223> OTHER INFORMATION: FATB-2 cDNA Contig

<400> SEQUENCE: 42
gagggaaaca aggaagcgaa atgacacaat agtccttctt ccctgtttcc actttccagg     60
ttttctcctt ctcgtttgtt gagcgctttt ctctccctct ccctcttctt cactcagtca    120
gctgccgtag aaattcatta tggtggcaac agctgcaact tcatcatttt tccctgttac    180
ttcaccctcg ccggactctg gtggacatgc aaagttactc aaaataatcg ctggccctat    240
cacattattg ttaatattct tccctttcttt accttctact ttccgaatcc agaaaacacc    300
acaacaccac ccagaattgt tgggttccat tctcaaaaca gagaacaaga agaagaagaa    360
agagagagag tgaaaacggg aaaagcaaaa agttgtttct gtgattgatt ctctgcaacc    420
gaatcatcat cagccacttc ttcccgtttc atctctccca tttcttcttt tcttccgctc    480
tggttcagta aggcgaagag ggttaacgtt attcataatg gttgcaacag ccgctacggc    540
gtcgtttctt cccgtgcctt tgccagacgc tggaaaaggg aaacccaaga aactgggtgg    600
tggtggcggt ggcggtggcg gttctgtgaa cctcggagga ctcaaacaga aacaaggttt    660
gtgcggtggc ttgcaggtca aggcaaacgc acaagcccct ccgaagaccg tggagaaggt    720
tgagaatgat ttgtcgtcgt cgtcctcgtc gatttcgcac gccccgagga ctttcatcaa    780
ccagttacct gactggagca tgcttctggc cgccatcacc accgtgttcc tggcggcgga    840
gaagcagtgg atgatgctgg attggaagcc gcggcgcccc gacatgctca ttgacccctt    900
tgggattggg aagatcgtgc aggatgggct tgtgttcagg cagaacttcc ccattaggtc    960
ctatgagatt ggcgccgata aaaccgcgtc tatcgagact ttaatgaatc atttgcagga   1020
gactgcactt aatcatgtta agactgctgg gcttcttggt gatggatttg gttccacgcc   1080
tgaaatgtgc aaaagaacc tgatatgggt ggtgactaag atgcaggttg tggttgataa   1140
atatcccaca tggggtgatg ttgttcaagt agacacttgg gtatctgcat cagggaagaa   1200
tggtatgtgt cgtgattggc ttgtgcgtga cgcgaaatct ggtgaaatct tgacaagagc   1260
ctccagtgtt tgggtcatga tgaataaagt gacaagaaga ctgtctaaaa ttcccgaaga   1320
agtcagggca gagataagct cttattttgt ggactctgct ccagttgtgc cagaggataa   1380
cagaaaacta accaaacttg atgaatccgc taatttcatt cgcactggtt taagtcccag   1440
atggaatgat ctagatgtga atcagcatgt taacaatgtg aagtatgttg ggtggattct   1500
ggagagtgct ccacagccac ttttggagag ccatgagctg tgtgccatga cattggagta   1560
```

```
caggagggag tgtggcagga acagtgtgct ggattccctc tctgatctct ctggtgctga    1620
tgtaggaaac ttggcagatg gtggattttt tgagtgcaag cacttgcttc gacttgatga    1680
tggtgctgag attgtgaggg gtaggactca atggaggccc aaacctttaa gcagcaactt    1740
tggtcatgtt ttgagtcagg ttccagttcc agcagaaagc acctgaatct tatcttattg    1800
attggcatca ctggaggagg agtggcataa attcatagag agctttgctt gtttttatca    1860
aatctacgta tcttaaaata tatataaaag aaagtgtgtt actttggcta aaaaagggga    1920
ggggaagtag aaagtaaaaa aaaaaaaaaa aatctcgctc tcatgatttt gtaattaaaa    1980
aatagctcct agcactactt tctcctacct gctccatttt ctgtttcact tatggttatg    2040
ctgctgcttg gtgtcatcaa tatttaattg tttcatc                             2077

<210> SEQ ID NO 43
<211> LENGTH: 4634
<212> TYPE: DNA
<213> ORGANISM: Glycine max

<400> SEQUENCE: 43
ggaaacaagg aagcgaaatg acacaatagt ccttcttccc tgtttccact ttccaggttt      60
tctccttctc gtttgttgag cgcttttctc tccctctccc tcttcttcac tcagtcaggt     120
acgctaacaa atctgctatt caatcaattc ctctttctct ctgatctacg tacgtgtccg     180
caaactgcac ctccactctc cactcattcc atctaatctt ccctttttcgc ttcagagatc    240 caactcctca tataattcaa gacaaaatcc cgcgttttct gcatttctag acgttctacc     300
ctacaaggtt ctcgattctt cttttttctt tttttttaga ctattattat tttaaaaaaa     360
taaaaataat aatgagagct ggatgcgtct gttcgttgtg aatttcgagg caatggggtt     420
ctgattttcg ttacagattg cattgtttgc tttcctcctc tccgtttttt ctttgccttg     480 ttttttatttt taattttggg gatgttttcg gtcttgcctt tgtttctgca tttttttttc     540
ggtttgcgat gttttcagat ctgcgctggc ttatacgacg aatttgttct tattcgtgac     600
tttccgcttg attgacctgt tttacctctg gaatctcaca cgtgatcaaa taaggctgct     660
attttagttg aagtagaatc tatacacact ttgtagcatt ctttttacga tcacttacac     720
gggtggtttt taatcaggct ttttttgtgg gggtataaac atcttcctcc tcgattcttt     780
ccgataaaag cttaattgga ttataggaag tgggaaacaa tgcgtgggag ctctttggtt     840 tgttttttcgt aggttaaact tgcaggttta agttctgaat caggagttcc aaatatagag     900
gctgggggca taaaaaaaga gaattctatg gatctgttct gaaattggag ccactgtttc     960
gagttgctat ttttttacta gtattaataa gaacaagttt gcttttatt ttacatttt     1020 tcccgtttct tttgccaaaa gtatttatga tcactctctt ctgttgtgat attacttat     1080 aagtgctgtg ctgtaattat tgttatttg gggtgaagta taattttggg gtgaacttgg     1140
agcgttttta gttagattga tttctcgata tcatttaagg tttaggttga ccccttccac     1200
tcgtttgtgg ttgattgttt ttttttttt atctcttatc atttacagtg cttctttgcc     1260
tatttttttc attatcccct ttcgtgaaag gtaggagaag aaaaacaatg acttgcgtaa     1320
attttgcatg cagctgccgt agaaattcat tatggtggca acagctgcaa cttcatcatt     1380
tttccctgtt acttcacccct cgccggactc tggtggacat gcaaagttac tcaaaataat     1440
cgctggccct atcacattat tgttaatatt ctttcccttct ttaccttcta ctttccgaat     1500
ccagaaaaca ccacaacacc acccagaatt gttgggttcc attctcaaaa cagagaacaa     1560
gaagaagaag aaagagagag agtgaaaacg ggaaaagcaa aaagttgttt ctgtgattga     1620
```

```
ttctctgcaa ccgaatcatc atcagccact tcttcccgtt tcatctctcc catttcttct    1680
tttcttccgc tctggttcag taaggcgaag agggttaacg ttattcataa tggttgcaac    1740
agccgctacg gcgtcgtttc ttcccgtgcc tttgccagac gctggaaaag gaaacccaa     1800 gaaactgggt ggtggtggcg gtggcggtgg cggttctgtg aacctcggag gactcaaaca    1860
gaaacaaggt ttgtgcggtg gcttgcaggt caaggcaaac gcacaagccc ctccgaagac    1920
cgtggagaag gttgagaatg atttgtcgtc gtcgtcctcg tcgatttcgc acgcccgag     1980 gactttcatc aaccagttac ctgactggag catgcttctg gccgccatca ccaccgtgtt    2040
cctggcggcg gagaagcagt ggatgatgct ggattggaag ccgcggcgcc ccgacatgct    2100
cattgacccc tttgggattg ggaagatcgt gcaggatggg cttgtgttca ggcagaactt    2160
ccccattagg tcctatgaga ttggcgccga taaaaccgcg tctatcgaga ctttaatgaa    2220
tcatttgcag gtcagctttt gcaaaaaatt gctgagaatt gcattcagca atcacgataa    2280
atataacttt taataaatta ttatagaagt taagtaactt atcacgggtt gtcaacaaaa    2340
atttagagaa taattgcata ggacaaaact tacctacagt tcgtttgaca ttttttgtgt    2400
cgttttaaaa tcaaaattaa aatttatct tggtaatttg cagattatta gatacaactc     2460
caatttcgat caaagaacaa tgccaaaaac acctatggaa tctaagtttt gtgcaattgc    2520
ttattgatga ttttatttta ttgcctaaat tgtctgtttt ccaaacagga gactgcactt    2580
aatcatgtta agactgctgg gcttcttagt gatggatttg gttccacgct gaaatgtgca    2640
aaaagaacct gatatgggtg gtgactaaga tgcaggttgt ggttgataaa tatcccacat    2700
ggtaagttgg tgtgactaag aagaacctt tgatgtgtg aagaattgca aaggcgtcca      2760
tgctcagctg tgaaatcttc ttttgcctta ctcatcttta ctttgacttt atatagtatc    2820
tggttgaatt attttgtact tctgcatttg tttctgtcac ttgtgctttt tgtttcaca    2880 aaattggtat gatagttagg aacttgggat taaaggcatg tttggaatat attgtgattg    2940
tgaattattt ttaaaaatat tttcactttt caaaatctat ctcatgaatc tgtaaaaata   3000
agaataaaaa ataaaactac tgtaatgtgt ataaaaaatt cttcttggat ggtaattgat    3060
ctgataagca catgcttttt acataatgaa ttatatgaag tcctttgcct taagtctgtt    3120
agactgggta tgagatatgg tagtaaaatc tttttacatt ccgtacattt ttttgcatat   3180
ttctgtctta ttattgtaaa atgttggatg catatacagg ttttcaaaag aagcaactta    3240
taccatgtgc ccttttctgc attttggtct gttcgagaat aatctcttta gtaaattctg    3300
aatctgttca tctgaagttg agtgaatcta tatttgcttc aggggtgatg ttgttcaagt    3360
agacacttgg gtatctgcat cagggaagaa tggtatgtgt cgtgattggc ttgtgcgtga    3420
cgccaaatct ggtgaaatct tgacaagagc ctccaggtag atatcagttt caggaatcct    3480
ttttttctgt tgcctataga catgttttga agagttttc tgaatctgaa tgtttctctc     3540
tggtgatttg gcactgcttt taatctcacg aggctgtgtg aagttatcta ttatcatatt    3600
tactttctct taatacacca ctattgaaag gcaattcatt acagatttaa gcatacaaaa    3660
ttttgttgat gataattttt taatctacca acagtatcta atatcttctt aatttgttat    3720
taagtaccag ccttcaactt gtgtacatgt tgcaccttgg tgctacgaac ttataagcat    3780
tttctgattg gttgagtttg attttgattt tgatgttatg cagtgtttgg gtcatgatga    3840
ataaagtgac aagaagactg tctaaaattc ccgaagaagt cagggcagag ataagctctt    3900
attttgtgga ttctgctcca gttgtgccag aggataacag aaaactaacc aaacttgatg    3960
```

| | |
|---|---|
| attcagctaa tttcattcgc actggtttaa gtcccagatg gaatgatcta gatgtgaatc | 4020 |
| agcatgttaa caatgtgaag tatgttgggt ggattctgga gagtgctcca cagccacttt | 4080 |
| tggagagcca tgagctgtgt gccatgacat tggagtacag gagggagtgt ggcaggaaca | 4140 |
| gtgtgctgga ttccctctct gatctctctg gtgctgatgt aggaaacttg gcagatggtg | 4200 |
| gatttttga gtgcaagcac ttgcttcgac ttgatgatgg tgctgagatt gtgaggggta | 4260 |
| ggactcaatg gaggcccaaa cctttaagca gcaactttgg tcatgttttg agtcaggttc | 4320 |
| cagttccagc agaaagcacc tgaatcttat cttattgatt ggcatcactg gaggaggagt | 4380 |
| ggcataaatt catagagagc tttgcttgtt tttatcaaat ctacgtatct taaaatatat | 4440 |
| ataaaagaaa gtgtgttact ttggctaaaa aaggggaggg gaagtagaaa gtaaaaaaaa | 4500 |
| aaaaaaaaat ctcgctctca tgattttgta attaaaaaat agctcctagc actactttct | 4560 |
| cctacctgct ccattttctg tttcacttat ggttatgctg ctgcttggtg tcatcaatat | 4620 |
| ttaattgttt catc | 4634 |

<210> SEQ ID NO 44
<211> LENGTH: 1215
<212> TYPE: DNA
<213> ORGANISM: Glycine max

<400> SEQUENCE: 44

| | |
|---|---|
| gtacgctaac aaatctgcta ttcaatcaat tcctctttct ctctgatcta cgtacgtgtc | 60 |
| cgcaaactgc acctccactc tccactcatt ccatctaatc ttccctttc gcttcagaga | 120 |
| tccaactcct catataattc aagacaaaat cccgcgtttt ctgcatttct agacgttcta | 180 |
| ccctacaagg ttctcgattc ttctttttc tttttttta gactattatt attttaaaaa | 240 |
| aataaaaata ataatgagag ctggatgcgt ctgttcgttg tgaatttcga ggcaatgggg | 300 |
| ttctgatttt cgttacagat tgcattgttt gcttcctcc tctccgtttt tctttgcct | 360 |
| tgttttatt tttaattttg gggatgtttt cggtcttgcc tttgtttctg cattttttt | 420 |
| tcggtttgcg atgttttcag atctgcgctg gcttatacga cgaatttgtt cttattcgtg | 480 |
| actttccgct tgattgacct gttttacctc tggaatctca cacgtgatca ataaggctg | 540 |
| ctattttagt tgaagtagaa tctatacaca ctttgtagca ttctttttac gatcacttac | 600 |
| acgggtggtt tttaatcagg cttttttgt ggggtataa acatcttcct cctcgattct | 660 |
| ttccgataaa agcttaattg gattataggga agtgggaaac aatgcgtggg agctctttgg | 720 |
| tttgttttc gtaggttaaa cttgcaggtt taagttctga atcaggagtt ccaaatatag | 780 |
| aggctggggg cataaaaaaa gagaattcta tggatctgtt ctgaaattgg agccactgtt | 840 |
| tcgagttgct attttttac tagtattaat aagaacaagt ttgcttttta ttttacattt | 900 |
| tttcccgttt cttttgccaa aagtatttat gatcactctc ttctgtttgt gatattactt | 960 |
| ataagtgctg tgctgtaatt atttgttatt tggggtgaag tataattttt gggtgaactt | 1020 |
| ggagcgtttt tagttagatt gatttctcga tatcatttaa ggtttaggtt gacccccttcc | 1080 |
| actcgtttgt ggttgattgt tttttttttt ttatctctta tcatttacag tgcttctttg | 1140 |
| cctattttt tcattatccc ctttcgtgaa aggtaggaga agaaaaacaa tgacttgcgt | 1200 |
| aaattttgca tgcag | 1215 |

<210> SEQ ID NO 45
<211> LENGTH: 338
<212> TYPE: DNA
<213> ORGANISM: Glycine max

<400> SEQUENCE: 45

```
gtcagctttt gcaaaaaatt gctgagaatt gcattcagca atcacgataa atataacttt    60
taataaatta ttatagaagt taagtaactt atcacgggtt gtcaacaaaa atttagagaa   120
taattgcata ggacaaaact tacctacagt tcgtttgaca ttttttgtgt cgttttaaa    180
tcaaaattaa aatttatct tggtaatttg cagattatta gatacaactc caatttcgat    240
caaagaacaa tgccaaaaac acctatggaa tctaagtttt gtgcaattgc ttattgatga   300
ttttatttta ttgcctaaat tgtctgtttt ccaaacag                           338
```

<210> SEQ ID NO 46
<211> LENGTH: 641
<212> TYPE: DNA
<213> ORGANISM: Glycine max

<400> SEQUENCE: 46

```
gtaagttggt gtgactaaga agaaccttt tgatgtgtga agaattgcaa aggcgtccat    60
gctcagctgt gaaatcttct tttgccttac tcatctttac tttgacttta tatagtatct   120
ggttgaatta ttttgtactt ctgcatttgt ttctgtcact tgtgctttt tgtttcacaa    180
aattggtatg atagttagga acttgggatt aaaggcatgt ttggaatata ttgtgattgt   240
gaattatttt taaaaatatt ttcacttttc aaaatctatc tcatgaatct gtaaaaataa   300
gaataaaaaa taaaactact gtaatgtgta taaaaaattc ttcttggatg gtaattgatc   360
tgataagcac atgctttta cataatgaat tatatgaagt cctttgcctt aagtctgtta   420
gactgggtat gagatatggt agtaaattct ttttacattc cgtacatttt tttgcatatt   480
tctgtcttat tattgtaaaa tgttggatgc atatacaggt tttcaaaaga agcaacttat   540
accatgtgcc cttttctgca ttttggtctg ttcgagaata atctctttag taaattctga   600
atctgttcat ctgaagttga gtgaatctat atttgcttca g                      641
```

<210> SEQ ID NO 47
<211> LENGTH: 367
<212> TYPE: DNA
<213> ORGANISM: Glycine max

<400> SEQUENCE: 47

```
gtagatatca gtttcaggaa tcctttttt ctgttgccta tagacatgtt ttgaagagtt    60
tttctgaatc tgaatgtttc tctctggtga tttggcactg cttttaatct cacgaggctg   120
tgtgaagtta tctattatca tatttacttt ctccttaatac accactattg aaaggcaatt   180
cattacagat ttaagcatac aaaattttgt tgatgataat ttttaatctc accaacagta   240
tctaatatct tcttaatttg ttattaagta ccagccttca acttgtgtac atgttgcacc   300
ttggtgctac gaacttataa gcattttctg attggttgag tttgattttg attttgatgt   360
tatgcag                                                             367
```

<210> SEQ ID NO 48
<211> LENGTH: 18
<212> TYPE: DNA
<213> ORGANISM: Artificial sequence
<220> FEATURE:
<223> OTHER INFORMATION: PCR primer

<400> SEQUENCE: 48

```
ctgtttccac tttccagg                                                  18
```

```
<210> SEQ ID NO 49
<211> LENGTH: 17
<212> TYPE: DNA
<213> ORGANISM: Artificial sequence
<220> FEATURE:
<223> OTHER INFORMATION: PCR primer

<400> SEQUENCE: 49
cttctcgttt gttgagc                                                17

<210> SEQ ID NO 50
<211> LENGTH: 16
<212> TYPE: DNA
<213> ORGANISM: Artificial sequence
<220> FEATURE:
<223> OTHER INFORMATION: PCR primer

<400> SEQUENCE: 50
cagctgcaac ttcatc                                                 16

<210> SEQ ID NO 51
<211> LENGTH: 16
<212> TYPE: DNA
<213> ORGANISM: Artificial sequence
<220> FEATURE:
<223> OTHER INFORMATION: PCR primer

<400> SEQUENCE: 51
cttccccatt aggtcc                                                 16

<210> SEQ ID NO 52
<211> LENGTH: 18
<212> TYPE: DNA
<213> ORGANISM: Artificial sequence
<220> FEATURE:
<223> OTHER INFORMATION: PCR primer

<400> SEQUENCE: 52
cacttaatca tgttaaga                                               18

<210> SEQ ID NO 53
<211> LENGTH: 17
<212> TYPE: DNA
<213> ORGANISM: Artificial sequence
<220> FEATURE:
<223> OTHER INFORMATION: PCR primer

<400> SEQUENCE: 53
gtcgtgattg gcttgtg                                                17

<210> SEQ ID NO 54
<211> LENGTH: 17
<212> TYPE: DNA
<213> ORGANISM: Artificial sequence
<220> FEATURE:
<223> OTHER INFORMATION: PCR primer

<400> SEQUENCE: 54
ctctgctcca gttgtgc                                                17

<210> SEQ ID NO 55
<211> LENGTH: 18
<212> TYPE: DNA
<213> ORGANISM: Artificial sequence
<220> FEATURE:
<223> OTHER INFORMATION: PCR primer
```

```
<400> SEQUENCE: 55
gcgagggtga agtaacag                                                   18

<210> SEQ ID NO 56
<211> LENGTH: 18
<212> TYPE: DNA
<213> ORGANISM: Artificial sequence
<220> FEATURE:
<223> OTHER INFORMATION: PCR primer

<400> SEQUENCE: 56
gcacaaacct tgtttctg                                                   18

<210> SEQ ID NO 57
<211> LENGTH: 17
<212> TYPE: DNA
<213> ORGANISM: Artificial sequence
<220> FEATURE:
<223> OTHER INFORMATION: PCR primer

<400> SEQUENCE: 57
caagaagccc agcagtc                                                    17

<210> SEQ ID NO 58
<211> LENGTH: 17
<212> TYPE: DNA
<213> ORGANISM: Artificial sequence
<220> FEATURE:
<223> OTHER INFORMATION: PCR primer

<400> SEQUENCE: 58
gatttcacca gatttcg                                                    17

<210> SEQ ID NO 59
<211> LENGTH: 17
<212> TYPE: DNA
<213> ORGANISM: Artificial sequence
<220> FEATURE:
<223> OTHER INFORMATION: PCR primer

<400> SEQUENCE: 59
gtgcgaatga aattagc                                                    17

<210> SEQ ID NO 60
<211> LENGTH: 17
<212> TYPE: DNA
<213> ORGANISM: Artificial sequence
<220> FEATURE:
<223> OTHER INFORMATION: PCR primer

<400> SEQUENCE: 60
ctttctgctg gaactgg                                                    17

<210> SEQ ID NO 61
<211> LENGTH: 2683
<212> TYPE: DNA
<213> ORGANISM: Glycine max
<220> FEATURE:
<221> NAME/KEY: gene
<222> LOCATION: (1)..(2683)
<223> OTHER INFORMATION: FAD3-1B gene

<400> SEQUENCE: 61
gttcaagcac agcctctaca acatgttggt aatggtgcag ggaaagaaga tcaagcttat     60
```

-continued

```
tttgatccaa gtgctccacc acccttcaag attgcaaata tcagagcagc aattccaaaa    120
cattgctggg agaagaacac attgagatct ctgagttatg ttctgaggga tgtgttggta    180
gtgactgcat yggtagctgc agcaatcggc ttcaatagct ggttcttctg gccactctat    240
yggcctgcac aaggcacaat gttttgggca cttttttgttc ttggacatga ttggtaacta    300
attattatta caaattgtta tgttatgtta tgttatgttg ttgtgccttt ttctcagtga    360
tgctttagtc atttcatttc acttggttat gcatgattgt tcgttcatat gttcgtcat    420
ggtgagttct aatttgattg atgcatggaa cagtggtcat ggaagttttt caaacagtcc    480
tttgttgaac agcattgtgg gccacatctt gcactcttca attcttgtac cataccatgg    540
atggtcggtt ccttttagca acttttcatg ttcactttgt ccttaaattt tttttatgt    600
ttgttaaaaa atctttggtc tgatttaaca acctaaccat ttttacaacw catggattw    660
ttgcaggaga attagccaca ggactcacca tcagaaccat ggccatgttg agaaggatga    720
atcatgggtt ccggtattac tatgagtttg cttgattaat ttccacattt tttctttctt    780
cttaattta atcagtggtt agatttggtt gtgttccaat agaagaaaag ggggtatcta    840
gagagatgtg aatttcatga agtggttcat gattatgtgt ctttatgcct ttatgtcagc    900
ttacagagaa agtttacaag aatctagaca acatgacaag aatgatgaga ttcactcttc    960
ctttccccat ctttgcatac ccctttatt tggtgagacc ctcttttcc agaatgacag    1020
cattatttta ctatatagta cctcaatttt tatatttcta aaattttgaa ttcttgaaat    1080
tgaaaggaaa ggactttatt gggtctagca tctcactctc tctttgtgat atgaaccata    1140
tatttcagtg gagcagaagc cctggaaaag aaggctctca tttcaaccct tacagcaact    1200
tgttctctcc tggtgagaga agagatgtgc taacttcaac tctgtgttgg ggcatcatgc    1260
tttctgtgct tctctatctt tccctcacaa tgggtccact ttttatgctc aagctctatg    1320
gggttcccta tttggtaatc tcactctcac actttcttta tacatcgcac accagtgtgg    1380
gttatttgca acctacaccg aagtaatgcc ctataattaa tgaggttaac acatgtccaa    1440
gtccaatatt ttgttcactt atttgaactt gaacatgtgt agatcttcgt catgtggctg    1500
gatttcgtca cgtacttgca tcatcatggt tacaagcaga aactgccttg gtaccgtggc    1560
caggtatccc atttaacaca atttgtttca ttaacatttt aagagaattt ttttttcaaa    1620
atagttttcg aaattaagca ataccaagc aaattgttag atctacgctt gtacttgttt    1680
taaagtcaaa ttcatgacca aattgtcctc acaagtccaa accgtccact attttatttt    1740
cacctacttt atagcccaat ttgtcatttg gttacttcag aaaagagaac cccatttgta    1800
gtaaatatat tatttatgaa ttatggtagt ttcaacataa aacatattta tgtgcagttt    1860
tgccatcctt caaagaaga tagaaactta ctccatgtta ctctgtctat atgtaatttc    1920
acaggaatgg agttatctaa ggggtggtct tacaacagta gatcgcgact atggttggat    1980
caacaacatt caccatgaca ttggcaccca tgttatccat cacctttttcc ctcaaattcc    2040
acattatcat ttaatcgaag cggtattaat tctctatttc acaagaaatt attgtatgtc    2100
tgcctatgtg atctaagtca attttcacat aacacatgat caaactttct taattctttc    2160
ttctaaattg aaaagtggaa ttatatgtca attgaaaatt ggtcaagacc acaaacatgt    2220
gatgatctcc caccttacat ataataattt ctcctattct acaatcaata atccttctat    2280
ggtcctgaat tgttcctttc ttttttcatt ttcttattct ttttgttgtc ccacaataga    2340
ctaaagcagc aaaggcagtg ctaggaaagt attatcgtga gcctcagaaa tctgggccat    2400
tgccacttca tctaataaag tacttgctcc acagcataag tcaggatcac ttcgttagcg    2460
```

-continued

```
actctggcga cattgtgtac taccagactg attcccagct ccacaaagat tcttggaccc    2520
agtccaacta aagtttttga tgctacattt acctatttca ctcttaaata ctatttccta    2580
tgtaatatgt aatttagaat atgttaccta ctcaaatcaa ttaggtgaca tgtataagct    2640
ttcataaatt atgctagaaa tgcacttact ttacaaagca tgc                      2683

<210> SEQ ID NO 62
<211> LENGTH: 4160
<212> TYPE: DNA
<213> ORGANISM: Glycine max
<220> FEATURE:
<221> NAME/KEY: gene
<222> LOCATION: (1)..(4160)
<223> OTHER INFORMATION: FAD3-1C gene

<400> SEQUENCE: 62
aaagatttca ttcttcctct tctaggttat tacgcaccac ccaccacgta tccctgaaag      60
agagaaaaac acactaagcc aaagccaaag cagcaatggt taaagacaca aagcctttag     120
cctatgctgc taataatgga taccaaaagg aagcttttga tcccagtgct cctccaccgt     180
ttaagattgc agaaatcaga gttgcaatac caaaacattg ctgggtcaag aatccatgga     240
gatccctcag ttatgttctc agggatgtgc ttgtaattgc tgcattgatg gctgctgcaa     300
gtcacttcaa caactggctt ctctggctaa tctattggcc cattcaagga caatgttct      360 gggctctgtt tgttcttgga catgattggt aattaattat ttgttgttac ttttttgtta     420
taatatgaat ctcacacact gctttgttat gcctacctca tttcatttgg ctttagacaa     480
cttaaatttg agatctttat tatgtttttt gcttatatgg taaagtgatt cattcttcac     540
attgaattga acagtggcca tggaagcttt tcagacagcc cttttctaaa tagcctggtg     600
ggacacatct tgcattcctc aattcttgtg ccataccatg gatggttagt tcatcccggc     660 tttttttgttt gtcattggaa gttctttttat tgattcaatt tttatagcgt gttcggaaac     720
gcgtttcaga aaataatgaa atacatcttg aatctgaaag ttataacttt tagcttcatt     780
gtcattgaaa gttcttttat taattatatt tttattgcgt gtttggaatc ccatttgaga     840
aataagaaat cacgtttaaa atgtgaaagt tataactatt aacttttgac taaacttgaa     900
aaaatcacat ttttgatgtg gaaccaaatc tgatttgaga accaagttga ttttgatgga     960
ttttgcagga gaattagcca cagaactcac catcaaaatc atggacacat tgagaaggat    1020
gaatcctggg ttccagtatg tgattaacta cttcctctat agttattttt gattcaatta    1080
aatttattta tttaataagt tcaagaaaaa aggaatcttt tacttcatg ataaagctgt      1140 tcttgaacat ttttttttgt cattatctta gttaaccgag aagatttaca agaatctaga    1200
caacatgaca agacttgtta gattcactgt gccatttcca ttgtttgtgt atccaattta    1260
tttggkgagk gcttttttttt ttttacttgg aagactacaa cacattatta ttattataat    1320
atggttcaaa tcaatgactt ttaatttctt tgtgatgtgc actccatttt cagttctcaa    1380
gaagccccgg aaaggaaggt tctcacttca atccctacag caatctgttc ccacccagtg    1440
agagaaaggg aatagcaata tcaacactgt gttgggttac catgttttct atgcttatct    1500
atctctcctt cataactagt ccagttctat tgctcaagct ctatggaatt ccatattggg    1560
taattaaatt actcttacat tacttttttcc tctttttttt tatgggtctt aactagtatc    1620
acaaaaatat tggttaaaaa atttaaaaaa atatttatt atgtaaatca taaagaaca      1680 taaaaaaat gatgaataac ataatttttcg tctcttatta aaaatatttt tattttaaat    1740
```

```
ttcttaatca atatatttaa aatctggtta acattttttg aatatttcaa ttctccaatt    1800
aaaaatttga aatagtcacc attaattatg taattgtttg aacacgtgca gatatttgtt    1860
atgtggctgg actttgtcac atacttgcat caccatggtc atcatcagaa actgccttgg    1920
tatcgcggca aggtaacaaa aataaataga aaatagtgag tgaacactta aatgttagat    1980
actaccttct tcttcttctt tttttttttt ttgaggttaa tgctagataa tagctagaaa    2040
gagaaagaaa gacaaatata ggtaaaaata aataatataa cctgggaaga agaaaacata    2100 aaaaagaaa taatagagtc tacgtaatgt ttggattttt gagtgaaatg gtgttcacct    2160
accattactc aaagattctg ttgtctacgt agtgtttgga ctttggagtg aaatggtgtt    2220
cacctaccat tactcagatt ctgttgtgtc ccttagttac tgtcttatat tcttagggta    2280
tattctttat tttacatcct tttcacatct tacttkaaaa gatttttaat tattcattga    2340
aatattaacg tgacagttaa attaaaataa taaaaaattc gttaaaactt caaataaata    2400
agagtgaaag gatcatcatt tttcttcttt cttttattgc gttattaatc atgcttctct    2460 tcttttttt cttcgctttc cacccatatc aaattcatgt gaagtatgag aaaatcacga    2520
ttcaatggaa agctacagga acttttttg ttttgttttt ataatcggaa ttaatttata    2580
ctccattttt tcacaataaa tgttacttag tgccttaaag ataatatttg aaaaattaaa    2640
aaaattatta atacactgta ctactatata atatttgaca tatatttaac atgattttct    2700
attgaaaatt tgtatttatt attttttaat caaaacccat aaggcattaa tttacaagac    2760
ccatttttca tttatagctt tacctgtgat catttatagc tttaagggac ttagatgtta    2820
caatcttaat tacaagtaaa tatttatgaa aaacatgtgt cttacccctt aaccttacct    2880
caacaaagaa agtgtgataa gtggcaacac acgtgttgct tttttggccc agcaataaca    2940
cgtgtttttg tggtgtacaa aaatggacag gaatggagtt atttaagagg tggtctcaca    3000
actgtggatc gtgactatgg ttggatcaat aacattcacc atgacattgg cacccatgtt    3060
attcaccatc ttttccctca aattcctcat tatcacctcg ttgaagcggt atatttact    3120 attattactc acctaaaaag aatgcaatta gtacatttgt tttatctctt ggaagttagt    3180
cattttcagt tgcatgattg taatgttctc tctatttta aaccatgttt tcacacctac    3240
ttcgtttaaa ataagaatgt ggatactatt ctaatttcta ttaacttctt ttaaaaaata    3300
atgtaaaact agtattaaaa aagaggaaat agattacact ctactaatac taatagtata    3360
aaaaaaatta cattgttatt ttatcacaaa taattatata taattaattt ttacaatcat    3420
tatcttaaaa gtcatgtatg atatacagtt tttacatgct ttggtactta ttgtaaagtt    3480
agtgatttat tcattattta tgttatataa ttggcataaa tatcatgtaa ccagctcact    3540
atactataat gggaacttgg tggtgaaagg ggtttacaac cctctttttct aggtgtaggt    3600 gctttgatac ttctggtccc ttttatatc aatataaatt atattttgct gataaaaaaa    3660
acattattaa tatataatca ttaacttctt taaaaaccgt acctaaaact ttatattatt    3720
aaaaagaaga ttgagatcag caaaagaaaa aaaaattaac agtcatttga attcactgca    3780
gacacaagca gcaaaatcag ttcttggaga gtattaccgt gagccagaaa gatctgcaca    3840
ttaccatttc atctaataaa gtatttaatt cagagtatga gacaagacca cttcgtaagt    3900
gacactggag atgtggttta ttatcagact gattctctgc accttcactc gcaccgagac    3960
tgagtttcaa ttttggggtt atttattgga ttctagctac tcaaattact ttttttttaa    4020
tgttacgttt ttggagtttt aacgttttct gaacaacttg caaattacat gcatagagag    4080
acaggaattc atagtgggcc tcaatggaat atttatttga aattagtaag gtggtaatta    4140
```

-continued ataaatattg aattgtcagt                                           4160

<210> SEQ ID NO 63
<211> LENGTH: 994
<212> TYPE: DNA
<213> ORGANISM: Glycine max
<220> FEATURE:
<221> NAME/KEY: promoter
<222> LOCATION: (1)..(994)
<223> OTHER INFORMATION: FAD3-1C promoter

<400> SEQUENCE: 63
tgctacgaag caatttgcat gctaggaagc aaagtaaaat tctcaaactg tataacttat      60
tttctcttgt tgtatataaa actagtcatt tttcattaaa aagcattgta taatagttta     120
atgggtcatt gaaattatta taattaatgt cattctatttt ttaatactcc ttttgtttga   180
taatgattat cgtttcatgt tattttctat acatatcaag acaaattaat aaatggataa     240
aaaagtatca attttataaa attaatatta ttattattaa tttatttata attttttgtt     300
atcatttata ttataagtaa tatattattg gcaaaaataa tttttgatca attatatttta    360 cctgtcggtc gaactctaga ttatgctggg tatcttctcc aaatgaatcc aaagattaaa     420
ataaaataaa attataagta atataaataa aaaacaatta atactagatt aacaagacta     480
aaataataat tattttataa tttattttct tcaataattg tagaatacaa ggagtaatat     540
ttaatgttgt ttaattcttg tttcaataat tgagatgttt tgaacaaatt aaataattat     600
tgtaaataga ataacattaa ttacaataat aaaatcattt taacgatcca ttaaacttaa     660
atgataaaat tcaactaact aatttggagt aattaagaaa aatagttaat ttagacaaca    720
atattaaatt tttgctaaat tatatgttttt tctcaaaatt acctataaca ttaataagac    780 atactttttat ttttcaaaga tttctactta attaaccgcc acaaattcat cctcgctggt    840
ttgtcctaca ccgtatgttt tttgacgtca gctaggcaaa ccaacataaa taggaagcag     900
tagaagtaaa agtagaatgt ggtagtgtta ttattattta ctactgtttc accttggtgt    960
tatataaatg cactaccca taattgaatt tttc                                  994

<210> SEQ ID NO 64
<211> LENGTH: 5
<212> TYPE: PRT
<213> ORGANISM: Glycine max

<400> SEQUENCE: 64

His Val Ile His His
1               5

<210> SEQ ID NO 65
<211> LENGTH: 5
<212> TYPE: PRT
<213> ORGANISM: Glycine max

<400> SEQUENCE: 65

His Val Ile His Tyr
1               5